United States Patent
Wang et al.

(10) Patent No.: US 10,584,169 B2
(45) Date of Patent: Mar. 10, 2020

(54) ANTI-CD73 ANTIBODIES AND USES THEREOF

(71) Applicant: I-MAB, Grand Cayman (KY)

(72) Inventors: Zhengyi Wang, Shanghai (CN); Lei Fang, Shanghai (CN); Bingshi Guo, Shanghai (CN); Jingwu Zang, Shanghai (CN)

(73) Assignee: I-MAB BIOPHARMA US LIMITED, Gaithersburg, MD (US)

( * ) Notice: Subject to any disclaimer, the term of this patent is extended or adjusted under 35 U.S.C. 154(b) by 0 days.

(21) Appl. No.: 16/069,144

(22) PCT Filed: Jan. 23, 2018

(86) PCT No.: PCT/CN2018/073746
§ 371 (c)(1),
(2) Date: Jul. 10, 2018

(87) PCT Pub. No.: WO2018/137598
PCT Pub. Date: Aug. 2, 2018

(65) Prior Publication Data
US 2019/0256598 A1    Aug. 22, 2019

(30) Foreign Application Priority Data
Jan. 24, 2017  (WO) ................ PCT/CN2017/072445

(51) Int. Cl.
| | |
|---|---|
| A61K 39/395 | (2006.01) |
| C07K 16/28 | (2006.01) |
| A61P 35/00 | (2006.01) |
| A61K 9/00 | (2006.01) |
| A61K 9/06 | (2006.01) |
| A61K 35/17 | (2015.01) |
| C07K 16/40 | (2006.01) |
| G01N 33/574 | (2006.01) |
| A61K 39/00 | (2006.01) |

(52) U.S. Cl.
CPC .......... *C07K 16/2818* (2013.01); *A61K 9/006* (2013.01); *A61K 9/0019* (2013.01); *A61K 9/0031* (2013.01); *A61K 9/0034* (2013.01); *A61K 9/0043* (2013.01); *A61K 9/06* (2013.01); *A61K 35/17* (2013.01); *A61K 39/39558* (2013.01); *A61P 35/00* (2018.01); *C07K 16/2896* (2013.01); *C07K 16/40* (2013.01); *G01N 33/574* (2013.01); *G01N 33/57407* (2013.01); *A61K 2039/505* (2013.01); *A61K 2039/507* (2013.01); *C07K 2317/24* (2013.01); *C07K 2317/33* (2013.01); *C07K 2317/34* (2013.01); *C07K 2317/55* (2013.01); *C07K 2317/73* (2013.01); *C07K 2317/76* (2013.01); *C07K 2317/77* (2013.01); *C07K 2317/92* (2013.01)

(58) Field of Classification Search
None
See application file for complete search history.

(56) References Cited

FOREIGN PATENT DOCUMENTS

| | | |
|---|---|---|
| WO | WO 2016/055609 | 4/2016 |
| WO | WO 2016/075176 | 5/2016 |
| WO | WO 2016/081746 | 5/2016 |
| WO | WO 2016/081748 | 5/2016 |

OTHER PUBLICATIONS

International Search Report for PCT/CN2018/073746 dated Apr. 9, 2018 (8 pages).
Written Opinion for PCT/CN2018/073746 dated Apr. 19, 2018 (5 pages).
Allard, B et al, Targeting CD73 and downstram adenosine receptor signaling in triple-negative breast cancer, Expert. Opin. Ter.Targets, May 6, 2014 No. 8, vol. 18, pp. 863-881.
Antonioli, L. et al., "Anti-CD73 in Cancer Immunotherapy: Awakening New Opportunities" Trends in Cancer 29, Feb. 29, 2016, No. 2, vol. 2 pp. 95-109.
Stagg, J. et al., Anti-CD73 antibody therapy inhibits breast tumor grown and metastasis, PNAS, Jan. 26, 2010, No. 4., vol. 107, pp. 1547-1552.

*Primary Examiner* — Mark Halvorson
(74) *Attorney, Agent, or Firm* — Sheppard Mullin Richter & Hampton LLP

(57) ABSTRACT

Provided are anti-CD73 antibodies or fragments thereof. The antibodies or fragments therefore include a VH CDR1 of SEQ ID NO: 1, a VH CDR2 of SEQ ID NO: 2, a VH CDR3 of SEQ ID NO: 3, a VL CDR1 of SEQ ID NO: 4, a VL CDR2 of SEQ ID NO: 5, and a VL CDR3 of SEQ ID NO: 6, or variants of each thereof. More generally, antibodies or fragments thereof are described which have specificity to one or more amino acid residues selected from the C-terminal half of a human CD73 protein, such as those in the C-terminal domains. Specific epitope amino acids in these domains include Y345, D399, E400, R401 and R480. Methods of using the antibodies or fragments thereof for treating and diagnosing diseases such as cancer are also provided.

14 Claims, 26 Drawing Sheets
Specification includes a Sequence Listing.

| Mutation | Binding Reactivity (% WT) | | |
|---|---|---|---|
| | Hu101-28 Fab HS | 4G4 MAb | 7G2 MAb |
| Y345A | 2.7 (0) | 103.9 (16) | 112.7 (25) |
| D399A | 1.8 (0) | 90.4 (16) | 114.2 (19) |
| E400A | 3.6 (1) | 85.4 (10) | 118.6 (12) |
| R401A | 1.1 (0) | 101.7 (14) | 98.9 (24) |
| R480A | -0.9 (0) | 83.2 (18) | 65.2 (7) |

FIG. 23

ANTI-CD73 ANTIBODIES AND USES THEREOF

CROSS REFERENCE TO RELATED APPLICATIONS

The present application is the U.S. national stage application of International Application PCT/CN2018/073746, filed Jan. 23, 2018, which claims priority to International Application PCT/CN2017/072445, filed Jan. 24, 2017, the contents of each of which are incorporated herein by reference in their entireties in the present disclosure.

SEQUENCE LISTING

The instant application contains a Sequence Listing which has been submitted in ASCII format via EFS-Web and is hereby incorporated by reference in its entirety. Said ASCII copy, created on Sep. 17, 2019, is named 250265-US_ST25.txt and is 34,598 bytes in size.

BACKGROUND

CD73, cluster of differentiation 73, is also known as 5'-nucleotidase (5'-NT) or ecto-5'-nucleotidase, is an enzyme serves to convert AMP to adenosine. CD73 catalyzes the formation of extracellular adenosine which contributes to the immunosuppressive tumor environment. CD73 is over-expressed in stromal cells and multiple types of tumor cells, as well as in Tregs, M2 Mφs and myeloid derived suppressor cells (MDSCs).

Preclinical evidence shows that CD73 inhibition prevented adenosine-mediated lymphocyte suppression, increased the activity of CD8+ effector cells, and reduced both MDSCs and Tregs. There are a few anti-CD73 antibodies being developed as potential anticancer agents, but none have been approved for clinical use.

SUMMARY

The present disclosure provides anti-CD73 antibody having high binding affinity to human CD73 proteins and having potent activities inhibiting the enzymatic activity of CD73 whether alone or present on a cell. Further, the binding of these antibodies can induce tumor cell internalization of CD73, leading to further reduction of CD73 activity on the cell surface. Also surprisingly, monovalent units, e.g., Fab fragments, of these antibodies have potencies comparable those of the entire antibodies. Known anti-CD73 antibodies, such as MEDI-9447 from Medimmune, however, do not have such characteristics. Likewise, different from MEDI-9447 and 11F11 which require high density of CD73 expression on the cell surface to exhibit their inhibition effect, the antibodies of the present disclosure can reach complete CD73 inhibition at different levels of cell surface expression. These surprising and unexpected properties of the presently disclosed antibodies are believed to be at least in part attributed to the distinct binding site on the CD73 protein. Unlike MEDI-9447 and 11F11 that bind the N-terminal domains of the CD73 protein, the presently disclosed antibodies bind to the C-terminal domains, and more particularly amino acid residues Y345, D399, E400, R401 and R480. These properties of the presently disclosed antibodies make them superior candidates for therapeutic and diagnostics uses.

In accordance with one embodiment of the present disclosure, therefore, provided is an isolated antibody or fragment thereof which has specificity to a human CD73 protein and binds to one or more amino acid residues selected from the C-terminal portion of the human CD73 protein. The C-terminal portion of the human CD73 protein, as known in the art, includes 238 amino acid residues starting from residue 337, as shown in SEQ ID NO: 61.

In some embodiments, the antibody or fragment thereof binds to one or more of the C-terminal domains of the human CD73 protein. In some embodiments, the antibody or fragment thereof binds to at least one of amino acid residues selected the group consisting of Y345, D399, E400, R401 and R480 of the human CD73 protein. In some embodiments, the antibody or fragment thereof binds to at least two of the amino acid residues.

One embodiment of the present disclosure provides an anti-CD73 antibody or fragment thereof that comprises a VH CDR1 of SEQ ID NO: 1, a VH CDR2 of SEQ ID NO: 2, a VH CDR3 of SEQ ID NO: 3, a VL CDR1 of SEQ ID NO: 4, a VL CDR2 of SEQ ID NO: 5, and a VL CDR3 of SEQ ID NO: 6. In some embodiments, the antibody or fragment thereof can further comprise a heavy chain constant region, a light chain constant region, an Fc region, or the combination thereof. In some embodiments, the light chain constant region is a kappa or lambda chain constant region. In some embodiments, the antibody or fragment thereof is of an isotype of IgG, IgM, IgA, IgE or IgD, or more particularly, IgG1, IgG2, IgG3 or IgG4.

In some embodiments, the antibody or fragment thereof is a chimeric antibody, a humanized antibody, or a fully human antibody. In one embodiment, the antibody or fragment thereof is a humanized antibody.

In some embodiments, the human or humanized antibody or fragment thereof has a heavy chain variable region comprising one or more amino acid residues selected from the group consisting of: (a) Thr at position 30, (b) Lys at position 44, (c) Met at position 48, (d) He at position 67, and (e) Arg at position 71, according to Kabat numbering, and combinations thereof. In some embodiments, the human or humanized antibody or fragment thereof has a light chain variable region comprising one or more amino acid residues selected from the group consisting of: (a) Ser at position 5, (b) Pro at position 46, (c) Trp at position 47, (d) Ser at position 49, (e) Ser at position 70, and (f) Tyr at position 71, according to Kabat numbering, and combinations thereof.

Example CD73 antibodies or fragments therefore include those that have a heavy chain variable region comprising an amino acid sequence selected from the group consisting of SEQ ID NO: 7 and 9-13, or a peptide having at least 90% sequence identity to an amino acid sequence selected from the group consisting of SEQ ID NO: 7 and 9-13. In some embodiments, the heavy chain variable region comprises the amino acid sequence of SEQ ID NO: 7 or 9. In some embodiments, the antibody or fragment thereof comprises a light chain variable region comprising an amino acid sequence selected from the group consisting of SEQ ID NO: 8, 15-20 and 22-24, or a peptide having at least 90% sequence identity to an amino acid sequence selected from the group consisting of SEQ ID NO: 8, 15-20 and 22-24. In some embodiments, the light chain variable region comprises the amino acid sequence of SEQ ID NO: 8.

As experimental example 7 shows, the CDR regions can accommodate certain amino acid addition, deletion or substitution that will retain or even improve the property of the anti-CD73 antibody. Accordingly, in some embodiments, an isolated antibody or fragment thereof is provided, wherein the antibody or fragment thereof has specificity to a human CD73 protein and comprises: (a) a VH CDR1 of SEQ ID NO: 1, or a variant of SEQ ID NO: 1 having a single substitution, deletion or insertion at location 1, 2 or 3 of SEQ ID NO: 1; (b) a VH CDR2 of SEQ ID NO: 2, or a variant of SEQ ID NO: 2 having a single substitution, deletion or insertion at location 6, 7, or 8 of SEQ ID NO: 2; (c) a VH CDR3 of SEQ ID NO: 3, or a variant of SEQ ID NO: 3 having a single substitution, deletion or insertion at location 7 or 8 of SEQ ID NO: 3; (d) a VL CDR1 of SEQ ID NO: 4, or a variant of SEQ ID NO: 4 having a single substitution, deletion or insertion at location 3 or 4 of SEQ ID NO: 4; (e) a VL CDR2 of SEQ ID NO: 5, and (f) a VL CDR3 of SEQ ID NO: 6, or a variant of SEQ ID NO: 6 having a single substitution, deletion or insertion at location 1, 2, 3 or 4 of SEQ ID NO: 6.

In some embodiments, an isolated antibody or fragment thereof is provided, wherein the antibody or fragment thereof has specificity to a human CD73 protein and comprises: (a) a VH CDR1 of SEQ ID NO: 1, or a variant of SEQ ID NO: 1 having a single substitution at location 1, 2 or 3 of SEQ ID NO: 1; (b) a VH CDR2 of SEQ ID NO: 2, or a variant of SEQ ID NO: 2 having a single substitution at location 6, 7, or 8 of SEQ ID NO: 2; (c) a VH CDR3 of SEQ ID NO: 3, or a variant of SEQ ID NO: 3 having a single substitution at location 7 or 8 of SEQ ID NO: 3; (d) a VL CDR1 of SEQ ID NO: 4, or a variant of SEQ ID NO: 4 having a single substitution at location 3 or 4 of SEQ ID NO: 4; (e) a VL CDR2 of SEQ ID NO: 5, and (f) a VL CDR3 of SEQ ID NO: 6, or a variant of SEQ ID NO: 6 having a single substitution at location 1, 2, 3 or 4 of SEQ ID NO: 6.

In some embodiments, the variant of SEQ ID NO: 1 is selected from the group consisting of SEQ ID NO: 26-29. In some embodiments, the variant of SEQ ID NO: 2 is selected from the group consisting of SEQ ID NO: 30-36. In some embodiments, the variant of SEQ ID NO: 3 is selected from the group consisting of SEQ ID NO: 37-41. In some embodiments, the variant of SEQ ID NO: 4 is selected from the group consisting of SEQ ID NO: 42-45. In some embodiments, the variant of SEQ ID NO: 6 is selected from the group consisting of SEQ ID NO: 46-56.

Also provided, in some embodiments, is a composition comprising the antibody or fragment thereof of the present disclosure and a pharmaceutically acceptable carrier. Also provided is an isolated cell comprising one or more polynucleotide encoding the antibody or fragment thereof of the present disclosure.

In another embodiment, the present disclosure provides a method of treating cancer in a patient in need thereof, comprising administering to the patient the antibody or fragment thereof of the present disclosure. In some embodiments, the cancer is selected from the group consisting of bladder cancer, breast cancer, colorectal cancer, endometrial cancer, esophageal cancer, head and neck cancer, kidney cancer, leukemia, liver cancer, lung cancer, lymphoma, melanoma, pancreatic cancer, prostate cancer, and thyroid cancer. In some embodiments, the cancer is a solid tumor.

In some embodiments, the method further comprises administering to the patient a second cancer therapeutic agent. In some embodiments, the second cancer therapeutic agent is an immune checkpoint inhibitor. In some embodiments, the inhibitor inhibits the expression or activity of programmed cell death protein 1 (PD-1), programmed death-ligand 1 (PD-L1), cytotoxic T-lymphocyte-associated protein 4 (CTLA-4), lymphocyte-activation protein 3 (LAG-3), or combinations thereof. In some embodiments, the inhibitor is an anti-PD-1 or anti-PD-L1 antibody. In some embodiments, the inhibitor is selected from the group consisting of pembrolizumab, nivolumab, J43, RMP1-14, atezolizumab, ipilimumab, and combinations thereof.

In one embodiment, a method of treating cancer in a patient in need thereof is provided, comprising: (a) treating a T cell, in vitro, with the antibody or fragment thereof of the present disclosure; and (b) administering the treated T cell to the patient. In some embodiment, the method further comprises, prior to step (a), isolating the T cell from an individual.

In some embodiments, the T cell is isolated from the patient. In some embodiments, the T cell is isolated from a donor individual different from the patient. In some embodiments, the T cell is a tumor-infiltrating T lymphocyte, a CD4+ cell, a CD8+ T cell, or the combination thereof.

Also provided, in another embodiment, is a method of detecting expression of CD73 in a sample, comprising contacting the sample with the antibody or fragment thereof of the present disclosure under conditions for the antibody or fragment thereof to bind to the CD73, and detecting the binding which indicates expression of CD73 in the sample. Still also provided, in one embodiment, is a method of identifying a cancer patient suitable for treatment with an anti-CD73 therapy, comprising isolated a cell from the cancer patient and detecting the presence of a CD73 protein with the antibody or fragment thereof of the present disclosure.

BRIEF DESCRIPTION OF THE DRAWINGS

FIG. 23 lists amino acid residues of CD73 that interacts with Hu101-28.

DETAILED DESCRIPTION

Definitions

Figure 1:
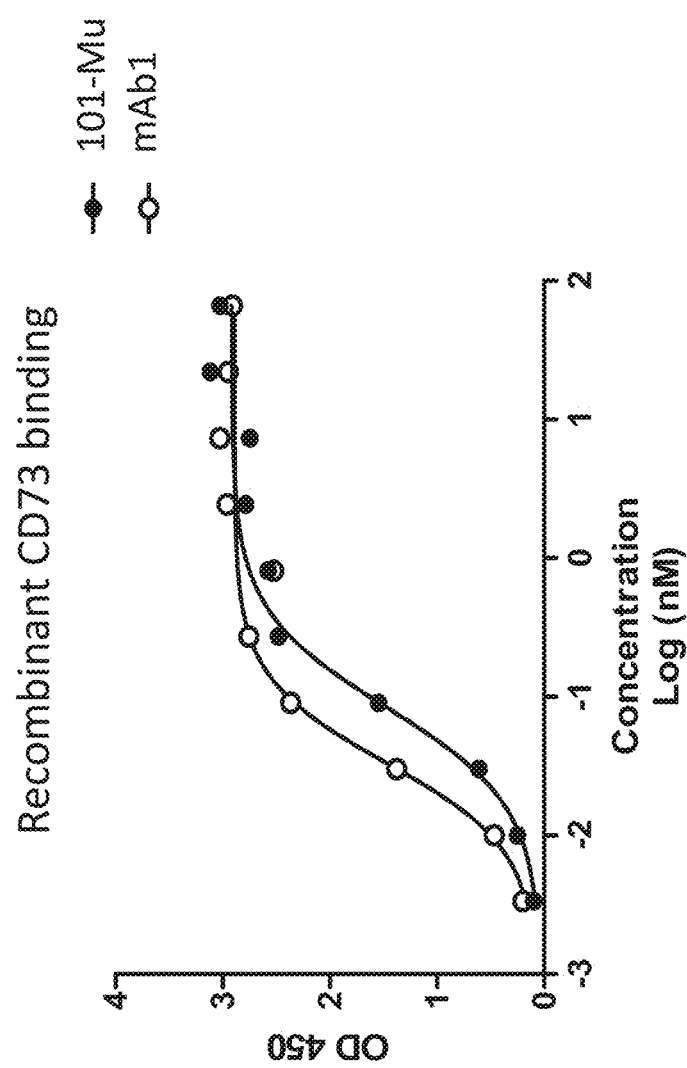
FIG. 1 shows the binding of the 101-Mu antibody to recombinant human CD73 protein.

It is to be noted that the term "a" or "an" entity refers to one or more of that entity; for example, "an antibody," is understood to represent one or more antibodies. As such, the terms "a" (or "an"), "one or more," and "at least one" can be used interchangeably herein.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

The term "isolated" as used herein with respect to cells, nucleic acids, such as DNA or RNA, refers to molecules separated from other DNAs or RNAs, respectively, that are present in the natural source of the macromolecule. The term "isolated" as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to cells or polypeptides which are isolated from other cellular proteins or tissues. Isolated polypeptides is meant to encompass both purified and recombinant polypeptides.

As used herein, the term "recombinant" as it pertains to polypeptides or polynucleotides intends a form of the polypeptide or polynucleotide that does not exist naturally, a non-limiting example of which can be created by combining polynucleotides or polypeptides that would not normally occur together.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the sequences of the present disclosure.

A polynucleotide or polynucleotide region (or a polypeptide or polypeptide region) has a certain percentage (for example, 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example those described in Ausubel et al. eds. (2007) Current Protocols in Molecular Biology. Preferably, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Biologically equivalent polynucleotides are those having the above-noted specified percent homology and encoding a polypeptide having the same or similar biological activity.

The term "an equivalent nucleic acid or polynucleotide" refers to a nucleic acid having a nucleotide sequence having a certain degree of homology, or sequence identity, with the nucleotide sequence of the nucleic acid or complement thereof. A homolog of a double stranded nucleic acid is intended to include nucleic acids having a nucleotide sequence which has a certain degree of homology with or with the complement thereof. In one aspect, homologs of nucleic acids are capable of hybridizing to the nucleic acid or complement thereof. Likewise, "an equivalent polypeptide" refers to a polypeptide having a certain degree of homology, or sequence identity, with the amino acid sequence of a reference polypeptide. In some aspects, the sequence identity is at least about 70%, 75%, 80%, 85%, 90%, 95%, 98%, or 99%. In some aspects, the equivalent polypeptide or polynucleotide has one, two, three, four or five addition, deletion, substitution and their combinations thereof as compared to the reference polypeptide or polynucleotide. In some aspects, the equivalent sequence retains the activity (e.g., epitope-binding) or structure (e.g., saltbridge) of the reference sequence.

Hybridization reactions can be performed under conditions of different "stringency". In general, a low stringency hybridization reaction is carried out at about 40° C. in about 10×SSC or a solution of equivalent ionic strength/temperature. A moderate stringency hybridization is typically performed at about 50° C. in about 6×SSC, and a high stringency hybridization reaction is generally performed at about 60° C. in about 1×SSC. Hybridization reactions can also be performed under "physiological conditions" which is well known to one of skill in the art. A non-limiting example of a physiological condition is the temperature, ionic strength, pH and concentration of $Mg^{2+}$ normally found in a cell.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching. The term "polymorphism" refers to the coexistence of more than one form of a gene or portion thereof. A portion of a gene of which there are at least two different forms, i.e., two different nucleotide sequences, is referred to as a "polymorphic region of a gene". A polymorphic region can be a single nucleotide, the identity of which differs in different alleles.

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, dsRNA, siRNA, miRNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this disclosure that is a polynucleotide encompasses both the double-stranded form and each of two complementary single-stranded forms known or predicted to make up the double-stranded form.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

As used herein, an "antibody" or "antigen-binding polypeptide" refers to a polypeptide or a polypeptide complex that specifically recognizes and binds to an antigen. An antibody can be a whole antibody and any antigen binding fragment or a single chain thereof. Thus the term "antibody" includes any protein or peptide containing molecule that comprises at least a portion of an immunoglobulin molecule having biological activity of binding to the antigen. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein.

The terms "antibody fragment" or "antigen-binding fragment", as used herein, is a portion of an antibody such as $F(ab')_2$, $F(ab)_2$, Fab', Fab, Fv, scFv and the like. Regardless of structure, an antibody fragment binds with the same antigen that is recognized by the intact antibody. The term "antibody fragment" includes aptamers, spiegelmers, and diabodies. The term "antibody fragment" also includes any synthetic or genetically engineered protein that acts like an antibody by binding to a specific antigen to form a complex.

A "single-chain variable fragment" or "scFv" refers to a fusion protein of the variable regions of the heavy ($V_H$) and light chains ($V_L$) of immunoglobulins. In some aspects, the regions are connected with a short linker peptide of ten to about 25 amino acids. The linker can be rich in glycine for flexibility, as well as serine or threonine for solubility, and can either connect the N-terminus of the $V_H$ with the C-terminus of the $V_L$, or vice versa. This protein retains the specificity of the original immunoglobulin, despite removal of the constant regions and the introduction of the linker. ScFv molecules are known in the art and are described, e.g., in U.S. Pat. No. 5,892,019.

The term antibody encompasses various broad classes of polypeptides that can be distinguished biochemically. Those skilled in the art will appreciate that heavy chains are classified as gamma, mu, alpha, delta, or epsilon ($\gamma$, $\mu$, $\alpha$, $\delta$, $\epsilon$) with some subclasses among them (e.g., $\gamma 1$-$\gamma 4$). It is the nature of this chain that determines the "class" of the antibody as IgG, IgM, IgA, IgG, or IgE, respectively. The immunoglobulin subclasses (isotypes) e.g., $IgG_1$, $IgG_2$, $IgG_3$, $IgG_4$, $IgG_5$, etc. are well characterized and are known to confer functional specialization. Modified versions of each of these classes and isotypes are readily discernable to the skilled artisan in view of the instant disclosure and, accordingly, are within the scope of the instant disclosure. All immunoglobulin classes are clearly within the scope of the present disclosure, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Antibodies, antigen-binding polypeptides, variants, or derivatives thereof of the disclosure include, but are not limited to, polyclonal, monoclonal, multispecific, human, humanized, primatized, or chimeric antibodies, single chain antibodies, epitope-binding fragments, e.g., Fab, Fab' and $F(ab')_2$, Fd, Fvs, single-chain Fvs (scFv), single-chain antibodies, disulfide-linked Fvs (sdFv), fragments comprising either a VK or VH domain, fragments produced by a Fab expression library, and anti-idiotypic (anti-Id) antibodies (including, e.g., anti-Id antibodies to LIGHT antibodies disclosed herein). Immunoglobulin or antibody molecules of the disclosure can be of any type (e.g., IgG, IgE, IgM, IgD, IgA, and IgY), class (e.g., IgG1, IgG2, IgG3, IgG4, IgA1 and IgA2) or subclass of immunoglobulin molecule.

Light chains are classified as either kappa or lambda (K, λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (VK) and heavy (VH) chain portions determine antigen recognition and specificity. Conversely, the constant domains of the light chain (CK) and the heavy chain (CH1, CH2 or CH3) confer important biological properties such as secretion, transplacental mobility, Fc receptor binding, complement binding, and the like. By convention the numbering of the constant region domains increases as they become more distal from the antigen-binding site or amino-terminus of the antibody. The N-terminal portion is a variable region and at the C-terminal portion is a constant region; the CH3 and CK domains actually comprise the carboxy-terminus of the heavy and light chain, respectively.

As indicated above, the variable region allows the antibody to selectively recognize and specifically bind epitopes on antigens. That is, the VK domain and VH domain, or subset of the complementarity determining regions (CDRs), of an antibody combine to form the variable region that defines a three dimensional antigen-binding site. This quaternary antibody structure forms the antigen-binding site present at the end of each arm of the Y. More specifically, the antigen-binding site is defined by three CDRs on each of the VH and VK chains (i.e. CDR-H1, CDR-H2, CDR-H3, CDR-L1, CDR-L2 and CDR-L3). In some instances, e.g., certain immunoglobulin molecules derived from camelid species or engineered based on camelid immunoglobulins, a complete immunoglobulin molecule may consist of heavy chains only, with no light chains. See, e.g., Hamers-Casterman et al., *Nature* 363:446-448 (1993).

In naturally occurring antibodies, the six "complementarity determining regions" or "CDRs" present in each antigen-binding domain are short, non-contiguous sequences of amino acids that are specifically positioned to form the antigen-binding domain as the antibody assumes its three dimensional configuration in an aqueous environment. The remainder of the amino acids in the antigen-binding domains, referred to as "framework" regions, show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen-binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined (see "Sequences of Proteins of Immunological Interest," Kabat, E., et al., U.S. Department of Health and Human Services, (1983); and Chothia and Lesk, *J. Mol. Biol.*, 196:901-917 (1987)).

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia et al., *J. Mol. Biol.* 196:901-917 (1987), which are incorporated herein by reference in their entireties. The CDR definitions according to Kabat and Chothia include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth in the table below as a comparison. The exact residue numbers which encompass a particular CDR will vary depending on the sequence and size of the CDR. Those skilled in the art can routinely determine which residues comprise a particular CDR given the variable region amino acid sequence of the antibody.

|  | Kabat | Chothia |
| --- | --- | --- |
| CDR-H1 | 31-35 | 26-32 |
| CDR-H2 | 50-65 | 52-58 |
| CDR-H3 | 95-102 | 95-102 |
| CDR-L1 | 24-34 | 26-32 |
| CDR-L2 | 50-56 | 50-52 |
| CDR-L3 | 89-97 | 91-96 |

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983).

In addition to table above, the Kabat number system describes the CDR regions as follows: CDR-H1 begins at approximately amino acid 31 (i.e., approximately 9 residues after the first cysteine residue), includes approximately 5-7 amino acids, and ends at the next tryptophan residue. CDR-H2 begins at the fifteenth residue after the end of CDR-H1, includes approximately 16-19 amino acids, and ends at the next arginine or lysine residue. CDR-H3 begins at approximately the thirty third amino acid residue after the end of CDR-H2; includes 3-25 amino acids; and ends at the sequence W-G-X-G, where X is any amino acid. CDR-L1 begins at approximately residue 24 (i.e., following a cysteine residue); includes approximately 10-17 residues; and ends at the next tryptophan residue. CDR-L2 begins at approximately the sixteenth residue after the end of CDR-L1 and includes approximately 7 residues. CDR-L3 begins at approximately the thirty third residue after the end of CDR-L2 (i.e., following a cysteine residue); includes approximately 7-11 residues and ends at the sequence F or W-G-X-G, where X is any amino acid.

Antibodies disclosed herein may be from any animal origin including birds and mammals. Preferably, the antibodies are human, murine, donkey, rabbit, goat, guinea pig, camel, llama, horse, or chicken antibodies. In another embodiment, the variable region may be condricthoid in origin e.g., from sharks).

As used herein, the term "heavy chain constant region" includes amino acid sequences derived from an immunoglobulin heavy chain. A polypeptide comprising a heavy chain constant region comprises at least one of: a CH1 domain, a hinge (e.g., upper, middle, and/or lower hinge region) domain, a CH2 domain, a CH3 domain, or a variant or fragment thereof. For example, an antigen-binding polypeptide for use in the disclosure may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the disclosure comprises a polypeptide chain comprising a CH3 domain. Further, an antibody for use in the disclosure may lack at least a portion of a CH2 domain (e.g., all or part of a CH2 domain). As set forth above, it will be understood by one of ordinary skill in the art that the heavy chain constant region may be modified such that they vary in amino acid sequence from the naturally occurring immunoglobulin molecule.

The heavy chain constant region of an antibody disclosed herein may be derived from different immunoglobulin molecules. For example, a heavy chain constant region of a polypeptide may comprise a CH1 domain derived from an $IgG_1$ molecule and a hinge region derived from an $IgG_3$ molecule. In another example, a heavy chain constant region can comprise a hinge region derived, in part, from an $IgG_1$ molecule and, in part, from an $IgG_3$ molecule. In another example, a heavy chain portion can comprise a chimeric hinge derived, in part, from an $IgG_1$ molecule and, in part, from an $IgG_4$ molecule.

As used herein, the term "light chain constant region" includes amino acid sequences derived from antibody light chain. Preferably, the light chain constant region comprises at least one of a constant kappa domain or constant lambda domain.

A "light chain-heavy chain pair" refers to the collection of a light chain and heavy chain that can form a dimer through a disulfide bond between the CL domain of the light chain and the CH1 domain of the heavy chain.

As previously indicated, the subunit structures and three dimensional configuration of the constant regions of the various immunoglobulin classes are well known. As used herein, the term "VH domain" includes the amino terminal variable domain of an immunoglobulin heavy chain and the term "CH1 domain" includes the first (most amino terminal) constant region domain of an immunoglobulin heavy chain. The CH1 domain is adjacent to the VH domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat et al., U.S. Dept. of Health and Human Services, "Sequences of Proteins of Immunological Interest" (1983). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen-binding regions to move independently. Hinge regions can be subdivided into three distinct domains: upper, middle, and lower hinge domains (Roux et al., *J. Immunol* 161:4083 (1998)).

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CK regions are linked by a disulfide bond and the two heavy chains are linked by two disulfide bonds at positions corresponding to 239 and 242 using the Kabat numbering system (position 226 or 229, EU numbering system).

As used herein, the term "chimeric antibody" will be held to mean any antibody wherein the immunoreactive region or site is obtained or derived from a first species and the constant region (which may be intact, partial or modified in accordance with the instant disclosure) is obtained from a second species. In certain embodiments the target binding region or site will be from a non-human source (e.g. mouse or primate) and the constant region is human.

As used herein, "percent humanization" is calculated by determining the number of framework amino acid differences (i.e., non-CDR difference) between the humanized domain and the germline domain, subtracting that number from the total number of amino acids, and then dividing that by the total number of amino acids and multiplying by 100.

By "specifically binds" or "has specificity to," it is generally meant that an antibody binds to an epitope via its antigen-binding domain, and that the binding entails some complementarity between the antigen-binding domain and the epitope. According to this definition, an antibody is said to "specifically bind" to an epitope when it binds to that epitope, via its antigen-binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

As used herein, the terms "treat" or "treatment" refer to both therapeutic treatment and prophylactic or preventative measures, wherein the object is to prevent or slow down (lessen) an undesired physiological change or disorder, such as the progression of cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sport, or pet animals such as dogs, cats, guinea pigs, rabbits, rats, mice, horses, cattle, cows, and so on.

As used herein, phrases such as "to a patient in need of treatment" or "a subject in need of treatment" includes subjects, such as mammalian subjects, that would benefit from administration of an antibody or composition of the present disclosure used, e.g., for detection, for a diagnostic procedure and/or for treatment.

Anti-CD73 Antibodies

The present disclosure provides anti-CD73 antibodies with high affinity and inhibitory activity on the human CD73 protein. The antibodies can bind effectively to both free CD73 and CD73 on cell surfaces. Once bound to a CD73 protein on the cell surface, the binding can trigger internalization, resulting in reduction of cell surface expression of the CD73 protein which reduces extracellular adenosine and the immunosuppressive tumor environment. Further, as these antibodies do not compete with the AMP substrate in binding to the active site of CD73 but act allosterically or through other non-competitive mechanisms, these antibodies do not interfere with CD73 binding with these endogenous AMP substrates, which limits potential adverse effects of these antibodies.

In addition, as demonstrated in the experimental examples, these antibodies exhibited a few unique properties not observed with known anti-CD73 antibodies, such as MEDI-9447 from Medimmune. As shown in Example 12, while MEDI-9447 and 11F11 bind to the N-terminal domains of the CD73 protein, the target amino acids of the present antibodies (e.g., Y345, D399, E400, R401 and R480) are in the C-terminal domains.

The CD73 enzyme consists of a dimer of two identical 70-kD subunits bound by a glycosyl phosphatidyl inositol linkage to the external face of the plasma membrane. Crystal structures of the dimeric human CD73 reveal an extensive conformational switch between an open and closed forms of the enzyme, which is required for proper functioning of the enzyme. The dimerization interface is formed by the C-terminal domains. When the C-terminal domains are involved in other bindings, it is contemplated, the dimerization and/or the conformational switch will be blocked resulting in inhibition of CD73 activity. Binding to an antibody by the N-terminal domains, by contrast, might not have such effects.

Therefore, it is contemplated that when the presently disclosed antibodies bind the CD73 protein at its C-terminal domains, they will block the dimerization of the protein and effectively inhibit its activity. The presently disclosed antibodies, therefore, are much superior to the previously known anti-CD73 antibodies, which bind to the N-terminal domains.

In accordance with one embodiment of the present disclosure, therefore, provided is an isolated antibody or fragment thereof which has specificity to a human CD73 protein and binds to one or more amino acid residues selected from the C-terminal portion of the human CD73 protein. The C-terminal portion of the human CD73 protein, as known in the art, includes 238 amino acid residues starting from residue 337, as shown in SEQ ID NO: 61 in the table below.

TABLE A

CD73 Sequence:

| Name | Sequence (SEQ ID NO: 61; C-terminal portion underlined and bold) |
|---|---|
| Human CD73 protein | MCPRAARAPATLLLALGAVLWPAAGAWELTILHTNDVHSR LEQTSEDSSKCVNASRCMGGVARLFTKVQQIRRAEPNVLL LDAGDQYQGTIWFTVYKGAEVAHFMNALRYDAMALGNHEF DNGVEGLIEPLLKEAKFPILSANIKAKGPLASQISGLYLP YKVLPVGDEVVGIVGYTSKETPFLSNPGTNLVFEDEITAL QPEVDKLKTLNVNKIIALGHSGFEMDKLIAQKVRGVDVVV GGHSNTFLYTGNPPSKEVPAGKYPFIVTSDDGRKVPVVQA YAFGKYLGYLKIEFDERGNVISSHGNPILLNSSIPEDPSI KADINKWRIKLDNYSTQELGKTIVYLDGSSQSCRFRECNM GNLICDAMINNNLRHTDEMFWNHVSMCILNGGGIRSPIDE RNNGTITWENLAAVLPFGGTFDLVQLKGSTLKKAFEHSVH RYGQSTGEFLQVGGIHVVYDLSRKPGDRVVKLDVLCTKCR VPSYDPLKMDEVYKVILPNFLANGGDGFQMIKDELLRHDS GDQDINVVSTYISKMYVIYPAVEGRIKFSTGSHCHGSFSL IFLSLWAVIFVLYQ |

In some embodiments, the antibody or fragment thereof binds to one or more of the C-terminal domains of the human CD73 protein. In some embodiments, the antibody or fragment thereof binds to at least one of amino acid residues selected the group consisting of Y345, D399, E400, R401 and R480 of the human CD73 protein. In some embodiments, the antibody or fragment thereof binds to at least two of the amino acid residues.

In some embodiments, the antibody or fragment thereof binds to at least Y345 and D399. In some embodiments, the antibody or fragment thereof binds to at least Y345 and E400. In some embodiments, the antibody or fragment thereof binds to at least Y345 and R401. In some embodiments, the antibody or fragment thereof binds to at least Y345 and R480. In some embodiments, the antibody or fragment thereof binds to at least D399 and E400. In some embodiments, the antibody or fragment thereof binds to at least D399 and R401. In some embodiments, the antibody or fragment thereof binds to at least D399 and R480. In some embodiments, the antibody or fragment thereof binds to at least E400 and R401. In some embodiments, the antibody or fragment thereof binds to at least E400 and R480. In some embodiments, the antibody or fragment thereof binds to at least R401 and R480.

In some embodiments, the antibody or fragment thereof binds to at least Y345, D399, and E400. In some embodiments, the antibody or fragment thereof binds to at least Y345, D399, and R401. In some embodiments, the antibody or fragment thereof binds to at least Y345, D399, and R480. In some embodiments, the antibody or fragment thereof binds to at least Y345, E400, and R401. In some embodiments, the antibody or fragment thereof binds to at least Y345, E400, and R480. In some embodiments, the antibody or fragment thereof binds to at least Y345, R401 and R480. In some embodiments, the antibody or fragment thereof binds to at least D399, E400, and R401. In some embodiments, the antibody or fragment thereof binds to at least D399, E400, and R480. In some embodiments, the antibody or fragment thereof binds to at least E400, R401 and R480.

In some embodiments, the antibody or fragment thereof binds to at least Y345, D399, E400, and R401. In some embodiments, the antibody or fragment thereof binds to at least Y345, D399, E400, and R480. In some embodiments, the antibody or fragment thereof binds to at least Y345, D399, R401 and R480. In some embodiments, the antibody or fragment thereof binds to at least Y345, E400, R401 and R480. In some embodiments, the antibody or fragment thereof binds to at least D399, E400, R401 and R480. In some embodiments, the antibody or fragment thereof binds to each of Y345, D399, E400, R401 and R480.

In accordance with one embodiment of the present disclosure, provided is an antibody that includes the heavy chain and light chain variable domains with the CDR regions as defined in SEQ ID NO: 1-6.

TABLE 1

Sequences of the CDR regions

| Name | Sequences | SEQ ID NO: |
|---|---|---|
| VH CDR1 | SGYYWN | 1 |
| VH CDR2 | YINYGGSNGYNPSLKS | 2 |
| VH CDR3 | DYDAYYEALDD | 3 |
| VL CDR1 | RASSRVNYMH | 4 |
| VL CDR2 | ATSNLAS | 5 |
| VL CDR3 | QQWSSNPPT | 6 |

As demonstrated in the experimental examples, the antibodies that contained these CDR regions, whether mouse, humanized or chimeric, had potent CD73 binding and inhibitory activities. Further computer modeling indicated that certain residues within the CDR can be modified to retain or improve the property of the antibodies. Such residues are referred to as "hot spots" which are underlined in Table 1. In some embodiments, an anti-CD73 antibody of the present disclosure includes the VH and VL CDR as listed in Table 1, with one, two or three further modifications. Such modifications can be addition, deletion or substitution of amino acids.

In some embodiments, the modification is substitution at no more than one hot spot position from each of the CDRs. In some embodiments, the modification is substitution at one, two or three such hot spot positions. In one embodiment, the modification is substitution at one of the hot spot positions. Such substitutions, in some embodiments, are conservative substitutions.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in an immunoglobulin polypeptide is preferably replaced with another amino acid residue from the same side chain family. In another embodiment, a string of amino acids can be replaced with a structurally similar string that differs in order and/or composition of side chain family members.

Non-limiting examples of conservative amino acid substitutions are provided in the table below, where a similarity score of 0 or higher indicates conservative substitution between the two amino acids.

TABLE 2

Amino Acid Similarity Matrix

|   | C | G | P | S | A | T | D | E | N | Q | H | K | R | V | M | I | L | F | Y | W |
|---|---|---|---|---|---|---|---|---|---|---|---|---|---|---|---|---|---|---|---|---|
| W | −8 | −7 | −6 | −2 | −6 | −5 | −7 | −7 | −4 | −5 | −3 | −3 | 2 | −6 | −4 | −5 | −2 | 0 | 0 | 17 |
| Y | 0 | −5 | −5 | −3 | −3 | −3 | −4 | −4 | −2 | −4 | 0 | −4 | −5 | −2 | −2 | −1 | −1 | 7 | 10 | |
| F | −4 | −5 | −5 | −3 | −4 | −3 | −6 | −5 | −4 | −5 | −2 | −5 | −4 | −1 | 0 | 1 | 2 | 9 | | |
| L | −6 | −4 | −3 | −3 | −2 | −2 | −4 | −3 | −3 | −2 | −2 | −3 | −3 | 2 | 4 | 2 | 6 | | | |
| I | −2 | −3 | −2 | −1 | −1 | 0 | −2 | −2 | −2 | −2 | −2 | −2 | −2 | 4 | 2 | 5 | | | | |
| M | −5 | −3 | −2 | −2 | −1 | −1 | −3 | −2 | 0 | −1 | −2 | 0 | 0 | 2 | 6 | | | | | |
| V | −2 | −1 | −1 | −1 | 0 | 0 | −2 | −2 | −2 | −2 | −2 | −2 | −2 | 4 | | | | | | |
| R | −4 | −3 | 0 | 0 | −2 | −1 | −1 | −1 | 0 | 1 | 2 | 3 | 6 | | | | | | | |
| K | −5 | −2 | −1 | 0 | −1 | 0 | 0 | 0 | 1 | 1 | 0 | 5 | | | | | | | | |
| H | −3 | −2 | 0 | −1 | −1 | −1 | 1 | 1 | 2 | 3 | 6 | | | | | | | | | |
| Q | −5 | −1 | 0 | −1 | 0 | −1 | 2 | 2 | 1 | 4 | | | | | | | | | | |
| N | −4 | 0 | −1 | 1 | 0 | 0 | 2 | 1 | 2 | | | | | | | | | | | |
| E | −5 | 0 | −1 | 0 | 0 | 0 | 3 | 4 | | | | | | | | | | | | |
| D | −5 | 1 | −1 | 0 | 0 | 0 | 4 | | | | | | | | | | | | | |
| T | −2 | 0 | 0 | 1 | 1 | 3 | | | | | | | | | | | | | | |
| A | −2 | 1 | 1 | 1 | 2 | | | | | | | | | | | | | | | |
| S | 0 | 1 | 1 | 1 | | | | | | | | | | | | | | | | |
| P | −3 | −1 | 6 | | | | | | | | | | | | | | | | | |
| G | −3 | 5 | | | | | | | | | | | | | | | | | | |
| C | 12 | | | | | | | | | | | | | | | | | | | |

TABLE 3

Conservative Amino Acid Substitutions

| For Amino Acid | Substitution With |
|---|---|
| Alanine | D-Ala, Gly, Aib, β-Ala, L-Cys, D-Cys |
| Arginine | D-Arg, Lys, D-Lys, Orn D-Orn |
| Asparagine | D-Asn, Asp, D-Asp, Glu, D-Glu, Gln, D-Gln |
| Aspartic Acid | D-Asp, D-Asn, Asn, Glu, D-Glu, Gln, D-Gln |
| Cysteine | D-Cys, S-Me-Cys, Met, D-Met, Thr, D-Thr, L-Ser, D-Ser |
| Glutamine | D-Gln, Asn, D-Asn, Glu, D-Glu, Asp, D-Asp |
| Glutamic Acid | D-Glu, D-Asp, Asp, Asn, D-Asn, Gln, D-Gln |
| Glycine | Ala, D-Ala, Pro, D-Pro, Aib, β-Ala |
| Isoleucine | D-Ile, Val, D-Val, Leu, D-Leu, Met, D-Met |
| Leucine | Val, D-Val, Met, D-Met, D-Ile, D-Leu, Ile |
| Lysine | D-Lys, Arg, D-Arg, Orn, D-Orn |
| Methionine | D-Met, S-Me-Cys, Ile, D-Ile, Leu, D-Leu, Val, D-Val |

TABLE 3-continued

Conservative Amino Acid Substitutions

| For Amino Acid | Substitution With |
|---|---|
| Phenylalanine | D-Phe, Tyr, D-Tyr, His, D-His, Trp, D-Trp |
| Proline | D-Pro |
| Serine | D-Ser, Thr, D-Thr, allo-Thr, L-Cys, D-Cys |
| Threonine | D-Thr, Ser, D-Ser, allo-Thr, Met, D-Met, Val, D-Val |
| Tyrosine | D-Tyr, Phe, D-Phe, His, D-His, Trp, D-Trp |
| Valine | D-Val, Leu, D-Leu, Ile, D-Ile, Met, D-Met |

Specific examples of CDRs with suitable substitutions are provided in SEQ ID NO: 26-56 of Example 7. In some embodiments, therefore, an antibody of the present disclosure includes a VH CDR1 of SEQ ID NO: 1 or any one of 26-29. In some embodiments, an antibody of the present disclosure includes a VH CDR2 of SEQ ID NO: 2 or any one of 30-36. In some embodiments, an antibody of the present disclosure includes a VH CDR3 of SEQ ID NO: 1 or any one of 37-41. In some embodiments, an antibody of the present disclosure includes a VL CDR1 of SEQ ID NO: 4 or any one of 42-45. In some embodiments, an antibody of the present disclosure includes a VL CDR2 of SEQ ID NO: 5. In some embodiments, an antibody of the present disclosure includes a VL CDR3 of SEQ ID NO: 6 or any one of 46-56.

In some embodiments, an antibody or fragment thereof includes no more than one, no more than two, or no more than three of the above substitutions. In some embodiments, the antibody or fragment thereof includes a VH CDR1 of SEQ ID NO: 1 or any one of SEQ ID NO: 26-29, a VH CDR2 of SEQ ID NO: 2, a VH CDR3 of SEQ ID NO: 3, a VL CDR1 of SEQ ID NO: 4, a VL CDR2 of SEQ ID NO: 5, and a VL CDR3 of SEQ ID NO: 6.

In some embodiments, the antibody or fragment thereof includes a VH CDR1 of SEQ ID NO: 1, a VH CDR2 of SEQ ID NO: 2 or any one of SEQ ID NO: 30-36, a VH CDR3 of SEQ ID NO: 3, a VL CDR1 of SEQ ID NO: 4, a VL CDR2 of SEQ ID NO: 5, and a VL CDR3 of SEQ ID NO: 6.

In some embodiments, the antibody or fragment thereof includes a VH CDR1 of SEQ ID NO: 1, a VH CDR2 of SEQ ID NO: 2, a VH CDR3 of SEQ ID NO: 3 or any one of SEQ ID NO: 37-41, a VL CDR1 of SEQ ID NO: 4, a VL CDR2 of SEQ ID NO: 5, and a VL CDR3 of SEQ ID NO: 6.

In some embodiments, the antibody or fragment thereof includes a VH CDR1 of SEQ ID NO: 1, a VH CDR2 of SEQ ID NO: 2, a VH CDR3 of SEQ ID NO: 3, a VL CDR1 of SEQ ID NO: 4 or any one of SEQ ID NO: 42-45, a VL CDR2 of SEQ ID NO: 5, and a VL CDR3 of SEQ ID NO: 6.

In some embodiments, the antibody or fragment thereof includes a VH CDR1 of SEQ ID NO: 1, a VH CDR2 of SEQ ID NO: 2, a VH CDR3 of SEQ ID NO: 3, a VL CDR1 of SEQ ID NO: 4, a VL CDR2 of SEQ ID NO: 5, and a VL CDR3 of SEQ ID NO: 6 or any one of SEQ ID NO: 46-56.

Non-limiting examples of VH are provided in SEQ ID NO: 7 and 9-13, out of which SEQ ID NO: 10 is the mouse VH, and SEQ ID NO: 7, 9, and 11-13 are humanized ones. Further, among the humanized VH, SEQ ID NO: 7, 9 and 12-13 include one or more back-mutations to the mouse version. Likewise, non-limiting examples of VL (VK) are provided in SEQ ID NO: 8, 15-20 and 22-24. SEQ ID NO: 15 is a mouse sequence, SEQ ID NO: 16 and 22 are the originally derived humanized sequences as shown in the examples. SEQ ID NO: 8, 17-20 and 22-24 are humanized VL with back-mutations.

The back-mutations are shown to be useful for retaining certain characteristics of the anti-CD73 antibodies. Accordingly, in some embodiments, the anti-CD73 antibodies of the present disclosure, in particular the human or humanized ones, include one or more of the back-mutations. In some embodiments, the VH back-mutation (i.e., included amino acid at the specified position) is one or more selected from (a) Thr at position 30, (b) Lys at position 44, (c) Met at position 48, (d) Ile at position 67, and (e) Arg at position 71, according to Kabat numbering, and combinations thereof. In some embodiments, the VL back-mutation is one or more selected from (a) Ser at position 5, (b) Pro at position 46, (c) Trp at position 47, (d) Ser at position 49, (e) Ser at position 70, and (f) Tyr at position 71, according to Kabat numbering, and combinations thereof.

In some embodiments, the anti-CD73 antibody of the present disclosure includes a VH of SEQ ID NO: 7, or any one of 9-13, a VL of SEQ NO: 8, or any one of 15-20 and 22-24, or their respective biological equivalents. A biological equivalent of a VH or VL is a sequence that includes the designated amino acids while having an overall 80%, 85%, 90%, 95%, 98% or 99% sequence identity. A biological equivalent of SEQ ID NO: 7, therefore, can be a VH that has an overall 80%, 85%, 90%, 95%, 98% or 99% sequence identity to SEQ ID NO: 7 but retains the CDRs (SEQ ID NO: 1-6 or their variants), and optionally retains one or more, or all of the back-mutations.

In one embodiment, the VH has the amino acid sequence of SEQ ID NO: 7 and the VL has the amino acid sequence of SEQ ID NO: 8. In one embodiment, the VH has the amino acid sequence of SEQ ID NO: 9 and the VL has the amino acid sequence of SEQ ID NO: 8.

It will also be understood by one of ordinary skill in the art that antibodies as disclosed herein may be modified such that they vary in amino acid sequence from the naturally occurring binding polypeptide from which they were derived. For example, a polypeptide or amino acid sequence derived from a designated protein may be similar, e.g., have a certain percent identity to the starting sequence, e.g., it may be 60%, 70%, 75%, 80%, 85%, 90%, 95%, 98%, or 99% identical to the starting sequence.

In certain embodiments, the antibody comprises an amino acid sequence or one or more moieties not normally associated with an antibody. Exemplary modifications are described in more detail below. For example, an antibody of the disclosure may comprise a flexible linker sequence, or may be modified to add a functional moiety (e.g., PEG, a drug, a toxin, or a label).

Antibodies, variants, or derivatives thereof of the disclosure include derivatives that are modified, i.e., by the covalent attachment of any type of molecule to the antibody such that covalent attachment does not prevent the antibody from binding to the epitope. For example, but not by way of limitation, the antibodies can be modified, e.g., by glycosylation, acetylation, pegylation, phosphorylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the antibodies may contain one or more non-classical amino acids.

In some embodiments, the antibodies may be conjugated to therapeutic agents, prodrugs, peptides, proteins, enzymes, viruses, lipids, biological response modifiers, pharmaceutical agents, or PEG.

The antibodies may be conjugated or fused to a therapeutic agent, which may include detectable labels such as radioactive labels, an immunomodulator, a hormone, an enzyme, an oligonucleotide, a photoactive therapeutic or diagnostic agent, a cytotoxic agent, which may be a drug or a toxin, an ultrasound enhancing agent, a non-radioactive label, a combination thereof and other such agents known in the art.

The antibodies can be detectably labeled by coupling it to a chemiluminescent compound. The presence of the chemiluminescent-tagged antigen-binding polypeptide is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

The antibodies can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA). Techniques for conjugating various moieties to an antibody are well known, see, e.g., Arnon et al., "Monoclonal Antibodies For Immunotargeting Of Drugs in Cancer Therapy", in Monoclonal Antibodies And Cancer Therapy, Reisfeld et al. (eds.), pp. 243-56 (Alan R. Liss, Inc. (1985); Hellstrom et al., "Antibodies For Drug Delivery", in Controlled Drug Delivery (2nd Ed.), Robinson et al., (eds.), Marcel Dekker, Inc., pp. 623-53 (1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), Academic Press pp. 303-16 (1985), and Thorpe et al., "The Preparation And Cytotoxic Properties Of Antibody-Toxin Conjugates", Immunol. Rev. (52:119-58 (1982)).

Polynucleotides Encoding the Antibodies and Methods of Preparing the Antibodies

The present disclosure also provides isolated polynucleotides or nucleic acid molecules encoding the antibodies, variants or derivatives thereof of the disclosure. Examples of polynucleotides include SEQ ID NO: 57-60. The polynucleotides of the present disclosure may encode the entire heavy and light chain variable regions of the antigen-binding polypeptides, variants or derivatives thereof on the same polynucleotide molecule or on separate polynucleotide molecules. Additionally, the polynucleotides of the present disclosure may encode portions of the heavy and light chain variable regions of the antigen-binding polypeptides, variants or derivatives thereof on the same polynucleotide molecule or on separate polynucleotide molecules.

Methods of making antibodies are well known in the art and described herein. In certain embodiments, both the variable and constant regions of the antigen-binding polypeptides of the present disclosure are fully human. Fully human antibodies can be made using techniques described in the art and as described herein. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to make such antibodies are described in U.S. Pat. Nos. 6,150,584; 6,458,592; 6,420,140 which are incorporated by reference in their entireties.

In certain embodiments, the prepared antibodies will not elicit a deleterious immune response in the animal to be treated, e.g., in a human. In one embodiment, antigen-binding polypeptides, variants, or derivatives thereof of the disclosure are modified to reduce their immunogenicity using art-recognized techniques. For example, antibodies can be humanized, primatized, deimmunized, or chimeric antibodies can be made. These types of antibodies are derived from a non-human antibody, typically a murine or primate antibody, that retains or substantially retains the antigen-binding properties of the parent antibody, but which is less immunogenic in humans. This may be achieved by various methods, including (a) grafting the entire non-human variable domains onto human constant regions to generate chimeric antibodies; (b) grafting at least a part of one or more of the non-human complementarity determining regions (CDRs) into a human framework and constant regions with or without retention of critical framework residues; or (c) transplanting the entire non-human variable domains, but "cloaking" them with a human-like section by replacement of surface residues. Such methods are disclosed in Morrison et al., Proc. Natl. Acad. Sci. USA 57:6851-6855 (1984); Morrison et al., Adv. Immunol. 44:65-92 (1988); Verhoeyen et al., Science 239:1534-1536 (1988); Padlan, Molec. Immun. 25:489-498 (1991); Padlan, Molec. Immun. 31:169-217 (1994), and U.S. Pat. Nos. 5,585,089, 5,693,761, 5,693,762, and 6,190,370, all of which are hereby incorporated by reference in their entirety.

De-immunization can also be used to decrease the immunogenicity of an antibody. As used herein, the term "de-immunization" includes alteration of an antibody to modify T-cell epitopes (see. e.g., International Application Publication Nos.: WO/9852976 A1 and WO/0034317 A2). For example, variable heavy chain and variable light chain sequences from the starting antibody are analyzed and a human T-cell epitope "map" from each V region showing the location of epitopes in relation to complementarity-determining regions (CDRs) and other key residues within the sequence is created. Individual T-cell epitopes from the T-cell epitope map are analyzed in order to identify alternative amino acid substitutions with a low risk of altering activity of the final antibody. A range of alternative variable heavy and variable light sequences are designed comprising combinations of amino acid substitutions and these sequences are subsequently incorporated into a range of binding polypeptides. Typically, between 12 and 24 variant antibodies are generated and tested for binding and/or function. Complete heavy and light chain genes comprising modified variable and human constant regions are then cloned into expression vectors and the subsequent plasmids introduced into cell lines for the production of whole antibody. The antibodies are then compared in appropriate biochemical and biological assays, and the optimal variant is identified.

The binding specificity of antigen-binding polypeptides of the present disclosure can be determined by in vitro assays such as immunoprecipitation, radioimmunoassay (RIA) or enzyme-linked immunoabsorbent assay (ELISA).

Alternatively, techniques described for the production of single-chain units (U.S. Pat. No. 4,694,778; Bird, Science 242:423-442 (1988); Huston et al., Proc. Natl. Acad. Sci. USA 55:5879-5883 (1988); and Ward et al., Nature 334:544-554 (1989)) can be adapted to produce single-chain units of the present disclosure. Single-chain units are formed by linking the heavy and light chain fragments of the Fv region via an amino acid bridge, resulting in a single-chain fusion peptide. Techniques for the assembly of functional Fv fragments in *E. coli* may also be used (Skerra et al., *Science* 242: 1038-1041 (1988)).

Examples of techniques which can be used to produce single-chain Fvs (scFvs) and antibodies include those described in U.S. Pat. Nos. 4,946,778 and 5,258,498; Huston et al., *Methods in Enzymology* 203:46-88 (1991); Shu et al., *Proc. Natl. Sci. USA* 90:1995-1999 (1993); and Skerra et al., *Science* 240:1038-1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See, e.g., Morrison, *Science* 229:1202 (1985); Oi et al., *BioTechniques* 4:214 (1986); Gillies et al., *J. Immunol. Methods* 125:191-202 (1989); U.S. Pat. Nos. 5,807,715; 4,816,567; and 4,816397, which are incorporated herein by reference in their entireties.

Humanized antibodies are antibody molecules derived from a non-human species antibody that bind the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, preferably improve, antigen-binding. These framework substitutions are identified by methods well known in the art, e.g., by modeling of the interactions of the CDR and framework residues to identify framework residues important for antigen-binding and sequence comparison to identify unusual framework residues at particular positions. (See, e.g., Queen et al., U.S. Pat. No. 5,585,089; Riechmann et al., *Nature* 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, *Molecular Immunology* 28(4/5):489-498 (1991); Studnicka et al., *Protein Engineering* 7(6):805-814 (1994); Roguska et al., *Proc. Natl. Sci. USA* 91:969-973 (1994)), and chain shuffling (U.S. Pat. No. 5,565,332, which is incorporated by reference in its entirety).

Completely human antibodies are particularly desirable for therapeutic treatment of human patients. Human antibodies can be made by a variety of methods known in the art including phage display methods using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring that express human antibodies. The transgenic mice are immunized in the normal fashion with a selected antigen, e.g., all or a portion of a desired target polypeptide. Monoclonal antibodies directed against the antigen can be obtained from the immunized, transgenic mice using conventional hybridoma technology. The human immunoglobulin transgenes harbored by the transgenic mice rearrange during B-cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar *Int. Rev. Immunol.* 73:65-93 (1995). For a detailed discussion of this technology for producing human antibodies and human monoclonal antibodies and protocols for producing such antibodies, see, e.g., PCT publications WO 98/24893; WO 96/34096; WO 96/33735; U.S. Pat. Nos. 5,413,923; 5,625,126; 5,633,425; 5,569,825; 5,661,016; 5,545,806; 5,814,318; and 5,939,598, which are incorporated by reference herein in their entirety. In addition, companies such as Abgenix, Inc. (Freemont, Calif.) and GenPharm (San Jose, Calif.) can be engaged to provide human antibodies directed against a selected antigen using technology similar to that described above.

Completely human antibodies which recognize a selected epitope can also be generated using a technique referred to as "guided selection." In this approach a selected non-human monoclonal antibody, e.g., a mouse antibody, is used to guide the selection of a completely human antibody recognizing the same epitope (Jespers et al., *Bio/Technology* 72:899-903 (1988). See also, U.S. Pat. No. 5,565,332, which is incorporated by reference in its entirety.)

In another embodiment, DNA encoding desired monoclonal antibodies may be readily isolated and sequenced using conventional procedures (e.g., by using oligonucleotide probes that are capable of binding specifically to genes encoding the heavy and light chains of murine antibodies). The isolated and subcloned hybridoma cells serve as a preferred source of such DNA. Once isolated, the DNA may be placed into expression vectors, which are then transfected into prokaryotic or eukaryotic host cells such as *E. coli* cells, simian COS cells. Chinese Hamster Ovary (CHO) cells or myeloma cells that do not otherwise produce immunoglobulins. More particularly, the isolated DNA (which may be synthetic as described herein) may be used to clone constant and variable region sequences for the manufacture antibodies as described in Newman et al., U.S. Pat. No. 5,658,570, filed Jan. 25, 1995, which is incorporated by reference herein. Essentially, this entails extraction of RNA from the selected cells, conversion to cDNA, and amplification by PCR using Ig specific primers. Suitable primers for this purpose are also described in U.S. Pat. No. 5,658,570. As will be discussed in more detail below, transformed cells expressing the desired antibody may be grown up in relatively large quantities to provide clinical and commercial supplies of the immunoglobulin.

Additionally, using routine recombinant DNA techniques, one or more of the CDRs of the antigen-binding polypeptides of the present disclosure, may be inserted within framework regions, e.g., into human framework regions to humanize a non-human antibody. The framework regions may be naturally occurring or consensus framework regions, and preferably human framework regions (see, e.g., Chothia et al., *J. Mol. Biol.* 278:457-479 (1998) for a listing of human framework regions). Preferably, the polynucleotide generated by the combination of the framework regions and CDRs encodes an antibody that specifically binds to at least one epitope of a desired polypeptide, e.g., LIGHT. Preferably, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present disclosure and within the skill of the art.

In addition, techniques developed for the production of "chimeric antibodies" (Morrison et al., *Proc. Natl. Acad. Sci. USA:* 851-855 (1984); Neuberger et al., *Nature* 372:604-608 (1984); Takeda et al., *Nature* 314:452-454 (1985)) by splicing genes from a mouse antibody molecule, of appropriate antigen specificity, together with genes from a human antibody molecule of appropriate biological activity can be used. As used herein, a chimeric antibody is a molecule in which different portions are derived from different animal species, such as those having a variable region derived from a murine monoclonal antibody and a human immunoglobulin constant region.

Yet another highly efficient means for generating recombinant antibodies is disclosed by Newman, *Biotechnology* 10: 1455-1460 (1992). Specifically, this technique results in the generation of primatized antibodies that contain monkey variable domains and human constant sequences. This reference is incorporated by reference in its entirety herein. Moreover, this technique is also described in commonly assigned U.S. Pat. Nos. 5,658,570, 5,693,780 and 5,756,096 each of which is incorporated herein by reference.

Alternatively, antibody-producing cell lines may be selected and cultured using techniques well known to the skilled artisan. Such techniques are described in a variety of laboratory manuals and primary publications. In this respect, techniques suitable for use in the disclosure as described below are described in *Current Protocols in Immunology*, Coligan et al., Eds., Green Publishing Associates and Wiley-Interscience, John Wiley and Sons, New York (1991) which is herein incorporated by reference in its entirety, including supplements.

Additionally, standard techniques known to those of skill in the art can be used to introduce mutations in the nucleotide sequence encoding an antibody of the present disclosure, including, but not limited to, site-directed mutagenesis and PCR-mediated mutagenesis which result in amino acid substitutions. Preferably, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference variable heavy chain region, CDR-H1, CDR-H2, CDR-H3, variable light chain region, CDR-L1, CDR-L2, or CDR-L3. Alternatively, mutations can be introduced randomly along all or part of the coding sequence, such as by saturation mutagenesis, and the resultant mutants can be screened for biological activity to identify mutants that retain activity.

Treatment Methods

As described herein, the antibodies, variants or derivatives of the present disclosure may be used in certain treatment and diagnostic methods.

The present disclosure is further directed to antibody-based therapies which involve administering the antibodies of the disclosure to a patient such as an animal, a mammal, and a human for treating one or more of the disorders or conditions described herein. Therapeutic compounds of the disclosure include, but are not limited to, antibodies of the disclosure (including variants and derivatives thereof as described herein) and nucleic acids or polynucleotides encoding antibodies of the disclosure (including variants and derivatives thereof as described herein).

The antibodies of the disclosure can also be used to treat or inhibit cancer. As provided above, CD73 can be overexpressed in tumor cells. Tumor-derived CD73 can function as an ecto-enzyme to produce extracellular adenosine, which promotes tumor growth by limiting antitumor T-cell immunity via adenosine receptor signaling. Results with small molecule inhibitors, or monoclonal antibodies targeting CD73 in murine tumor models, indicate that targeted CD73 therapy is an important alternative and realistic approach to effective control of tumor growth. In particular, it helps T-cell-based therapy by enhancing the adaptive immune response machinery, which may increase the function of tumor-infiltrating T lymphocytes, and lead to improved survival in cancer patients.

Accordingly, in some embodiments, provided are methods for treating a cancer in a patient in need thereof. The method, in one embodiment, entails administering to the patient an effective amount of an antibody of the present disclosure. In some embodiments, at least one of the cancer cells (e.g., stromal cells) in the patient over-express CD73.

Non-limiting examples of cancers include bladder cancer, breast cancer, colorectal cancer, endometrial cancer, esophageal cancer, head and neck cancer, kidney cancer, leukemia, liver cancer, lung cancer, lymphoma, melanoma, pancreatic cancer, prostate cancer, and thyroid cancer.

Cellular therapies, and more specifically chimeric antigen receptor (CAR) T-cell therapies, are also provided in the present disclosure. A suitable T cell can be used, that is put in contact with an anti-CD73 antibody of the present disclosure (or alternatively engineered to express an anti-CD73 antibody of the present disclosure). Upon such contact or engineering, the T cell can then be introduced to a cancer patient in need of a treatment. The cancer patient may have a cancer of any of the types as disclosed herein. The T cell can be, for instance, a tumor-infiltrating T lymphocyte, a CD4+ T cell, a CD8+ T cell, or the combination thereof, without limitation.

In some embodiments, the T cell was isolated from the cancer patient him- or her-self. In some embodiments, the T cell was provided by a donor or from a cell bank. When the T cell is isolated from the cancer patient, undesired immune reactions can be minimized.

Additional diseases or conditions associated with increased cell survival, that may be treated, prevented, diagnosed and/or prognosed with the antibodies or variants, or derivatives thereof of the disclosure include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma and retinoblastoma.

A specific dosage and treatment regimen for any particular patient will depend upon a variety of factors, including the particular antibodies, variant or derivative thereof used, the patient's age, body weight, general health, sex, and diet, and the time of administration, rate of excretion, drug combination, and the severity of the particular disease being treated. Judgment of such factors by medical caregivers is within the ordinary skill in the art. The amount will also depend on the individual patient to be treated, the route of administration, the type of formulation, the characteristics of the compound used, the severity of the disease, and the desired effect. The amount used can be determined by pharmacological and pharmacokinetic principles well known in the art.

Methods of administration of the antibodies, variants or include but are not limited to intradermal, intramuscular, intraperitoneal, intravenous, subcutaneous, intranasal, epidural, and oral routes. The antigen-binding polypeptides or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Thus, pharmaceutical compositions containing the antigen-binding polypeptides of the disclosure may be administered orally, rectally, parenterally, intracisternally, intravaginally, intraperitoneally, topically (as by powders, ointments, drops or transdermal patch), bucally, or as an oral or nasal spray.

The term "parenteral" as used herein refers to modes of administration which include intravenous, intramuscular, intraperitoneal, intrasternal, subcutaneous and intra-articular injection and infusion.

Administration can be systemic or local. In addition, it may be desirable to introduce the antibodies of the disclosure into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

It may be desirable to administer the antigen-binding polypeptides or compositions of the disclosure locally to the area in need of treatment; this may be achieved by, for example, and not by way of limitation, local infusion during surgery, topical application, e.g., in conjunction, with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the disclosure, care must be taken to use materials to which the protein does not absorb.

In another embodiment, the antigen-binding polypeptide or composition can be delivered in a vesicle, in particular a liposome (see Langer, 1990, Science 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the antigen-binding polypeptide or composition can be delivered in a controlled release system. In one embodiment, a pump may be used (see Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., 1983, Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In yet another embodiment, a controlled release system can be placed in proximity of the therapeutic target, i.e., the brain, thus requiring only a fraction of the systemic dose (see, e.g., Goodson, in Medical Applications of Controlled Release, supra. vol. 2, pp. 115-138 (1984)). Other controlled release systems are discussed in the review by Langer (1990, Science 249:1527-1533).

In a specific embodiment where the composition of the disclosure comprises a nucleic acid or polynucleotide encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see, e.g., Joliot et al., 1991, Proc. Natl. Acad. Sci. USA 88:1864-1868), etc. Alternatively, a nucleic acid can be introduced intracellularly and incorporated within host cell DNA for expression, by homologous recombination.

The amount of the antibodies of the disclosure which will be effective in the treatment, inhibition and prevention of an inflammatory, immune or malignant disease, disorder or condition can be determined by standard clinical techniques. In addition, in vitro assays may optionally be employed to help identify optimal dosage ranges. The precise dose to be employed in the formulation will also depend on the route of administration, and the seriousness of the disease, disorder or condition, and should be decided according to the judgment of the practitioner and each patient's circumstances. Effective doses may be extrapolated from dose-response curves derived from in vitro or animal model test systems.

As a general proposition, the dosage administered to a patient of the antigen-binding polypeptides of the present disclosure is typically 0.1 mg/kg to 100 mg/kg of the patient's body weight, between 0.1 mg/kg and 20 mg/kg of the patient's body weight, or 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the disclosure may be reduced by enhancing uptake and tissue penetration (e.g., into the brain) of the antibodies by modifications such as, for example, lipidation.

The methods for treating an infectious or malignant disease, condition or disorder comprising administration of an antibody, variant, or derivative thereof of the disclosure are typically tested in vitro, and then in vivo in an acceptable animal model, for the desired therapeutic or prophylactic activity, prior to use in humans. Suitable animal models, including transgenic animals, are well known to those of ordinary skill in the art. For example, in vitro assays to demonstrate the therapeutic utility of antigen-binding polypeptide described herein include the effect of an antigen-binding polypeptide on a cell line or a patient tissue sample. The effect of the antigen-binding polypeptide on the cell line and/or tissue sample can be determined utilizing techniques known to those of skill in the art, such as the assays disclosed elsewhere herein. In accordance with the disclosure, in vitro assays which can be used to determine whether administration of a specific antigen-binding polypeptide is indicated, include in vitro cell culture assays in which a patient tissue sample is grown in culture, and exposed to or otherwise administered a compound, and the effect of such compound upon the tissue sample is observed.

Various delivery systems are known and can be used to administer an antibody of the disclosure or a polynucleotide encoding an antibody of the disclosure, e.g., encapsulation in liposomes, microparticles, microcapsules, recombinant cells capable of expressing the compound, receptor-mediated endocytosis (see, e.g., Wu and Wu, 1987, *J. Biol. Chem.* 262:4429-4432), construction of a nucleic acid as part of a retroviral or other vector, etc.

In a further embodiment, the compositions of the disclosure are administered in combination with an antineoplastic agent, an antiviral agent, antibacterial or antibiotic agent or antifungal agents. Any of these agents known in the art may be administered in the compositions of the current disclosure.

In another embodiment, compositions of the disclosure are administered in combination with a chemotherapeutic agent. Chemotherapeutic agents that may be administered with the compositions of the disclosure include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In an additional embodiment, the compositions of the disclosure are administered in combination with cytokines. Cytokines that may be administered with the compositions of the disclosure include, but are not limited to, IL-2, IL-3, IL-4, IL-5, IL-6, IL-7, IL-10, IL-12, IL-13, IL-15, anti-CD40, CD40L, and TNF-α.

In additional embodiments, the compositions of the disclosure are administered in combination with other therapeutic or prophylactic regimens, such as, for example, radiation therapy.

Combination Therapies

Combination therapies are also provided, which includes the use of one or more of the anti-CD73 antibody of the present disclosure along with a second anticancer (chemotherapeutic) agent. Chemotherapeutic agents may be categorized by their mechanism of action into, for example, the following groups:

anti-metabolites/anti-cancer agents such as pyrimidine analogs floxuridine, capecitabine, and cytarabine;

purine analogs, folate antagonists, and related inhibitors;

antiproliferative/antimitotic agents including natural products such as vinca alkaloid (vinblastine, vincristine) and microtubule such as taxane (paclitaxel, docetaxel), vinblastin, nocodazole, epothilones, vinorelbine (NAVELBINE®), and epipodophyllotoxins (etoposide, teniposide);

DNA damaging agents such as actinomycin, amsacrine, busulfan, carboplatin, chlorambucil, cisplatin, cyclophosphamide (CYTOXAN®), dactinomycin, daunorubicin, doxorubicin, epirubicin, iphosphamide, melphalan, merchlorethamine, mitomycin, mitoxantrone, nitrosourea, procarbazine, taxol, taxotere, teniposide, etoposide, and triethylenethiophosphoramide;

antibiotics such as dactinomycin, daunorubicin, doxorubicin, idarubicin, anthracyclines, mitoxantrone, bleomycins, plicamycin (mithramycin), and mitomycin;

enzymes such as L-asparaginase which systemically metabolizes L-asparagine and deprives cells which do not have the capacity to synthesize their own asparagine;

antiplatelet agents;

antiproliferative/antimitotic alkylating agents such as nitrogen mustards cyclophosphamide and analogs (melphalan, chloranibucil, hexamethylmelamine, and thiotepa), alkyl nitrosoureas (carmustine) and analogs, streptozocin, and triazenes (dacarbazine);

antiproliferative/antimitotic antimetabolites such as folic acid analogs (methotrexate);

platinum coordination complexes (cisplatin, oxiloplatinim, and carboplatin), procarbazine, hydroxyurea, mitotane, and aminoglutethimide;

hormones, hormone analogs (estrogen, tamoxifen, goserelin, bicalutamide, and nilutamide), and aromatase inhibitors (letrozole and anastrozole);

anticoagulants such as heparin, synthetic heparin salts, and other inhibitors of thrombin;

fibrinolytic agents such as tissue plasminogen activator, streptokinase, urokinase, aspirin, dipyridamole, ticlopidine, and clopidogrel;

antimigratory agents;

antisecretory agents (breveldin);

immunosuppressives tacrolimus, sirolimus, azathioprine, and mycophenolate;

compounds (TNP-470, genistein) and growth factor inhibitors (vascular endothelial growth factor inhibitors and fibroblast growth factor inhibitors);

angiotensin receptor blockers, nitric oxide donors;

anti-sense oligonucleotides;

antibodies such as trastuzumab and rituximab;

cell cycle inhibitors and differentiation inducers such as tretinoin;

inhibitors, topoisomerase inhibitors (doxorubicin, daunorubicin, dactinomycin, eniposide, epirubicin, etoposide, idarubicin, irinotecan, mitoxantrone, topotecan, and irinotecan), and corticosteroids (cortisone, dexamethasone, hydrocortisone, methylprednisolone, prednisone, and prednisolone);

growth factor signal transduction kinase inhibitors;

dysfunction inducers;

toxins such as *Cholera* toxin, ricin, *Pseudomonas* exotoxin, *Bordetella* pertussis adenylate cyclase toxin, diphtheria toxin, and caspase activators;

and chromatin.

Further examples of chemotherapeutic agents include:

alkylating agents such as thiotepa and cyclophosphamide (CYTOXAN®);

alkyl sulfonates such as busulfan, improsulfan, and piposulfan;

aziridines such as benzodopa, carboquone, meturedopa, and uredopa;

emylerumines and memylamelamines including alfretamine, triemylenemelamine, triethylenephosphoramide, triethylenethiophosphoramide, and trimemylolomelamine;

acetogenins, especially bullatacin and bullatacinone;

a camptothecin, including synthetic analog topotecan;

bryostatin;

callystatin;

CC-1065, including its adozelesin, carzelesin, and bizelesin synthetic analogs;

ctyptophycins, particularly cryptophycin 1 and cryptophycin 8;

dolastatin;

duocarmycin, including the synthetic analogs KW-2189 and CBI-TMI;

eleutherobin;

pancratistatin;

a sarcodictyin;

spongistatin;

nitrogen mustards such as chlorambucil, chlornaphazine, cyclophosphamide, estramustine, ifosfamide, mechlorethamine, mechlorethamine oxide hydrochloride, melphalan, novembichin, phenesterine, prednimustine, trofosfamide, and uracil mustard;

nitrosoureas such as carmustine, chlorozotocin, foremustine, lomustine, nimustine, and ranimustine;

antibiotics such as the enediyne antibiotics (e.g., calicheamicin, especially calicheamicin gammaII and calicheamicin phiII), dynemicin including dynemicin A, bisphosphonates such as clodronate, an esperamicin, neocarzinostatin chromophore and related chromoprotein enediyne antibiotic chromomophores, aclacinomycins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrroline-doxorubicin, and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, and zorubicin;

anti-metabolites such as methotrexate and 5-fluorouracil (5-FU);

folic acid analogs such as demopterin, methotrexate, pteropterin, and trimetrexate;

purine analogs such as fludarabine, 6-mercaptopurine, thiamiprine, and thioguanine;

pyrimidine analogs such as ancitabine, azacitidine, 6-azauridine, carmofur, cytarabine, dideoxyuridine, doxifluridine, enocitabine, and floxuridine;

androgens such as calusterone, dromostanolone propionate, epitiostanol, mepitiostane, and testolactone;

anti-adrenals such as aminoglutethimide, mitotane, and trilostane;

folic acid replinishers such as frolinic acid;

trichothecenes, especially T-2 toxin, verracurin A, roridin A, and anguidine;

taxoids such as paclitaxel (TAXOL®) and docetaxel (TAXOTERE®);

platinum analogs such as cisplatin and carboplatin;

aceglatone; aldophosphamide glycoside; aminolevulinic acid; eniluracil; amsacrine; hestrabucil; bisantrene; edatraxate; defofamine; demecolcine; diaziquone; elformthine; elliptinium acetate; an epothilone; etoglucid; gallium nitrate; hydroxyurea; lentinan; leucovorin; lonidamine; maytansinoids such as maytansine and ansamitocins; mitoguazone; mitoxantrone; mopidamol; nitracrine; pentostatin; phenamet; pirarubicin; losoxantrone; fluoropyrimidine; folinic acid; podophyllinic acid; 2-ethylhydrazide; procarbazine; polysaccharide-K (PSK); razoxane; rhizoxin; sizofiran; spirogermanium; tenuazonic acid; triaziquone; 2,2',2"-tric-Uorotriemylamine; urethane; vindesine; dacarbazine; mannomustine; mitobronitol; mitolactol; pipobroman; gacytosine; arabinoside ("Ara-C"); cyclophosphamide; thiopeta; chlorambucil; gemcitabine (GEMZAR®); 6-thioguanine; mercaptopurine; methotrexate; vinblastine; platinum; etoposide (VP-16); ifosfamide; mitroxantrone; vancristine; vinorelbine (NAVELBINE®); novantrone; teniposide; edatrexate; daunomycin; aminopterin; xeoloda; ibandronate; CPT-11; topoisomerase inhibitor RFS 2000; difluoromethylornithine (DFMO); retinoids such as retinoic acid; capecitabine; FOLFIRI (fluorouracil, leucovorin, and irinotecan);

and pharmaceutically acceptable salts, acids, or derivatives of any of the above.

Also included in the definition of "chemotherapeutic agent" are anti-hormonal agents such as anti-estrogens and selective estrogen receptor modulators (SERMs), inhibitors of the enzyme aromatase, anti-androgens, and pharmaceutically acceptable salts, acids or derivatives of any of the above that act to regulate or inhibit hormone action on tumors.

Examples of anti-estrogens and SERMs include, for example, tamoxifen (including NOLVADEX™), raloxifene, droloxifene, 4-hydroxytamoxifen, trioxifene, keoxifene, LY117018, onapristone, and toremifene (FARESTON®).

Inhibitors of the enzyme aromatase regulate estrogen production in the adrenal glands. Examples include 4(5)-imidazoles, aminoglutethimide, megestrol acetate (MEGACE®), exemestane, formestane, fadrozole, vorozole (RIVISOR®), letrozole (FEMARA®), and anastrozole (ARIMIDEX®).

Examples of anti-androgens include flutamide, nilutamide, bicalutamide, leuprohde, and goserelin.

Examples of chemotherapeutic agents also include anti-angiogenic agents including, but are not limited to, retinoid acid and derivatives thereof, 2-methoxyestradiol, ANGIOSTATIN®, ENDOSTATIN®, suramin, squalamine, tissue inhibitor of metalloproteinase-1, tissue inhibitor of metalloproteinase-2, plasminogen activator inhibitor-1, plasminogen activator inhibitor-2, cartilage-derived inhibitor, paclitaxel (nab-paclitaxel), platelet factor 4, protamine sulphate (clupeine), sulphated chitin derivatives (prepared from queen crab shells), sulphated polysaccharide peptidoglycan complex (sp-pg), staurosporine, modulators of matrix metabolism including proline analogs ((1-azetidine-2-carboxylic acid (LACA)), cishydroxyproline, d,I-3,4-dehydroproline, thiaproline, α,α'-dipyridyl, beta-aminopropionitrile fumarate, 4-propyl-5-(4-pyridinyl)-2(3h)-oxazolone, methotrexate, mitoxantrone, heparin, interferons, 2 macroglobulin-serum, chicken inhibitor of metalloproteinase-3 (ChIMP-3), chymostatin, beta-cyclodextrin tetradecasulfate, eponemycin, fumagillin, gold sodium thiomalate, d-penicillamine, beta-1-anticollagenase-serum, alpha-2-antiplasmin, bisantrene, lobenzarit disodium, n-2-carboxyphenyl-4-chloroanthronilic acid disodium or "CCA", thalidomide, angiostatic steroid, carboxy aminoimidazole, and metalloproteinase inhibitors such as BB-94. Other anti-angiogenesis agents include antibodies, preferably monoclonal antibodies against these angiogenic growth factors: beta-FGF, alpha-FGF, FGF-5, VEGF isoforms, VEGF-C, HGF/SF, and Ang-1/Ang-2.

Examples of chemotherapeutic agents also include anti-fibrotic agents including, but are not limited to, the compounds such as beta-aminoproprionitrile (BAPN), as well as the compounds disclosed in U.S. Pat. No. 4,965,288 (Palfreyman, et al.) relating to inhibitors of lysyl oxidase and their use in the treatment of diseases and conditions associated with the abnormal deposition of collagen and U.S. Pat. No. 4,997,854 (Kagan et al.) relating to compounds which inhibit LOX for the treatment of various pathological fibrotic states, which are herein incorporated by reference. Further exemplary inhibitors are described in U.S. Pat. No. 4,943,593 (Palfreyman et al.) relating to compounds such as 2-isobutyl-3-fluoro-, chloro-, or bromo-allylamine, U.S. Pat. No. 5,021,456 (Palfreyman et al.), U.S. Pat. No. 5,059,714 (Palfreyman et al.), U.S. Pat. No. 5,120,764 (Mccarthy et al.), U.S. Pat. No. 5,182,297 (Palfreyman et al.), U.S. Pat. No. 5,252,608 (Palfreyman et al.) relating to 2-(1-naphthyloxymemyl)-3-fluoroallylamine, and U.S. Pub. No.: 2004/0248871 (Farjanel et al.), which are herein incorporated by reference.

Exemplary anti-fibrotic agents also include the primary amines reacting with the carbonyl group of the active site of the lysyl oxidases, and more particularly those which produce, after binding with the carbonyl, a product stabilized by resonance, such as the following primary amines: emylenemamine, hydrazine, phenylhydrazine, and their derivatives; semicarbazide and urea derivatives; aminonitriles such as BAPN or 2-nitroethylamine; unsaturated or saturated haloamines such as 2-bromo-ethylamine, 2-chloroethylamine, 2-trifluoroethylamine, 3-bromopropylamine, and p-halobenzylamines; and selenohomocysteine lactone.

Other anti-fibrotic agents are copper chelating agents penetrating or not penetrating the cells. Exemplary compounds include indirect inhibitors which block the aldehyde derivatives originating from the oxidative deamination of the lysyl and hydroxylysyl residues by the lysyl oxidases. Examples include the thiolamines, particularly D-penicillamine, and its analogs such as 2-amino-5-mercapto-5-methylhexanoic acid, D-2-amino-3-methyl-3-((2-acetamidoethyl)dithio)butanoic acid, p-2-amino-3-methyl-3-((2-aminoethyl)dithio)butanoic acid, sodium-4-((p-1-dimethyl-2-amino-2-carboxyethyl)dithio)butane sulphurate, 2-acetamidoethyl-2-acetamidoethanethiol sulphanate, and sodium-4-mercaptobutanesulphinate trihydrate.

Examples of chemotherapeutic agents also include immunotherapeutic agents including and are not limited to therapeutic antibodies suitable for treating patients. Some examples of therapeutic antibodies include simtuzumab, abagovomab, adecatumumab, afutuzumab, alemtuzumab, altumomab, amatuximab, anatumomab, arcitumomab, bavituximab, bectumomab, bevacizumab, bivatuzumab, blinatumomab, brentuximab, cantuzumab, catumaxomab, cetuximab, citatuzumab, cixutumumab, clivatuzumab, conatumumab, daratumumab, drozitumab, duligotumab, dusigitumab, detumomab, dacetuzumab, dalotuzumab, ecromeximab, elotuzumab, ensituximab, ertumaxomab, etaracizumab, farletuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab, iratumumab, labetuzumab, lexatumumab, lintuzumab, lorvotuzumab, lucatumumab, mapatumumab, matuzumab, milatuzumab, minretumomab, mitumomab, moxetumomab, namatumab, naptumomab, necitumumab, nimotuzumab, nofetumomab, ocaratuzumab, ofaturnumab, olaratumab, onartuzumab, oportuzumab, oregovomab, panitumumab, parsatuzumab, patritumab, pemtumomab, pertuzumab, pintumomab, pritumumab, racotumomab, radretumab, rilotumumab, rituximab, robatumumab, satumomab, sibrotuzumab, siltuximab, solitomab, tacatuzumab, taplitumomab, tenatumomab, teprotumumab, tigatuzumab, tositumomab, trastuzumab, tucotuzumab, ublituximab, veltuzumab, vorsetuzumab, votumumab, zalutumumab, CC49, and 3F8. Rituximab can be used for treating indolent B-cell cancers, including marginal-zone lymphoma, WM, CLL and small lymphocytic lymphoma. A combination of Rituximab and chemotherapy agents is especially effective.

The exemplified therapeutic antibodies may be further labeled or combined with a radioisotope particle such as indium-111, yttrium-90, or iodine-131.

In a one embodiment, the additional therapeutic agent is a nitrogen mustard alkylating agent. Nonlimiting examples of nitrogen mustard alkylating agents include chlorambucil.

In one embodiment, the compounds and compositions described herein may be used or combined with one or more additional therapeutic agents. The one or more therapeutic agents include, but are not limited to, an inhibitor of Abl, activated CDC kinase (ACK), adenosine A2B receptor (A2B), apoptosis signal-regulating kinase (ASK), Auroa kinase, Bruton's tyrosine kinase (BTK), BET-bromodomain (BRD) such as BRD4, c-Kit, c-Met, CDK-activating kinase (CAK), calmodulin-dependent protein kinase (CaMK), cyclin-dependent kinase (CDK), casein kinase (CK), discoidin domain receptor (DDR), epidermal growth factor receptors (EGFR), focal adhesion kinase (FAK), Flt-3, FYN, glycogen synthase kinase (GSK), HCK, histone deacetylase (HDAC), IKK such as IKKβε, isocitrate dehydrogenase (IDH) such as IDH1, Janus kinase (JAK), KDR, lymphocyte-specific protein tyrosine kinase (LCK), lysyl oxidase protein, lysyl oxidase-like protein (LOXL), LYN, matrix metalloprotease (MMP), mitogen-activated protein kinase (MAPK), NEK9, NPM-ALK, p38 kinase, platelet-derived growth factor (PDGF), phosphorylase kinase (PK), polo-like kinase (PLK), phosphatidylinositol 3-kinase (PI3K), protein kinase (PK) such as protein kinase A, B, and/or C, PYK, spleen tyrosine kinase (SYK), serine/threonine kinase TPL2, serine/threonine kinase STK, signal transduction and transcription (STAT), SRC, serine/threonine-protein kinase (TBK) such as TBK1, TIE, tyrosine kinase (TK), vascular endothelial growth factor receptor (VEGFR), YES, or any combination thereof.

ASK inhibitors include ASK1 inhibitors. Examples of ASK1 inhibitors include, but are not limited to, those described in WO 2011/008709 (Gilead Sciences) and WO 2013/112741 (Gilead Sciences).

Examples of BTK inhibitors include, but are not limited to, ibrutinib, HM71224, ONO-4059, and CC-292.

DDR inhibitors include inhibitors of DDR1 and/or DDR2. Examples of DDR inhibitors include, but are not limited to, those disclosed in WO 2014/047624 (Gilead Sciences), US 2009/0142345 (Takeda Pharmaceutical), US 2011/0287011 (Oncomed Pharmaceuticals), WO 2013/027802 (Chugai Pharmaceutical), and WO 2013/034933 (Imperial Innovations).

Examples of HDAC inhibitors include, but are not limited to, pracinostat and panobinostat.

JAK inhibitors inhibit JAK1, JAK2, and/or JAK3. Examples of JAK inhibitors include, but are not limited to, filgotinib, ruxolitinib, fedratinib, tofacitinib, baricitinib, lestaurtinib, pacritinib, XL019, AZD1480, INCB039110, LY2784544, BMS911543, and NS018.

LOXL inhibitors include inhibitors of LOXL1, LOXL2, LOXL3, LOXL4, and/or LOXL5. Examples of LOXL inhibitors include, but are not limited to, the antibodies described in WO 2009/017833 (Arresto Biosciences).

Examples of LOXL2 inhibitors include, but are not limited to, the antibodies described in WO 2009/017833 (Arresto Biosciences), WO 2009/035791 (Arresto Biosciences), and WO 2011/097513 (Gilead Biologics).

MMP inhibitors include inhibitors of MMP1 through 10. Examples of MMP9 inhibitors include, but are not limited to, marimastat (BB-2516), cipemastat (Ro 32-3555), and those described in WO 2012/027721 (Gilead Biologics).

PI3K inhibitors include inhibitors of PI3Kγ, PI3Kδ, PI3Kβ, PI3Kα, and/or pan-PI3K. Examples of PI3K inhibitors include, but are not limited to, wortmannin, BKM120, CH5132799, XL756, and GDC-0980.

Examples of PI3Kγ inhibitors include, but are not limited to, ZSTK474, AS252424, LY294002, and TG100115.

Examples of PI3Kδ inhibitors include, but are not limited to, PI3K II, TGR-1202, AMG-319, GSK2269557, X-339, X-414, RP5090, KAR4141, XL499, OXY111A, IPI-145, IPI-443, and the compounds described in WO 2005/113556 (ICOS), WO 2013/052699 (Gilead Calistoga), WO 2013/116562 (Gilead Calistoga), WO 2014/100765 (Gilead Calistoga), WO 2014/100767 (Gilead Calistoga), and WO 2014/201409 (Gilead Sciences).

Examples of PI3Kβ inhibitors include, but are not limited to, GSK2636771, BAY 10824391, and TGX221.

Examples of PI3Kα inhibitors include, but are not limited to, buparlisib, BAY 80-6946, BYL719, PX-866, RG7604, MLN1117, WX-037, AEZA-129, and PA799.

Examples of pan-PI3K inhibitors include, but are not limited to, LY294002, BEZ235, XL147 (SAR245408), and GDC-0941.

Examples of SYK inhibitors include, but are not limited to, tamatinib (R406), fostamatinib (R788), PRT062607, BAY-61-3606, NVP-QAB 205 AA, R112, R343, and those described in U.S. Pat. No. 8,450,321 (Gilead Connecticut).

TKIs may target epidermal growth factor receptors (EGFRs) and receptors for fibroblast growth factor (FGF), platelet-derived growth factor (PDGF), and vascular endothelial growth factor (VEGF). Examples of TKIs that target EGFR include, but are not limited to, gefitinib and erlotinib. Sunitinib is a non-limiting example of a TKI that targets receptors for FGF, PDGF, and VEGF.

Combination with Immune Checkpoint Inhibitor

The anti-CD73 antibodies of the present disclosure can be used, in some embodiments, together with an immune checkpoint inhibitor. Immune checkpoints are molecules in the immune system that either turn up a signal (co-stimulatory molecules) or turn down a signal. Many cancers protect themselves from the immune system by inhibiting the T cell signal. An immune checkpoint inhibitor can help stop such a protective mechanism by the cell cells. An immune checkpoint inhibitor may target any one or more of the following checkpoint molecules, PD-1, PD-L1, CTLA-4, LAG-3 (also known as CD223), CD28, CD122, 4-1BB (also known as CD137), or BTLA (also known as CD272).

Programmed T cell death 1 (PD-1) is a trans-membrane protein found on the surface of T cells, which, when bound to programmed T cell death ligand 1 (PD-L1) on tumor cells, results in suppression of T cell activity and reduction of T cell-mediated cytotoxicity. Thus, PD-1 and PD-L1 are immune down-regulators or immune checkpoint "off switches". Example PD-1 inhibitor include, without limitation, nivolumab, (Opdivo) (BMS-936558), pembrolizumab (Keytruda), pidilizumab, AMP-224, MEDI0680 (AMP-514), PDR001, MPDL3280A, MEDI4736, BMS-936559 and MSB0010718C.

Programmed death-ligand 1 (PD-L1) also known as cluster of differentiation 274 (CD274) or B7 homolog 1 (B7-H1) is a protein that in humans is encoded by the CD274 gene. Non-limiting examples of PD-L1 inhibitor include Atezolizumab (Tecentriq), Durvalumab (MEDI4736), Avelumab (MSB0010718C), MPDL3280A, BMS935559 (MDX-1105) and AMP-224.

CTLA-4 is a protein receptor that downregulates the immune system. Non-limiting examples of CTLA-4 inhibitors include ipilimumab (Yervoy) (also known as BMS-734016, MDX-010, MDX-101) and tremelimumab (formerly ticilimumab, CP-675,206).

Lymphocyte-activation gene 3 (LAG-3) is an immune checkpoint receptor on the cell surface works to suppress an immune response by action to Tregs as well as direct effects on CD8+ T cells. LAG-3 inhibitors include, without limitation. LAG525 and BMS-986016.

CD28 is constitutively expressed on almost all human CD4+ T cells and on around half of all CD8 T cells, prompts T cell expansion. Non-limiting examples of CD28 inhibitors include TGN1412.

CD122 increases the proliferation of CD8+ effector T cells. Non-limiting examples include NKTR-214.

4-1BB (also known as CD137) is involved in T-cell proliferation. CD137-mediated signaling is also known to protect T cells, and in particular, CD8+ T cells from activation-induced cell death. PF-05082566, Urelumab (BMS-663513) and lipocalin are example CD137 inhibitors.

For any of the above combination treatments, the anti-CD73 antibody can be administered concurrently or separately from the other anticancer agent. When administered separately, the anti-CD73 antibody can be administered before or after the other anticancer agent.

Diagnostic Methods

Over-expression of CD73 is observed in certain tumor samples, and patients having CD73-over-expressing cells are likely responsive to treatments with the anti-CD73 antibodies of the present disclosure. Accordingly, the antibodies of the present disclosure can also be used for diagnostic and prognostic purposes.

A sample that preferably includes a cell can be obtained from a patient, which can be a cancer patient or a patient desiring diagnosis. The cell be a cell of a tumor tissue or a tumor block, a blood sample, a urine sample or any sample from the patient. Upon optional pre-treatment of the sample, the sample can be incubated with an antibody of the present disclosure under conditions allowing the antibody to interact with a CD73 protein potentially present in the sample. Methods such as ELISA can be used, taking advantage of the anti-CD73 antibody, to detect the presence of the CD73 protein in the sample.

Presence of the CD73 protein in the sample (optionally with the amount or concentration) can be used for diagnosis of cancer, as an indication that the patient is suitable for a treatment with the antibody, or as an indication that the patient has (or has not) responded to a cancer treatment. For a prognostic method, the detection can be done at once, twice or more, at certain stages, upon initiation of a cancer treatment to indicate the progress of the treatment.

Compositions

The present disclosure also provides pharmaceutical compositions. Such compositions comprise an effective amount of an antibody, and an acceptable carrier. In some embodiments, the composition further includes a second anticancer agent (e.g., an immune checkpoint inhibitor).

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. Further, a "pharmaceutically acceptable carrier" will generally be a non-toxic solid, semisolid or liquid filler, diluent, encapsulating material or formulation auxiliary of any type.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose are also envisioned. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences by E. W. Martin, incorporated herein by reference. Such compositions will contain a therapeutically effective amount of the antigen-binding polypeptide, preferably in purified form, together with a suitable amount of carrier so as to provide the form for proper administration to the patient. The formulation should suit the mode of administration. The parental preparation can be enclosed in ampoules, disposable syringes or multiple dose vials made of glass or plastic.

In an embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

EXAMPLES

Example 1. Cloning of a Murine Antibody 101-Mu

This example describes the process of preparing an anti-human-CD73 mouse monoclonal antibody using the hybridoma technology. Human CD73 protein was prepared using a recombinant CHOK1 cell line expressing CD73 (CD73-CHOK1). To generate mouse monoclonal antibodies to human CD73, 6-8 week female BALB/c mice were firstly immunized with $1.5 \times 10^7$ CD73-CHOK1 cells. Day 14 and 33 post first immunization, the immunized mice were re-immunized with $1.5 \times 10^7$ CD73-CHOK1 cells. To select mice producing antibodies that bond the CD73 protein, sera from immunized mice were tested by ELISA. Briefly, microtiter plates were coated with human CD73 protein at 1 μg/ml in PBS, 100 μl/well at room temperature (RT) overnight, then blocked with 100 μl/well of 5% BSA. Dilutions of plasma from immunized mice were added to each well and incubated for 1-2 hours at RT. The plates were washed with PBS/Tween and then incubate with anti-mouse IgG antibody conjugated with Horse Radish Peroxidase (HRP) for 1 hour at RT. After washing, the plates were developed with ABTS substrate and analyzed by spectrophotometer at OD 405 nm. Mice with sufficient titers of anti-CD73 IgG were boosted with 50 ug human CD73-Fc protein at Day 54 post-immunization. The resulting mice were used for fusions. The hybridoma supernatants were tested for anti-CD73 IgGs by ELISA. Eight different hybridoma clones were identified, among which 101-Mu was selected for the further analysis. The VH sequence of 101-MU is shown in Table 6 as SEQ ID NO: 10, and the VL sequence is shown in Table 7 and SEQ ID NO: 15. The corresponding DNA sequences are shown in Table 10 as SEQ ID NO: 57 and 58.

Example 2. Binding of 101-Mu to CD73

This example tests the dose response of ELISA binding of mouse anti-CD73 mAb 101-Mu to recombinant human CD73 protein (1 ug/ml@100 ul), either alone or on cell surfaces.

Recombinant human CD73 protein (Novoprotein) was coated at 1 ug/ml in PBS onto microtiter plates for 2 h at room temperature (RT). After coating of antigen the wells were blocked with PBS/0.05% Tween (PBST) with 1% BSA for 1 h at RT. After washing of the wells with PBST, different concentrations of anti-CD73 antibodies were added to the well and incubated for 1 at RT. For detection of the binding antibodies, the HRP-conjugated secondary antibodies against mouse Fc (Jackson Immuno Research) were added, followed by the addition of fluorogenic substrates (Roche). Between all incubation steps, the wells of the plate were washed with PBST three times. Fluorescence was measured in a TECAN Spectrafluor plate reader.

An human anti-CD73, mAb1, was used as a positive control. mAb1 was generated according to the sequence disclosed in US2016/0194407. The comparative results are presented in FIG. 1, which shows an EC50 for 101-Mu as 0.08 nM and an EC50 for mAb1 as 0.03 nM.

Figure 2:
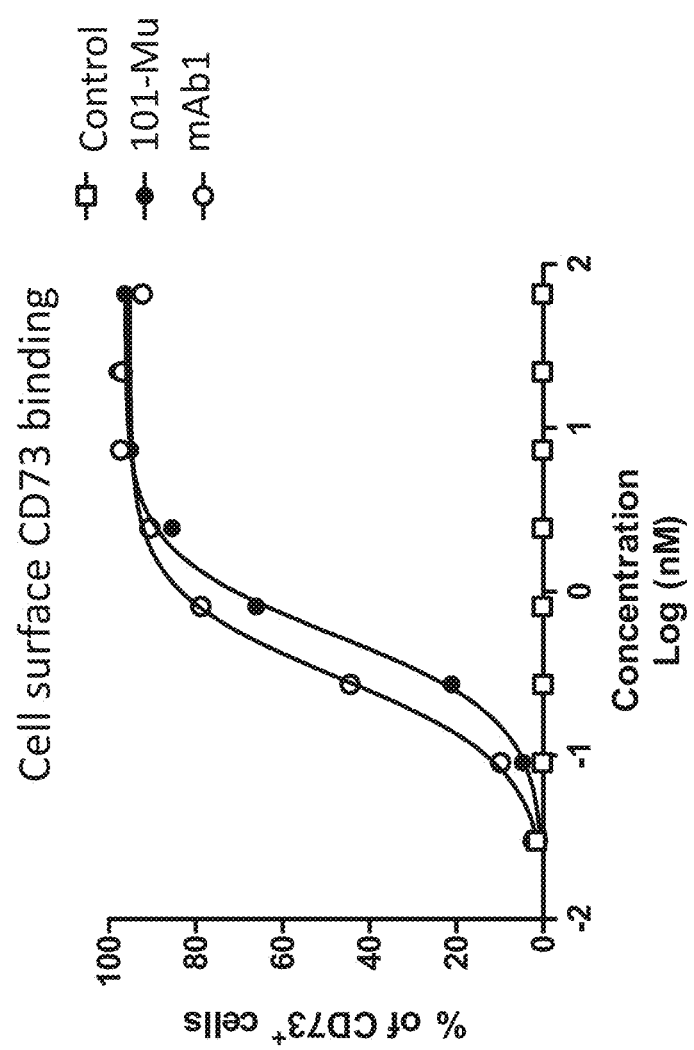
FIG. 2 shows the binding of the 101-Mu antibody to recombinant human CD73 protein on the surface of human ovarian cancer cells.

FIG. 2 shows the results from a binding assay using a human ovarian cancer cell line (SK-OV-3 cells) which endogenously express human CD73 on the surface. After incubation with the indicated antibodies, the cells were stained with different concentrations of IgG control, mouse anti-CD73 (101-Mu) and the reference antibody (mAb1) at 4° C. for 30 mins. Then, the cells were washed with PBS three times, followed by incubation with APC-labeled anti-mouse Fc specific antibody (Invitrogen) at 4° C. for 30 mins. Binding was measured using an FACSCanto (Becton-Dickinson). Like FIG. 1, this figures show that 101-Mu has equivalent binding affinity to CD73 as mAb1 (For 101-Mu, EC50 was 0.54 nM; for mAb1, EC50 was 0.30 nM).

Figure 3:
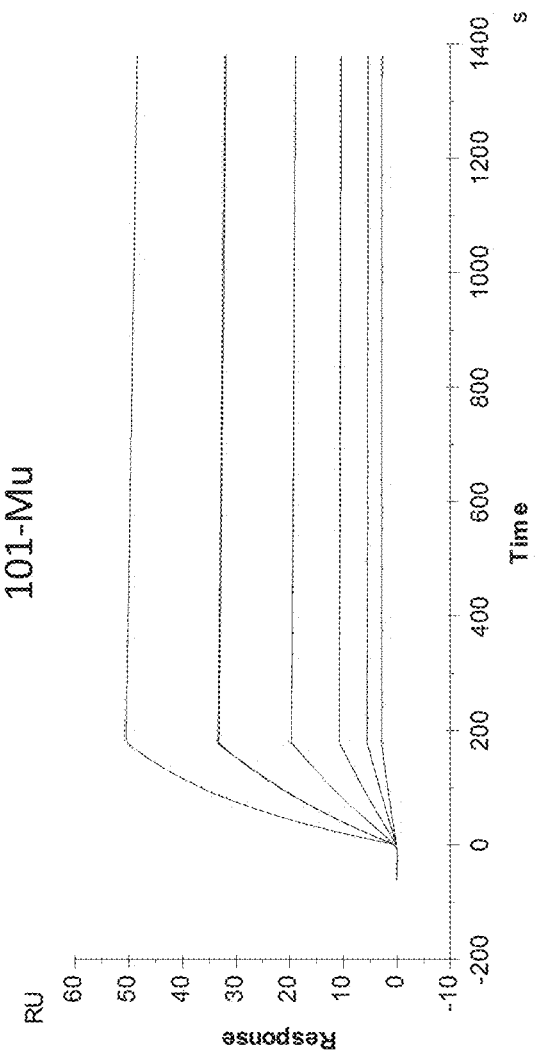
FIG. 3 shows the binding kinetics of the 101-Mu antibody to recombinant CD73 protein.
Figure 3:
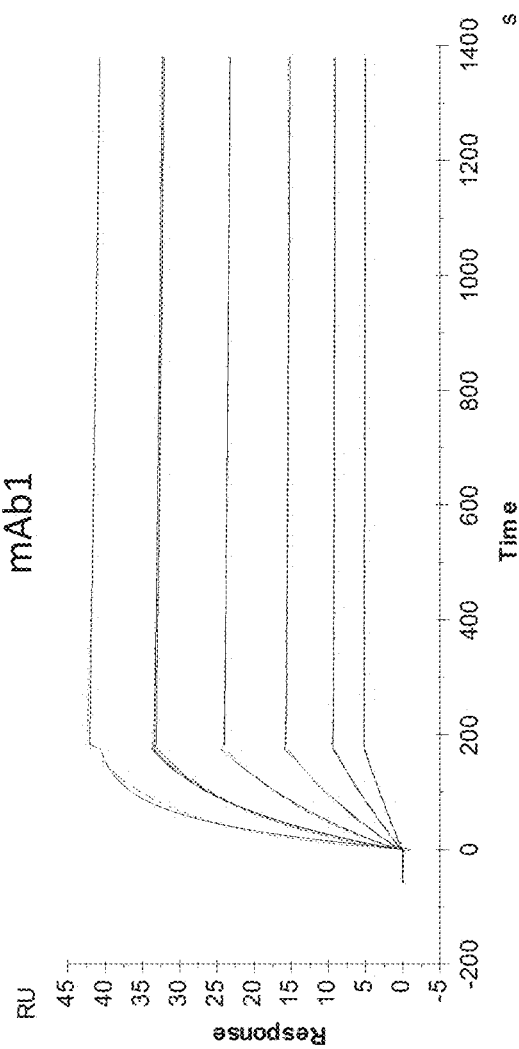

FIG. 3 plots the binding kinetics of 101-Mu and mAb1 with recombinant human CD73 (recombinant human CD73 was set as an analyte with serial concentrations (100, 50, 25, 12.5, 6.25, 3.125 nM)). The binding kinetics assay of antibody to antigen was performed using Biacore T200 system through a human antibody capture approach. The anti-mouse Fc IgG were immobilized on CM5 sensor chip according to the manufactory's instruction. The test antibody was injected and captured by the immobilized anti-human Fc IgG. And then serial concentrations of the antigen was individually injected, and the binding profile was recorded for each concentration antigen analyte, respectively. The assay system was regenerated by injection of 10 mM Glycine-HCl pH 1.5 for 30 seconds. The running buffer was HBS-EP+ (10 mM HEPES, pH 7.4, 150 mM NaCl, 3 mM EDTA and 0.05% P20). The assay temperature was 25° C., and the association and dissociation time were 180 and 600 seconds, respectively. The Biacore data were fitted using Biacore T200 evaluation software 1.0 according to 1:1 binding model to calculate the association (ka) and dissociation (kd) rate constants as well as the equilibrium constant (KD). In addition to FIG. 3, some summary data presented in the table below.

| Sample | ka (1/Ms) | kd (1/s) | KD (M) |
|---|---|---|---|
| 101-Mu | 8.13E+04 | 3.42E−05 | 4.21E−10 |
| mAb1 | 2.08E+05 | 2.73E−05 | 1.31E−10 |

Example 3. Inhibition of CD73 Enzymatic Activity by 101-Mu

This example tests the ability of the 101-Mu antibody to inhibit the enzymatic activity of CD73.

Recombinant human CD73 protein (0.3 ug/ml) was incubated in 96-well flat bottom microplates in the presence of different doses of anti-CD73 or isotype control Abs. Plates were incubated for 15 mins at 37° C. ATP (100 uM) and AMP (100 uM) were then added to each well and incubated for another 30 mins at 37° C. Luciferase-containing Cell-Titer-Glo (Promega) was added into wells and light emission inhibition was measured by luminometer (Molecular Device).

Figure 4:
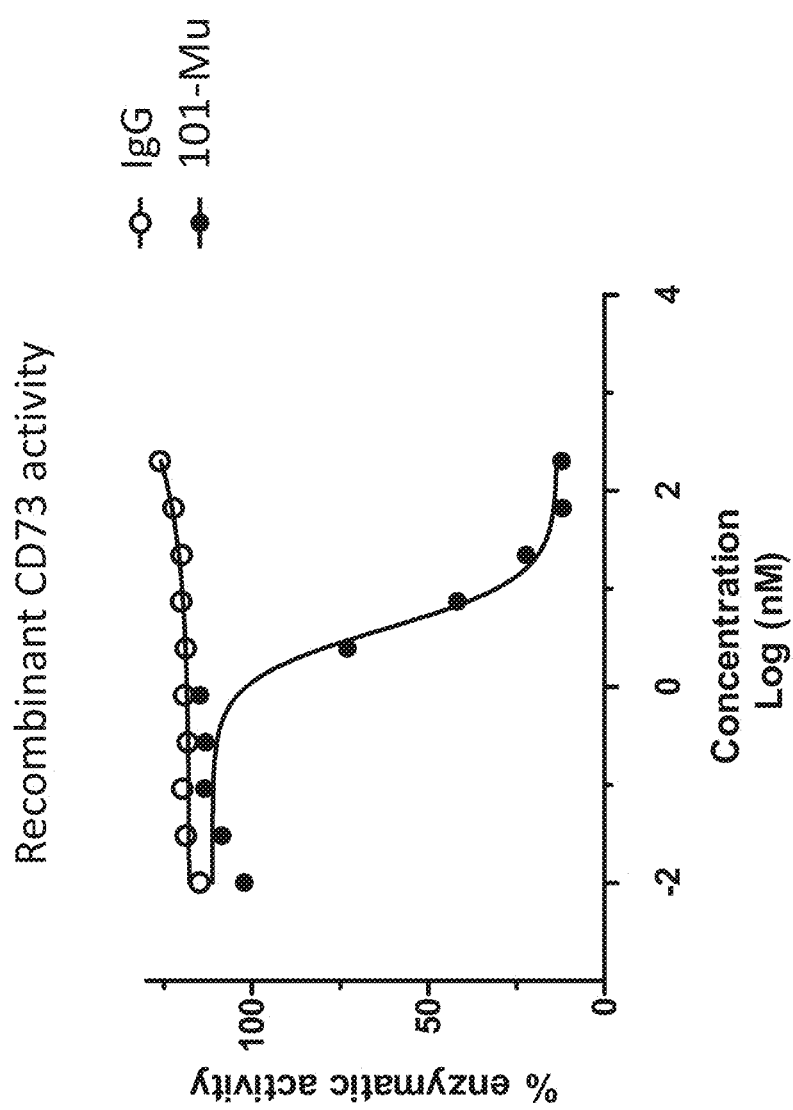
FIG. 4 shows that the 101-Mu antibody inhibits CD73's enzymatic activity.

Excess of AMP is known to block ATP-dependent luciferase activity. Addition of CD73 that catalyzes AMP to produce adenosine and inorganic phosphate restores luciferase activity and light emission. Thus, antibodies that block enzymatic activity of CD73 can diminish light emission. The percentage of enzyme activity is evaluated as described below: Residual CD73 activity was calculated as: (CD73+Ab+ATP+AMP)−(ATP+AMP)/(CD73+ATP+AMP)−(ATP+AMP)*100. The results are plotted in FIG. 4, which shows that unlike the negative control IgG, 101-Mu dose-dependently inhibited CD73's enzymatic activity (IC50=3.89 nM).

Figure 5:
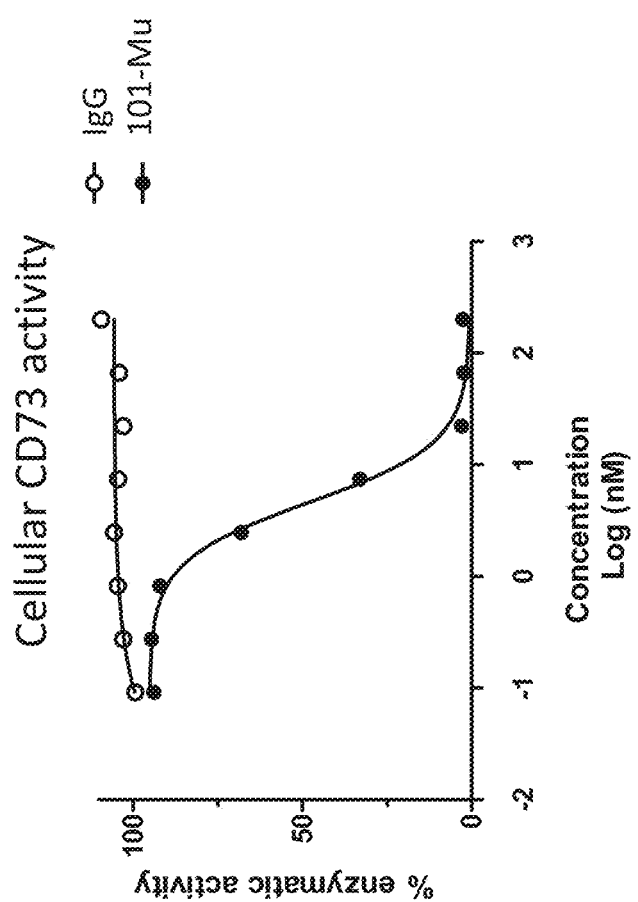
FIG. 5 shows that the 101-Mu antibody inhibits CD73's enzymatic activity on cell surface.

CD73 expressing SK-OV-3 cells were plated into 96-well plate at $1\times10^5$ cells per well in the presence of different doses of anti-CD73 Abs or isotype control Abs. Plates were incubated for 15 mins at 37° C. AMP (100 uM) was added to each well and incubated for 1 hr at 37° C. Supernatants were collected into a new 96-well plate and ATP was added to a final concentration of 100 uM. CellTiter-Glo reagent (Promega) was added 1:1 and cellular CD73 enzyme activity was determined by measuring light emission luminometer (Molecular Device). The percentage of enzyme activity is evaluated as described below: Residual CD73 activity was calculated as: (SK-OV-3 cells+Ab+ATP+AMP)−(ATP+AMP)/(SK-OV-3 cells+ATP+AMP)−(ATP+AMP)*100. The results are plotted in FIG. 5, which shows that unlike the negative control IgG, 101-Mu dose-dependently inhibited CD73's enzymatic activity (IC50=4.62 nM).

Example 4. Reversal of AMP-Mediated CD4+ T Cell Suppression by 101-Mu

This example tests the ability of the antibody to reverse AMP-mediated CD4+ T cell suppression.

Figure 6:
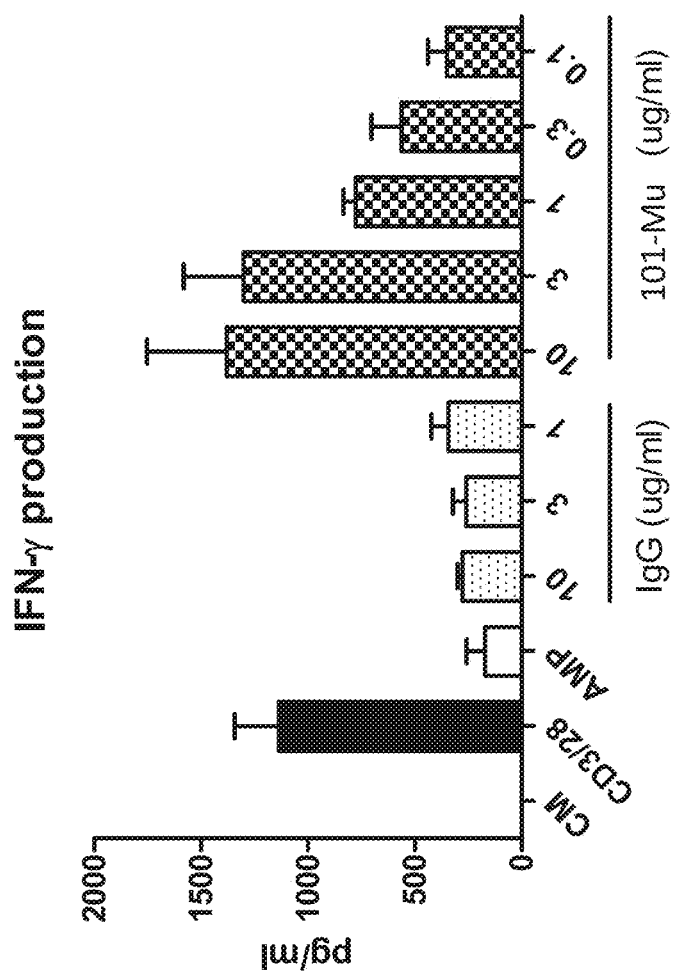
FIG. 6 shows that 101-Mu reversed AMP-mediated CD4+ T cell suppression, as indicated by the production of IFN-γ.
Figure 7:
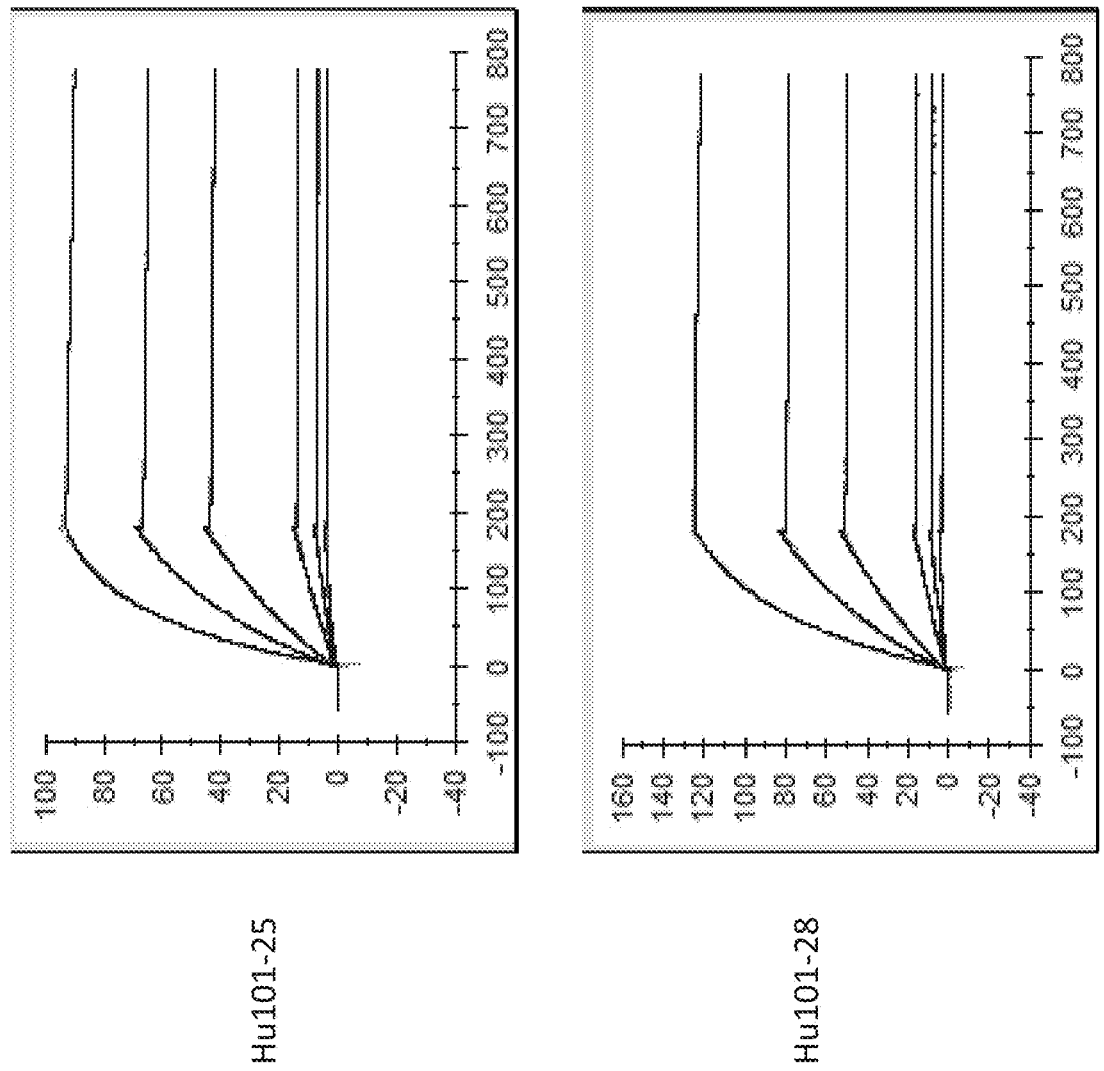
FIG. 7 shows the binding kinetics of humanized antibodies.
Figure 8:
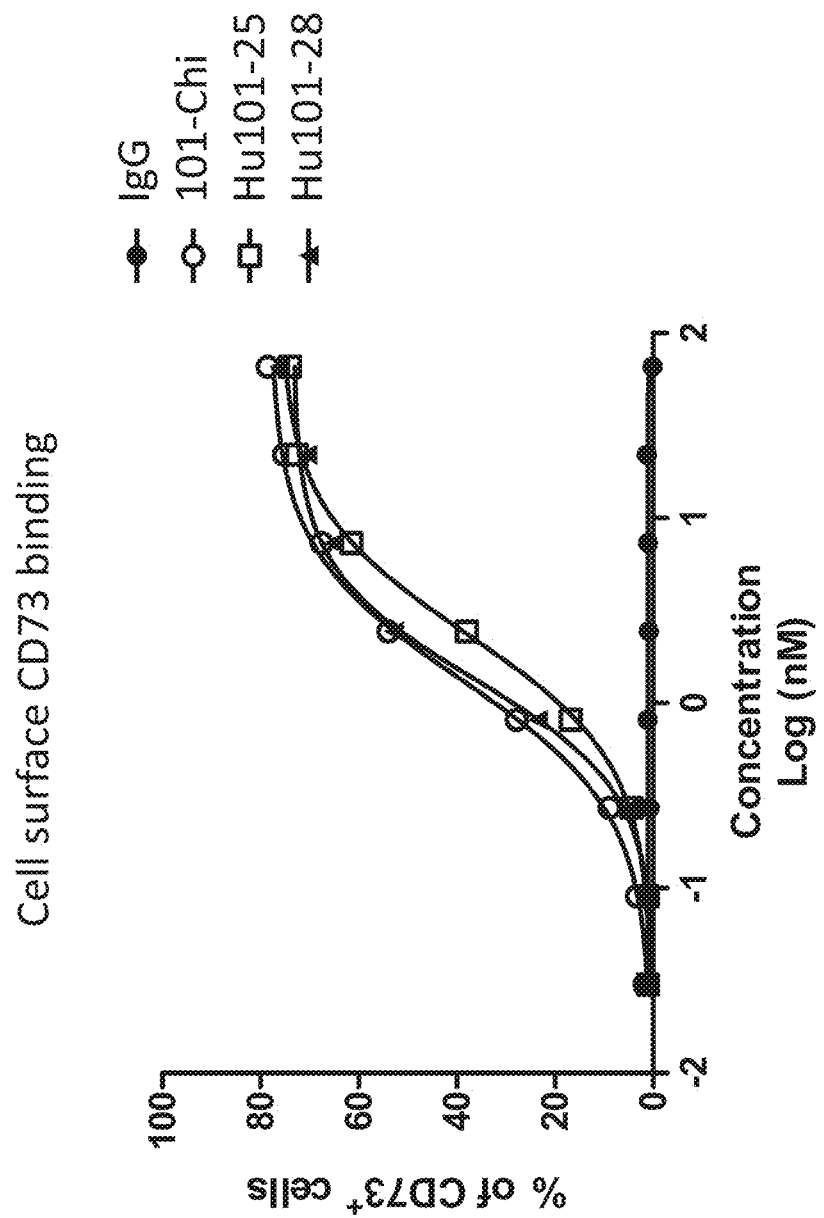
FIG. 8 shows that the humanized antibodies hound to cell surface CD73 proteins.

Human CD4+ T cells were purified from PBMCs by positive selection using the human CD4 microbeads (Miltenyi Biotech). Isolated CD4+ T cells were stimulated with pre-coated anti-CD3 antibody (2 μg/ml) and soluble anti-CD28 antibody (1 ug/ml) in the presence or absence of AMP (500 μM). Serial dilutions of anti-CD73 antibodies and control IgGs were added into each well and cultured for 72 hrs and the supernatant was analyzed for IFN-γ by ELISA. As shown in FIG. 6, 101-Mu dose-dependently increased IFN-γ production of the CD4+ cells, while the control had no relevant impact.

Example 5. Humanization of 101-Mu

The examples above show that the 101-Mu antibody is a potent inhibitor of CD73 enzymatic activity and can completely reverse the immunosuppressive effect of adenosine on T cell activation. Accordingly, the antibody was selected as the basis for humanization.

The 101-Mu variable region genes were employed to create a humanized MAb. The VH and VK of 101-MU were compared against the available database of human Ig gene sequences to identify the overall best-matching human germline Ig gene sequences. For the light chain, the closest human matches were the A10/Jk4 (design 1) and L6/Jk4 (design 2) genes, and for the heavy chain the closest human match was the VH4-B/JH6 gene. Humanized variable domain sequences were then designed where the CDR1 (SEQ ID NO. 4), 2 (SEQ ID NO. 5) and 3 (SEQ ID NO. 6) of the 101-MU light chain were grafted onto framework sequences of the matched light chain genes, and the CDR1 (SEQ ID NO. 1), 2 (SEQ ID NO. 2), and 3 (SEQ ID NO. 3) sequences of the 101-MU VH were grafted onto framework sequences of the matched VH gene.

A 3D model was then generated to determine if there were any framework positions where replacing the mouse amino acid to the human amino acid could affect binding and/or CDR conformation. Useful back-mutations identified, as well as peptide sequences that include such mutations, are shown in the tables below (underlined).

TABLE 3

VH back-mutations and VH sequences with the back-mutations:
VH Design: VH4-b/JH6

| Construct | Mutation |
|---|---|
| 101-Mu VH | Chimera |
| 101-Mu VH.1 | CDR-grafted |

TABLE 3-continued

VH back-mutations and VH sequences with the back-mutations:
VH Design: VH4-b/JH6

| Construct | Mutation |
|---|---|
| 101-Mu VH.1a | V71R |
| 101-Mu VH.1b | V71R, V67I |
| 101-Mu VH.1c | V71R, V67I, I48M |
| 101-Mu VH.1d | V71R, V67I, I48M, S30T, G44K |

TABLE 4

VK back-mutations and VK sequences
with the back-mutations (design 1):
VK Design 1: A10/Jk4

| Construct | Mutation |
|---|---|
| 101-Mu Vk | Chimera |
| 101-Mu Vk.1 | CDR-grafted |
| 101-Mu Vk.1a | F71Y, D70S |
| 101-Mu Vk.1b | F71Y, D70S, K49S |
| 101-Mu Vk.1c | F71Y, D70S, K49S, L46P, L47W |
| 101-Mu Vk.1d | F71Y, D70S, K49S, L46P, L47W, T5S |

TABLE 5

VK back-mutations and VK sequences
with the back-mutations (design 1):
VK Design 2: L6/Jk4

| Construct | Mutation |
|---|---|
| 101-Mu VK.2 | CDR-grafted |
| 101-Mu VK.2a | F71Y, D70S |
| 101-Mu VK.2b | F71Y, D70S, K49S, I58V |
| 101-Mu VK.2c | F71Y, D70S, K49S, L46P, L47W, T5S, A43S, I58V |

TABLE 6

Humanized VH and humanized VH with back-mutations:

```
Name
(SEQ ID NO:)     Sequences

Kabat #                     1         2         3          4
                 12345678901234557890123456789 01A2345 67890123456789
101-Mu VH (10)   DVQLQESGPGLVKPSQSLSLTCSVTGYSITSGYYWNWIRQFPGNKLEWMG 101-Mu VH.1 (11) EVQLQESGPGLVKPSETLSLTCAVSGYSISSGYYWNWIRQPPGKGLEWIG 101-Mu VH.1A (9) EVQLQESGPGLVKPSETLSLTCAVSGYSISSGYYWNWIRQPPGKGLEWIG 101-Mu VH.1B (12) EVQLQESGPGLVKPSETLSLTCAVSGYSISSGYYWNWIRQPPGKGLEWIG 101-Mu VH.1C (13) EVQLQESGPGLVKPSETLSLTCAVSGYSISSGYYWNWIRQPPGKGLEWMG 101-Mu VH.1D (7)  EVQLQESGPGLVKPSETLSLTCAVSGYSITSGYYWNWIRQPPGKKLEWMG

VH4-B/JH6 (14)   QVQLQESGPGLVKPSETLSLTCAVSGYSISSGYYWGWIRQPPGKGLEWIG

Kabat #             5         6         7         8         9
                 01234567890123456789012345678901 2ABC34567890123456
101-Mu VH        YINYGGSNGYNPSLKSRISITRDTSKNQFFLKLNSVTTEDTATYYCARDY 101-Mu VH.1      YINYGGSNGYNPSLKSRVTISVDTSKNQFSLKLSSVTAADTAVYYCARDY 101-Mu VH.1A     YINYGGSNGYNPSLKSRVTISRDTSKNQFSLKLSSVTAADTAVYYCARDY 101-Mu VH.1B     YINYGGSNGYNPSLKSRITISRDTSKNQFSLKLSSVTAADTAVYYCARDY 101-Mu.VH.1C     YINYGGSNGYNTSLKSRITISRDTSKNQFSLKLSSVTAADTAVYYCARDY
```

TABLE 6-continued

Humanized VH and humanized VH with back-mutations:

| Name (SEQ ID NO:) | Sequences |
|---|---|
| 101-Mu VH.1D | YINYGGSNGYNPSLKSRITISRDTSKNQFSLKLSSVTAADTAVYYCARDY |
| VH4-B/JH6 | SIYHSGSTYYNPSLKSRVTISVDTSKNQFSLKLSSVTAADTAVYYCAR-- |
| Kabat # | 0             1 |
|  | 7890ABC1234567890123 |
| 101-Mu VH | DAYYEALDDWGQGTSVTVSS |
| 101-Mu VH.1 | DAYYEALDDWGQGTTVTVSS |
| 101-Mu VH.1A | DAYYEALDDWGQGTTVTVSS |
| 101-Mu VH.1B | DAYYEALDDWGQGTTVTVSS |
| 101-Mu VH.1C | DAYYEALDDWGQGTTVTVSS |
| 101-Mu VH.1D | DAYYEALDDWGQGTTVTVSS |
| VH4-B/JH6 | ---------WGQGTTVTVSS |

Bold: CDR regions; underlined: back-mutations

TABLE 7

Humanized VK and humanized VK with back-mutations (design 1):

| Name (SEQ ID NO:) | Sequences |
|---|---|
| Kabat # | 1         2         3         4         5 |
|  | 12345678901234567890123456789012345676901 |
| 101-Mu VK (15) | QIVLSQSPAILSASPGEKVTMTCRASSRVN-YMHWYQQKPGSSPKPWISAT |
| 101-Mu VK.1 (16) | EIVLTQSPDFQSVTPKEKVTITCRASSRVN-YMHWYQQKPDQSPKLLIKAT |
| 101-Mu VK.1A (17) | EIVLTQSPDFQSVTPKEKVTITCRASSRVN-YMHWYQQKPDQSPKLLIKAT |
| 101-Mu VK.1B (18) | EIVLTQSPDFQSVTPKEKVTITCRASSRVN-YMHWYQQKPDQSPKLLI<u>S</u>AT |
| 101-Mu VK.1C (19) | EIVLTQSPDFQSVTPKEKVTITCRASSRVN-YMHWYQQKPDQSPK<u>PWIS</u>AT |
| 101-Mu VK.1D (20) | EIVL<u>S</u>QSPDFQSVTPKEKVTITCRASSRVN-YMHWYQQKPDQSPK<u>PWIS</u>AT |
| A10/JK4 (21) | EIVLTQSPDFQSVTPKEKVTITCRASQSIGSSLHWYQQKPDQSPKLLIKYA |
| Kabat # | 6         7         8         9         0 |
|  | 23456789012345676901234567890123456769012 |
| 101-Mu VK | SNLASGVPARFSGSGSGTSYSLTISRVETEDAATYYCQQWSSNPPTFGGGT |
| 101-Mu VK.1 | SNLASGVPSRFSGSGSGTDFTLTINSLEAEDAATYYCQQWSSNPPTFGGGT |
| 101-Mu VK.1A | SNLASGVPSRFSGSGSGT<u>SY</u>TLTINSLEAEDAATYYCQQWSSNPPTFGGGT |
| 101-Mu VK.1B | SNLASGVPSRFSGSGSGT<u>SY</u>TLTINSLEAEDAATYYCQQWSSNPPTFGGGT |
| 101-Mu VK.1C | SNLASGVPSRFSGSGSGT<u>SY</u>TLTINSLEAEDAATYYCQQWSSNPPTFGGGT |
| 101-Mu VK.1D | SNLASGVPSRFSGSGSGT<u>SY</u>TLTINSLEAEDAATYYCQQWSSNPPTFGGGT |
| A10/JK4 | SQSFSGVPSRFSGSGSGTDFTLTINSLEAEDAATYYC---------FGGGT |
| Kabat # | 34567 |
| 101-Mu VK | KLEIK |
| 101-Mu VK.1 | KVEIK |
| 101-Mu VK.1A | KVEIK |
| 101-Mu VK.1B | KVEIK |
| 101-Mu VK.1C | KVEIK |

TABLE 7-continued

Humanized VK and humanized VK with back-mutations (design 1):

| Name (SEQ ID NO:) | Sequences |
|---|---|
| 101-Mu VK.1D | KVEIK |
| A10/JK4 | KVEIK |

Bold: CDR regions; underlined: back-mutations

TABLE 8

Humanized VK and humanized VK with back-mutations (design 2):

| Name (SEQ ID NO:) | Sequences |
|---|---|
| Kabat # |         1          2          3          4          5<br>12345678901234567890123456789012345678901234567890 1 |
| 101-Mu VK (15) | QIVLSQSPAILSASPGEKVTMTCRASSRVN-YMHWYQQKPGSSPKPWISAT |
| 101-Mu VK.2 (22) | EIVLTQSPATLSLSPGERATLSCRASSRVN-YMHWYQQKPGQAPRLLIYAT |
| 101-Mu VK.2A (23) | EIVLTQSPATLSLSPGERATLSCRASSRVN-YMHWYQQKPGQAPRLLI<u>Y</u>AT |
| 101-Mu VK.2B (24) | EIVLTQSPATLSLSPGERATLSCRASSRVN-YMHWYQQKPGQAPRLLI<u>S</u>AT |
| 101-Mu VK.2C (8) | EIVL<u>S</u>QSPATLSLSPGERATLSCRASSRVN-YMHWYQQKPGQ<u>SPRPWIS</u>AT |
| L6/JK4 (25) | EIVLTQSPATLSLSPGERATLSCRASQSVSSYLAWYQQKPGQAPRLLIYDA |
| Kabat # |         6          7          8          9          0<br>23456789012345678901234567890123456789012345678 9012 |
| 101-Mu VK | SNLASGVPARFSGSGSGTSYSLTISRVETEDAATYYCQQWSSNPPTFGGGT |
| 101-Mu VK.2 | SNLASGIPARFSGSGSGTDFTLTISSLEPEDFAVYYCQQWSSNPPTFGGGT |
| 101-Mu VK.2A | SNLASGIPARFSGSGSGT<u>SY</u>TLTISSLEPEDFAVYYCQQWSSNPPTFGGGT |
| 101-Mu VK.2B | SNLASG<u>V</u>PARFSGSGSGT<u>SY</u>TLTISSLEPEDFAVYYCQQWSSNPPTFGGGT |
| 101-Mu VK.2C | SNLASG<u>V</u>PARFSGSGSGT<u>SY</u>TLTISSLEPEDFAVYYCQQWSSNPPTFGGGT |
| L6/JK4 | SNRATGIPARFSGSGSGTDFTITISSLEPEDFAVYYC---------FGGGT |
| Kabat # | 34567 |
| 101-Mu VK | KLEIK |
| 101-Mu VK.2 | KVEIK |
| 101-Mu VK.2A | KVEIK |
| 101-Mu VK.2B | KVEIK |
| 101-Mu VK.2C | KVEIK |
| L6/JK4 | KVEIK |

Bold: CDR regions; underlined: back-mutations

The humanized VH and VK genes were produced synthetically and then respectively cloned into vectors containing the human gamma 1 and human kappa constant domains. The pairing of the human VH and the human VK created a number of humanized antibodies as listed in the table below.

TABLE 9

| | Humanized antibodies | | | | | | | |
|---|---|---|---|---|---|---|---|---|
| | 101-Mu VK.1a | 101-Mu VK.1b | 101-Mu VK.1c | 101-Mu VK.1d | 101-Mu VK.2a | 101-Mu VK.2b | 101-Mu VK.2c | 101-Mu VK |
| 101-Mu VH.1a | Hu101-1 | Hu101-2 | Hu101-3 | Hu101-4 | Hu101-17 | Hu101-21 | Hu101-25 | |
| 101-Mu VH.1b | Hu101-5 | Hu101-6 | Hu101-7 | Hu101-8 | Hu101-18 | Hu101-22 | Hu101-26 | |

TABLE 9-continued

| | | | Humanized antibodies | | | | |
|---|---|---|---|---|---|---|---|
| 101-Mu VK.1a | 101-Mu VK.1b | 101-Mu VK.1c | 101-Mu VK.1d | 101-Mu VK.2a | 101-Mu VK.2b | 101-Mu VK.2c | 101-Mu VK |
| 101-Mu VH.1c Hu101-9 | Hu101-10 | Hu101-11 | Hu101-12 | Hu101-19 | Hu101-23 | Hu101-27 | |
| 101-Mu VH.1d Hu101-13 | Hu101-14 | Hu101-15 | Hu101-16 | Hu101-20 | Hu101-24 | Hu101-28 | |
| 101-Mu VH | | | | | | | 101-Mu chimera |

Table 10 shows a few example nucleotide sequences encoding the VH and VL regions of the 101-MU and Hu101-28 antibodies.

TABLE 10

| Nucleotide sequences | | |
|---|---|---|
| Name | SEQ ID NO: | Sequence |
| 101-Mu VH | 57 | GATGTACAGCTTCAGGAGTCAGGACCTGGCCTCGTGAAACCTTCTCAGTC TCTGTCTCTCACCTGCTCTGTCACTGGCTACTCCATCACCAGTGGTTATT ACTGGAACTGGATCCGGCAGTTTCCAGGAAACAAACTGGAATGGATGGGC TACATAAACTACGGCGGTAGCAATGGCTACAACCCATCTCTCAAAAGTCG GATCTCCATCACTCGGGACACATCTAAGAACCAGTTTTTCCTGAAGCTGA ATTCTGTGACTACTGAGGACACAGCTACATATTACTGTGCAAGAGACTAT GATGGTTACTACGAAGCTCTGGACGACTGGGGTCAAGGAACCTCAGTCAC CGTCTCCTCA |
| 101-Mu VL | 58 | CAAATTGTTCTCTCCCAGTCTCCAGCAATCCTGTCTGCATCTCCAGGGGA GAAGGTCACAATGACTTGCAGGGCCAGCTCACGTGTAAATTACATGCACT GGTACCAGCAGAAGCCAGGATCCTCCCCCAAACCCTGGATTTCTGCCACA TCCAACCTGGCTTCTGGAGTCCCTGCTCGCTTCAGTGGCAGTGGGTCTGG GACCTCTTACTCTCTCACAATTAGCAGAGTAGAGACTGAAGATGCTGCCA CTTATTACTGCCAGCAGTGGAGTAGTAACCCACCCACGTTCGGAGGGGGG ACCAAGCTGGAAATAAAA |
| Hu101-28 VH | 59 | GAGGTACAGCTTCAGGAGTCAGGACCTGGCCTCGTGAAACCTTCTGAGAC TCTGTCTCTCACCTGCGCTGTCTCTGGCTACTCCATCACCAGTGGTTATT ACTGGAACTGGATCCGGCAGCCTCCAGGAAAGAAGCTGGAATGGATGGGC TACATCAACTACGGCGGTAGCAATGGCTACAACCCATCTCTCAAAAGTCG GATCACCATCTCTAGGGACACATCTAAGAACCAGTTTTCCCTGAAGCTGA GTTCTGTGACTGCTGCCGACACAGCTGTGTATTACTGTGCAAGAGACTAT GATGCTTACTACGAAGCTCTGGACGACTGGGGTCAAGGAACCACAGTCAC CGTCTCCTCA |
| Hu101-28 VL | 60 | GAAATTGTTCTCTCCCAGTCTCCAGCAACCCTGTCTCTGTCTCCAGGGGA GAGGGCCACACTGTCTTGCAGGGCCAGCTCACGTGTAAATTACATGCACT GGTACCAGCAGAAGCCAGGACAGTCCCCCAGACCCTGGATTTCTGCCACA TCCAACCTGGCTTCTGGAGTCCCTGCTCGCTTCAGTGGCAGTGGGTCTGG GACCTCTTACACTCTCACAATTAGCAGCCTGGAGCCAGAAGATTTCGCCG TGTATTACTGCCAGCAGTGGAGTAGTAACCCACCCACGTTCGGAGGGGGG ACCAAGGTGGAAATCAAA |

Example 6. Testing of the Humanized Antibodies

This example tested the humanized antibodies in terms of their binding affinity and inhibitory activities. The testing procedures are similar to those described in Examples 1-4, and the results are presented in FIG. 7-11.

For the binding assay, the Biacore T200 system was used through human antibody capture approach. The anti-human Fc IgG were immobilized on CM5 sensor chip according to the manufactory's instruction. The test antibody was injected and captured by the immobilized anti-human Fc IgG. And then serial concentrations of antigen was individually injected, and the binding profile was recorded for each concentration antigen analyte, respectively. The assay system was regenerated by injection of 10 mM Glycine-HCl pH 1.5 for 30 seconds. The running buffer was HBS-EP+ (10 mM HEPES, pH 7.4, 150 mM NaCl, 3 mM EDTA and 0.05% P20). The assay temperature was 25° C., and the association and dissociation time were 180 and 600 seconds, respectively. The Biacore data were fitted using Biacore T200 evaluation software 1.0 according to 1:1 binding model to calculate the association (ka) and dissociation (kd) rate constants as well as the equilibrium constant (KD).

Among all the antibodies tested, Hu101-25 and Hu101-28 showed the highest binding affinity (see FIG. 7 and the table below) and were used for subsequent analyses.

| Sample | ka (1/Ms) | kd (1/s) | KD (M) |
|---|---|---|---|
| Hu101-25 | 7.37E+04 | 5.51E−05 | 7.47E−10 |
| Hu101-28 | 5.89E+05 | 3.47E−05 | 5.90E−10 |

Human ovarian cancer cell line (SK-OV-3 cells) which endogenously expressed human CD73 on the surface were stained with different concentrations of IgG control, chimeric anti-CD73 (101-Mu-Chimeric, or 101-Chi) and humanized anti-CD73 antibodies (Hu101-25 and Hu101-28) at ° C. for 30 mins. Then, the cells were washed with PBS three times, followed by incubation with APC-labeled anti-human Fc specific antibody (Invitrogen) at 4° C. for 30 mins. Binding was measured using an FACSCanto (Becton-Dickinson), and the results are presented in FIG. 8 (see also the table below).

| 101-Chimeric | EC50 = 1.35 nM |
| Hu101-25 | EC50 = 2.38 nM |
| Hu101-28 | EC50 = 1.35 nM |

Recombinant human CD73 protein (0.3 ug/ml) was incubated in 96-well flat bottom microplates in the presence of different doses of anti-CD73 or isotype control Abs. Plates were incubated for 15 mins at 37° C. ATP (100 uM) and AMP (100 uM) were then added to each well and incubated for another 30 mins at 37° C. Luciferase-containing Cell-Titer-Glo (Promega) was added into wells and light emission inhibition was measured by luminometer (Molecular Device). Excess of AMP is known to block ATP-dependent luciferase activity. Addition of CD73 that catalyze AMP to produce adenosine and inorganic phosphate restores luciferase activity and light emission. Thus, antibodies that block enzymatic activity of CD73 will diminish light emission. The percentage of enzyme activity is evaluated as described below: Residual CD73 activity: (CD73+Ab+ATP+AMP)−(ATP+AMP)/(CD73+ATP+AMP)−(ATP+AMP)*100.

Figure 9:
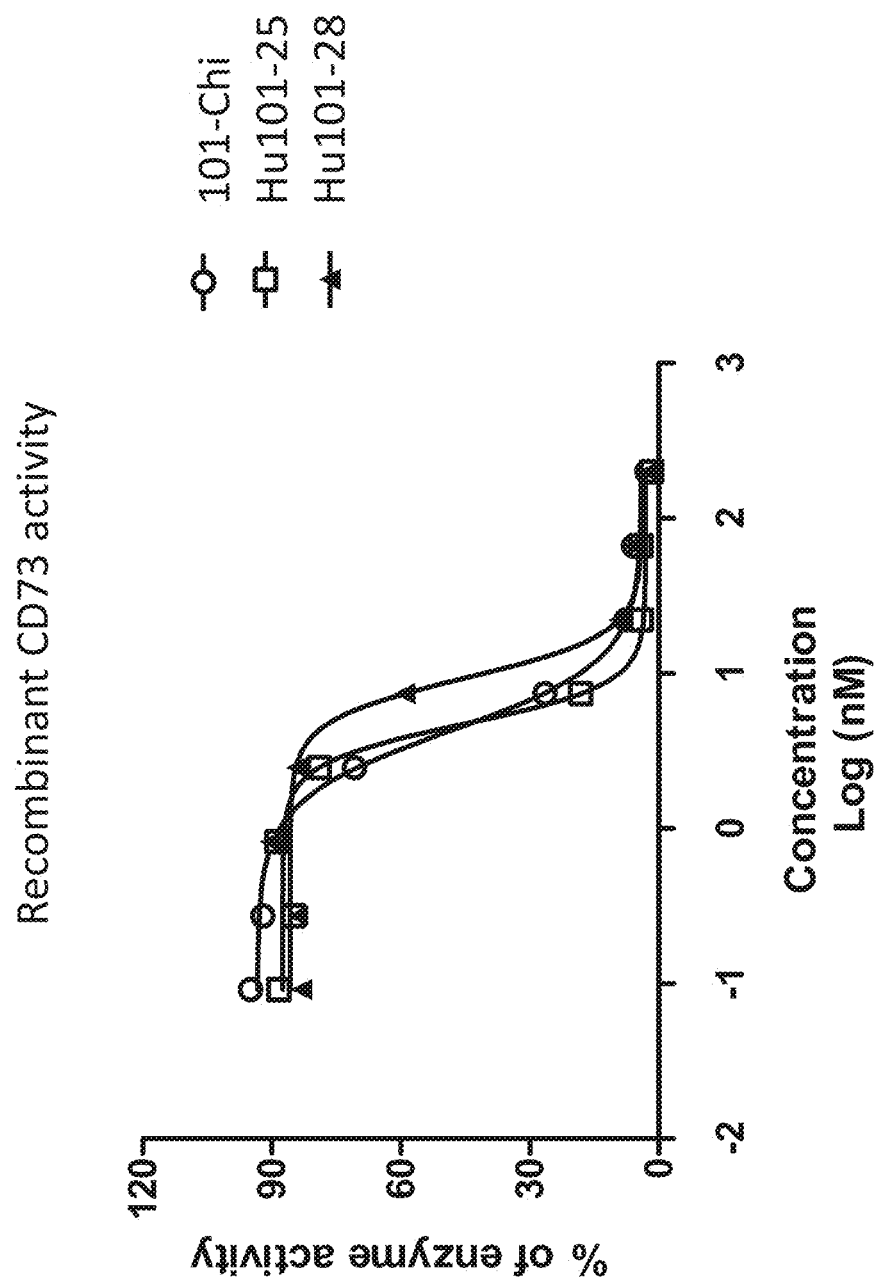
FIG. 9 shows that the humanized antibodies inhibited the enzymatic activities of the CD73 proteins.

FIG. 9 shows that all three tested antibodies exhibited strong inhibitory activities (see the table below too).

|  | IC50 (nM) | Max. Inhibition (%) |
| --- | --- | --- |
| 101-Chimeric | 4.25 | 98% |
| Hu101-25 | 4.72 | 99% |
| Hu101-28 | 9.35 | 98% |

Figure 10:
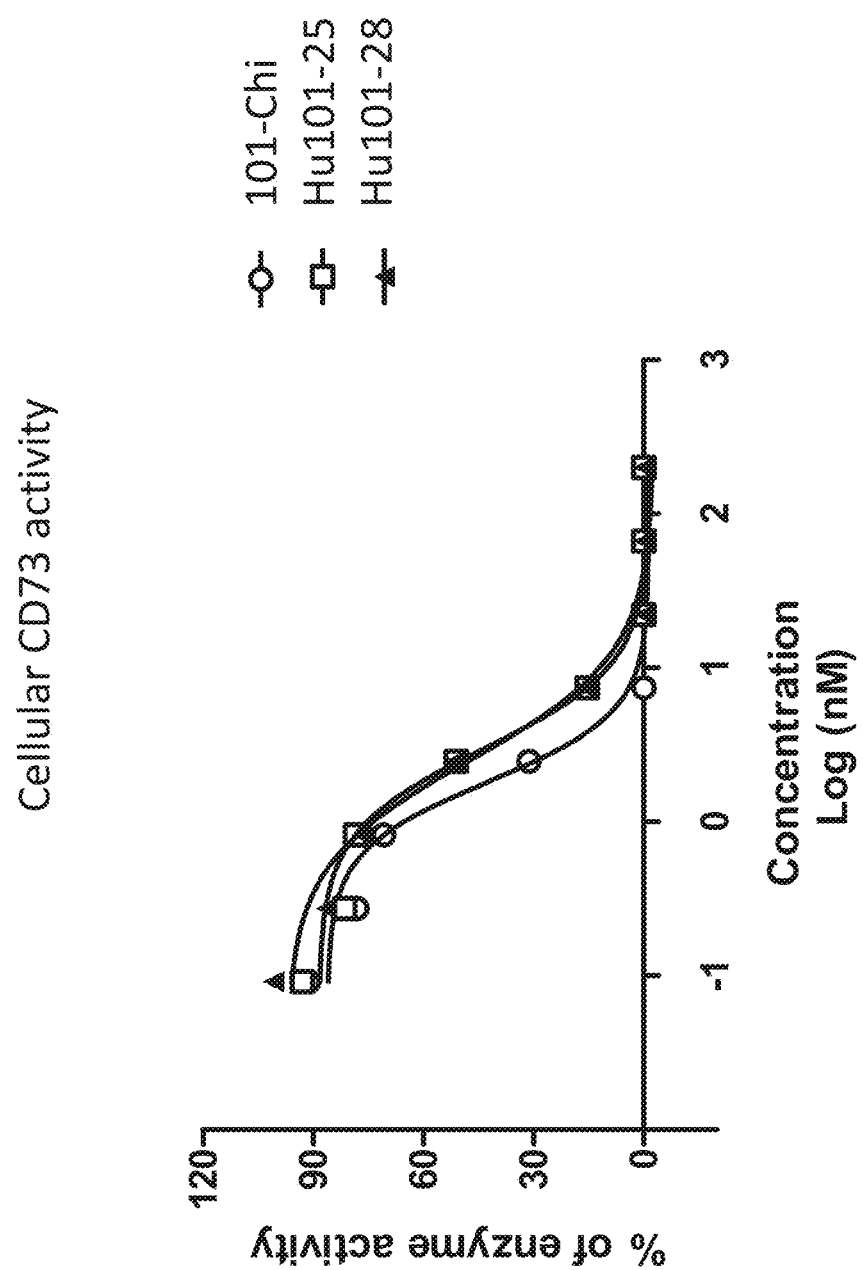
FIG. 10 shows that the humanized antibodies inhibited the enzymatic activities of cell surface CD73 proteins.

FIG. 10 shows the results of testing the inhibition of CD73 enzymatic activity by the humanized antibodies. CD73 expressing SK-OV-3 cells were plated into 96-well plate at 1×10^5 cells per well in the presence of different doses of anti-CD73 Abs or isotype control Abs. Plates were incubated for 15 mins at 37° C. AMP (100 uM) was added to each well and incubated for 1 hr at 37° C. Supernatants were collected into a new 96-well plate and ATP was added to a final concentration of 100 uM. CellTiter-Glo reagent (Promega) was added 1:1 and cellular CD73 enzyme activity was determined by measuring light emission luminometer (Molecular Device). The percentage of enzyme activity is evaluated as described below: Residual CD73 activity: (SK-OV-3 cells+Ab+ATP+AMP)−(ATP+AMP)/(SK-OV-3 cells+ATP+AMP)−(ATP+AMP)*100. The results are shown in FIG. 10 and the table below, demonstrating potent inhibitory effects by these antibodies.

|  | IC50 (nM) | Max. Inhibition (%) |
| --- | --- | --- |
| 101-Chimeric | 1.82 | 100% |
| Hu101-25 | 2.98 | 100% |
| Hu101-28 | 2.52 | 100% |

Figure 11:
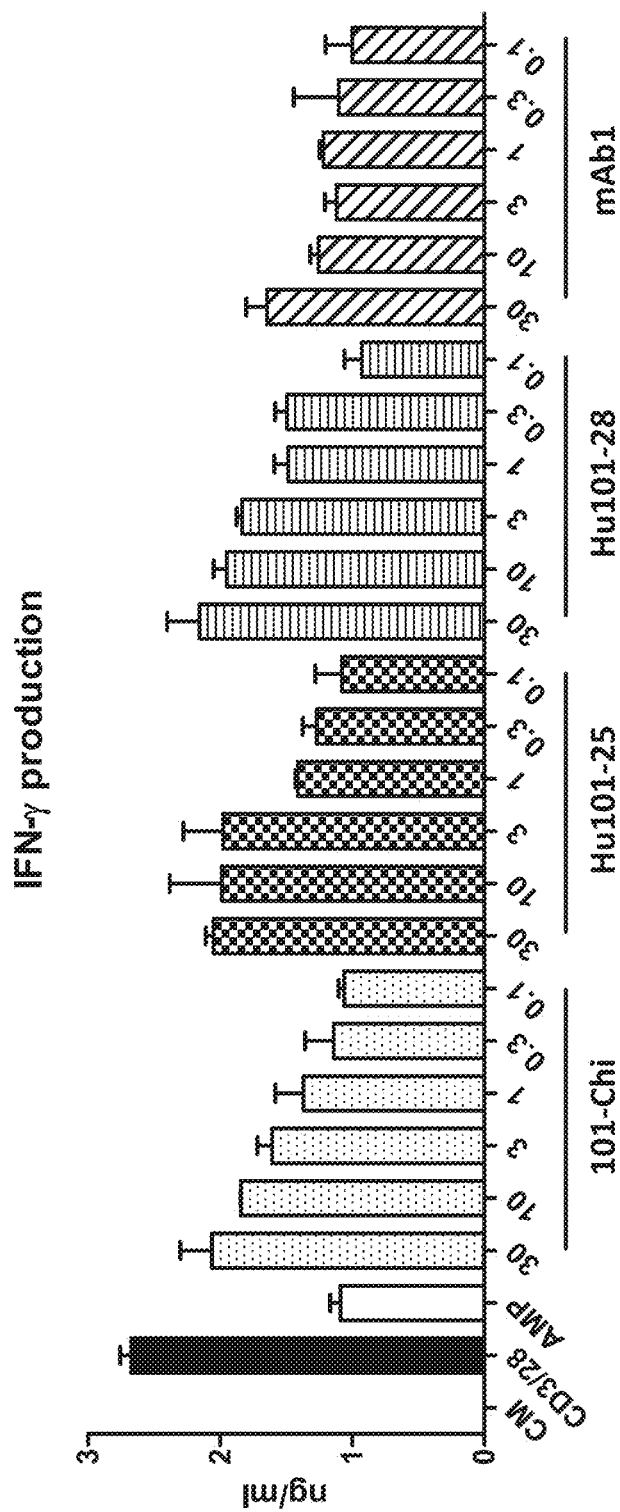
FIG. 11 shows that the humanized antibodies reversed AMP-mediated CD4+ T cell suppression, as indicated by the production of IFN-γ.

To test the antibodies' ability to reverse AMP-mediated CD4+ T cell suppression, human CD4+ cells were purified from PBMCs by positive selection using the human CD4 microbeads (Miltenyi Biotech). Isolated CD4+ T cells were stimulated with pre-coated anti-CD3 antibody (2 µg/ml) and soluble anti-CD28 antibody (1 µg/ml) in the presence or absence of AMP (500 µM). Serial dilutions of anti-CD73 antibodies and control IgGs were added into each well and cultured for 72 hrs and the supernatant was analyzed for IFN-γ by ELISA. As shown in FIG. 11, all three tested antibodies dose-dependently reversed the AMP-mediated suppression of the CD4+ T cells.

Example 7. Computer Simulation of Further Variation and Optimization of the Humanized Antibodies It was contemplated that certain amino acid residues within the CDR regions or the framework regions could be changed to further improve or retain the activity and/or stability of the antibodies. Variants were tested, with a computational tool (VectorNTI, available at www.ebi.ac.uk/tools/msa/clustalo/), with respect to their structural, conformational and functional properties, and those (within the CDR regions) that showed promises are listed in the tables below.

TABLE 11

VH and VL CDRs and their variants suitable for inclusion in humanized antibodies:

| Name | Sequence | SEQ ID NO: |
| --- | --- | --- |
| VH CDR1 | SGYTWN | 1 |
| Variant | TGYYWN | 26 |
| Variant | CGYYWN | 27 |
| Variant | SAYYWN | 28 |
| Variant | SPYYWN | 29 |
| VH CDR2 | YINYGGSNGY NPSLKS | 2 |
| Variant | YINYGASNGY NPSLKS | 30 |
| Variant | YINYGPSNGY NPSLKS | 31 |
| Variant | YINYGGTNGY NPSLKS | 32 |
| Variant | YINYGGCNGY NPSLKS | 33 |
| Variant | YINYGGSDGY NPSLKS | 34 |
| Variant | YINYGGSEGY NPSLKS | 35 |
| Variant | YINYGGSQGY NPSLKS | 36 |
| VH CDR3 | DYDAYYEALD D | 3 |
| Variant | DYDAYYDALD D | 37 |
| Variant | DYDAYYQALD D | 38 |
| Variant | DYDAYYNALD D | 39 |
| Variant | DYDAYYEGLD D | 40 |
| Variant | DYDAYYECLD D | 41 |
| VL CDR1 | RASSRVNYM H | 4 |
| Variant | RATSRVNYM H | 42 |

TABLE 11-continued

VH and VL CDRs and their variants suitable for inclusion in humanized antibodies:

| Name | Sequence | SEQ ID NO: |
|---|---|---|
| Variant | RA<u>C</u>SRVNYM H | 43 |
| Variant | RAS<u>T</u>RVNYM H | 44 |
| Variant | RAS<u>C</u>RVNYM H | 45 |
| VL CDR3 | QQWSSNPPT | 6 |
| Variant | <u>N</u>QWSSNPPT | 46 |
| Variant | <u>D</u>QWSSNPPT | 47 |
| Variant | <u>E</u>QWSSNPPT | 48 |
| Variant | Q<u>N</u>WSSNPPT | 49 |
| Variant | Q<u>D</u>WSSNPPT | 50 |
| Variant | Q<u>E</u>WSSNPPT | 51 |
| Variant | QQ<u>Y</u>SSNPPT | 52 |
| Variant | QQW<u>T</u>SNPPT | 53 |
| Variant | QQW<u>C</u>SNPPT | 54 |
| Variant | QQWS<u>T</u>NPPT | 55 |
| Variant | QQWS<u>C</u>NPPT | 56 |

Underline: hotspot mutation residues and their substitutes

Example 8. Hu101-28 is a Dual-Mechanism Anti-CD73 Antibody

This example shows that Hu101-28 has dual mechanisms of action. It not only blocks the enzymatic activity of CD73 in a non-competitive manner and also induces the internalization of cell surface CD73.

Figure 12:
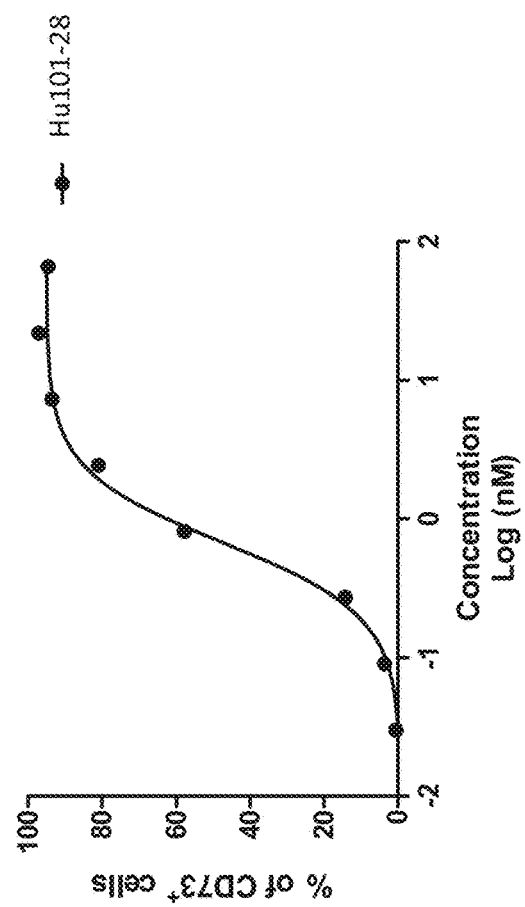
FIG. 12 shows the potent binding of Hu101-28 to soluble and cell surface CD73.
Figure 12:
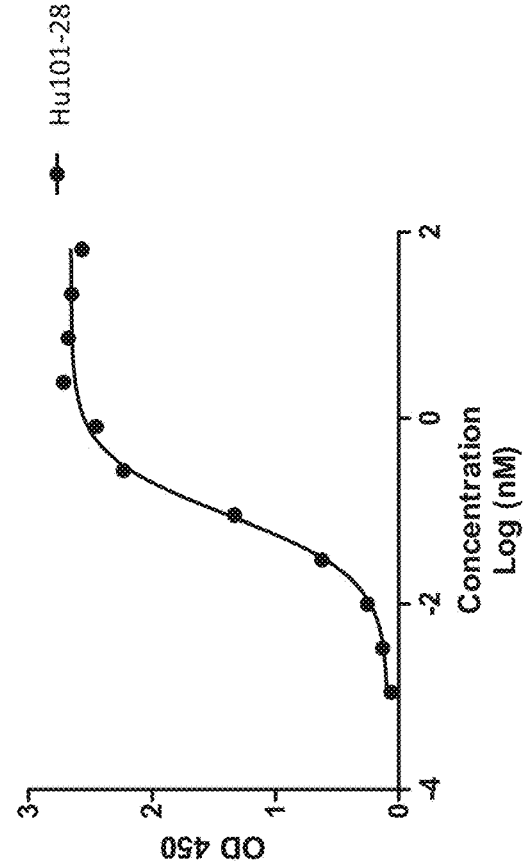

The binding of CD73 proteins was tested with soluble and cell surface CD73, and the results are shown in FIG. 12. In the left panel, 100 µl of a solution containing recombinant human CD73 (2 µg/ml) was used in an ELISA binding assay, and the chart shows that Hu101-28. In the right panel, human ovarian carcinoma cell line (SK-OV-3) was stained with different concentrations of Hu101-28 and analyzed for surface binding by flow cytometry. As shown, the $EC_{50}$ in the tests were 88.7 pM and 0.67 nM, respectively, underscoring the high affinity of the antibody.

Figure 13:
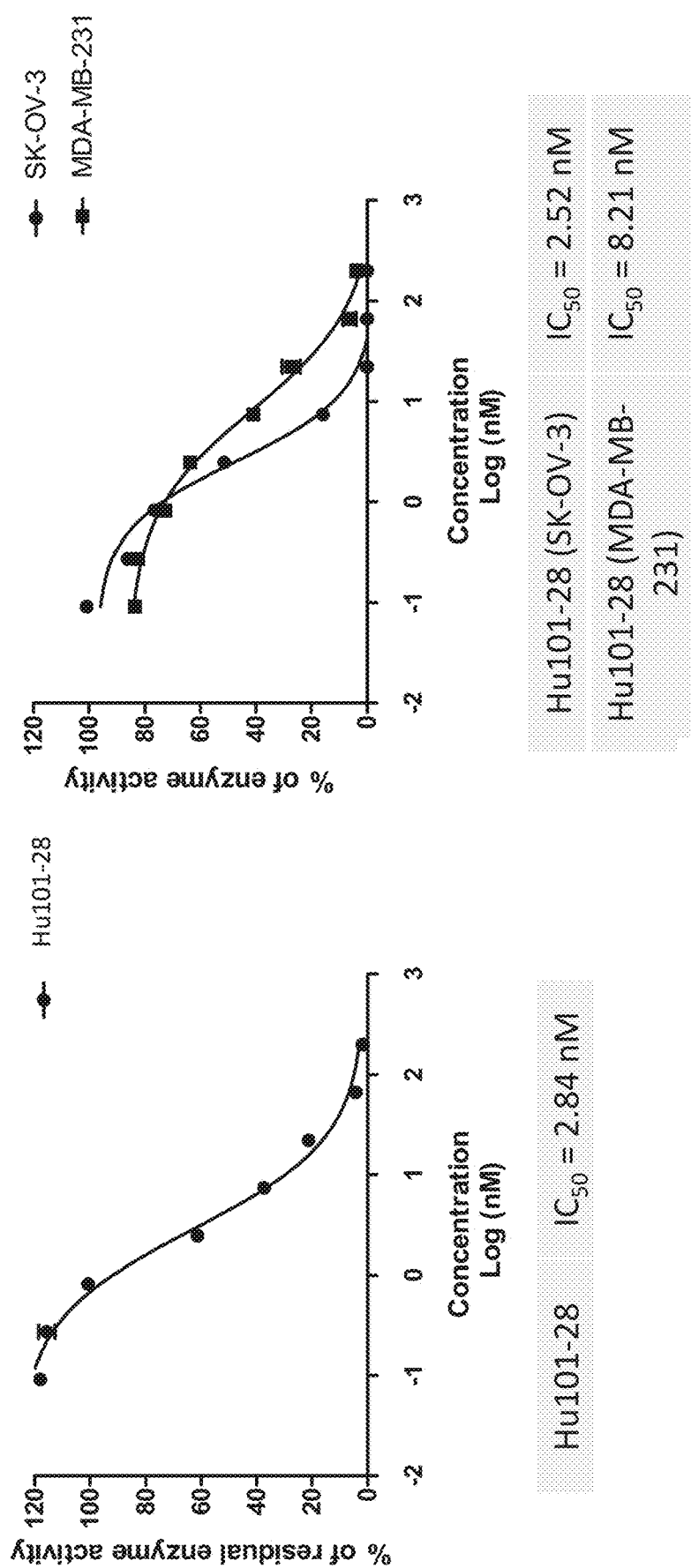
FIG. 13 shows that Hu101-28's binding to CD73 effectively blocks the enzymatic activity of CD73.

Next, the ability of Hu101-28 in blocking CD73 activities. Recombinant human CD73 (0.3 µg/ml) was incubated with Hu101-28 for 15 mins. ATP (100 µM) and AMP (100 µM) were then added for another 30 mins. CellTiter-Glo (Promega) was added and light emission inhibition was measured by luminometer. As shown in FIG. 13, left panel, the $IC_{50}$ in the solution was 2.84 nM. With respect to cell-found CD73, SK-OV-3 or MDA-MB-231 cells (1×10^5 cells) were incubated with Hu101-28 for 15 mins followed by sequential addition of AMP (100 µM) and ATP (100 µM) with further incubation for 1 hr. CellTiter-Glo (Promega) was added and light emission inhibition was measured by luminometer. As shown in FIG. 13, right panel, the $IC_{50}$ was 2.52 nM and 8.21 nM for SK-OV-3 and MDA-MB-231, respectively.

Figure 14:
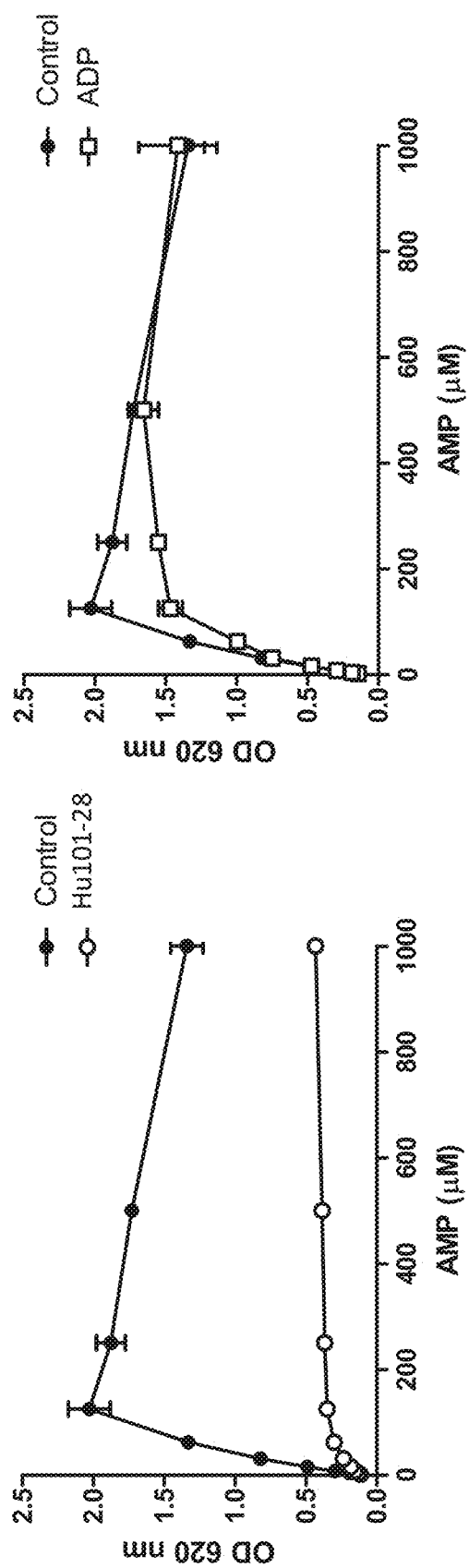
FIG. 14 shows that Hu101-28 non-competitively inhibits CD73 activity.

Further experiments showed that Hu101-28 did not compete with AMP substrate binding to the active site but acts allosterically or through other non-competitive mechanisms which is more preferred in terms of avoiding the need to compete with multiple endogenous AMP substrates. As shown in FIG. 14, increasing AMP substrate concentration did not prevent inhibition of hydrolysis by Hu101-28, indicating that Hu101-28 acted as a non-competitive inhibitor. In contrast, the inhibitory activity of ADP can be overcome by increasing the concentration of substrate to outcompete ADP binding to the active site.

Figure 15:
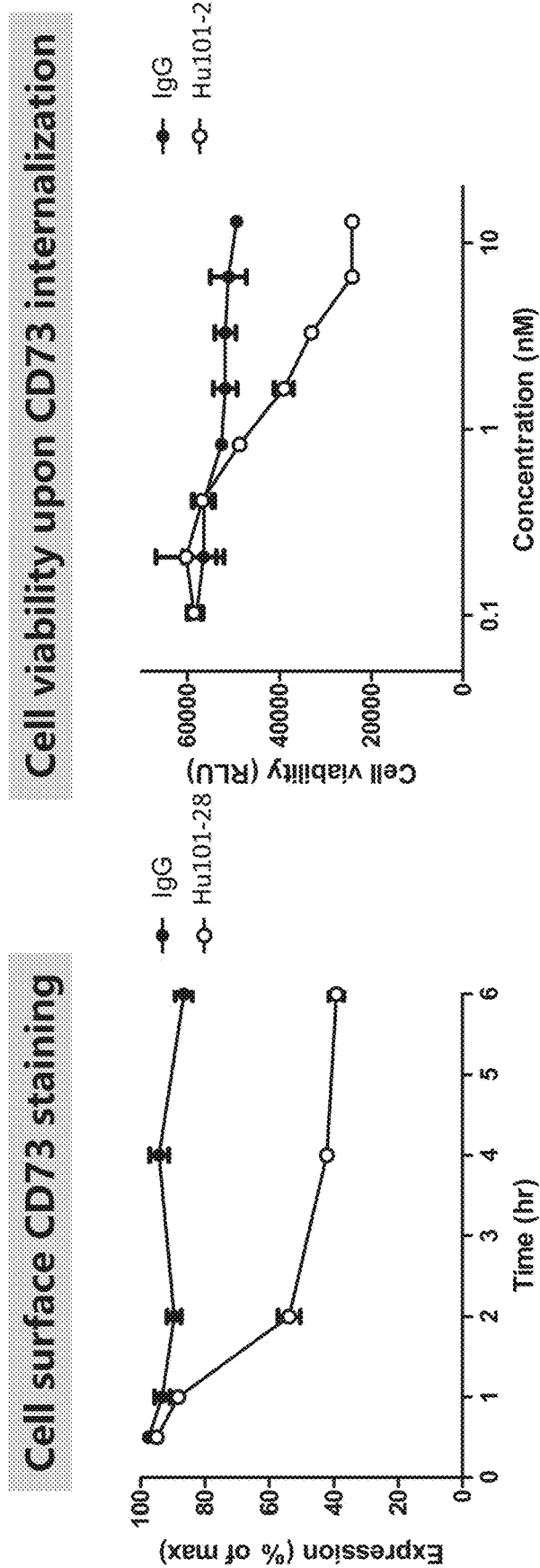
FIG. 15 shows that Hu101-28 binding to CD73 induces CD73 internalization.

A surprising and unexpected discovery is shown in FIG. 15. Internalization of CD73 upon Hu101-28 binding was demonstrated by measuring cell surface CD73 levels by flow cytometry or MDA-MB-231 cell viability following Hu309 binding in the presence of a toxin-conjugated secondary antibody. Compared to IgG which did not change the cell surface CD73 level, Hu101-28 resulted in more than half decrease of cell surface CD73 level within 6 hours (left panel), and even more significant cell killing (right panel).

The above experiments, therefore, demonstrate that Hu101-28 has dual mechanisms of action (MoA): blockage of the enzymatic activity of CD73 in a non-competitive manner and induction of the internalization of cell surface CD73.

Example 9. Hu101-28 Completely Reverses AMP or Tumor Cell-Mediated Suppression of $CD4^+$ and $CD8^+$ T Cell Responses This example shows that Hu101-28 completely reversed AMP and tumor cell-mediated suppression of $CD4^+$ and $CD8^+$ T cell responses.

Figure 16:
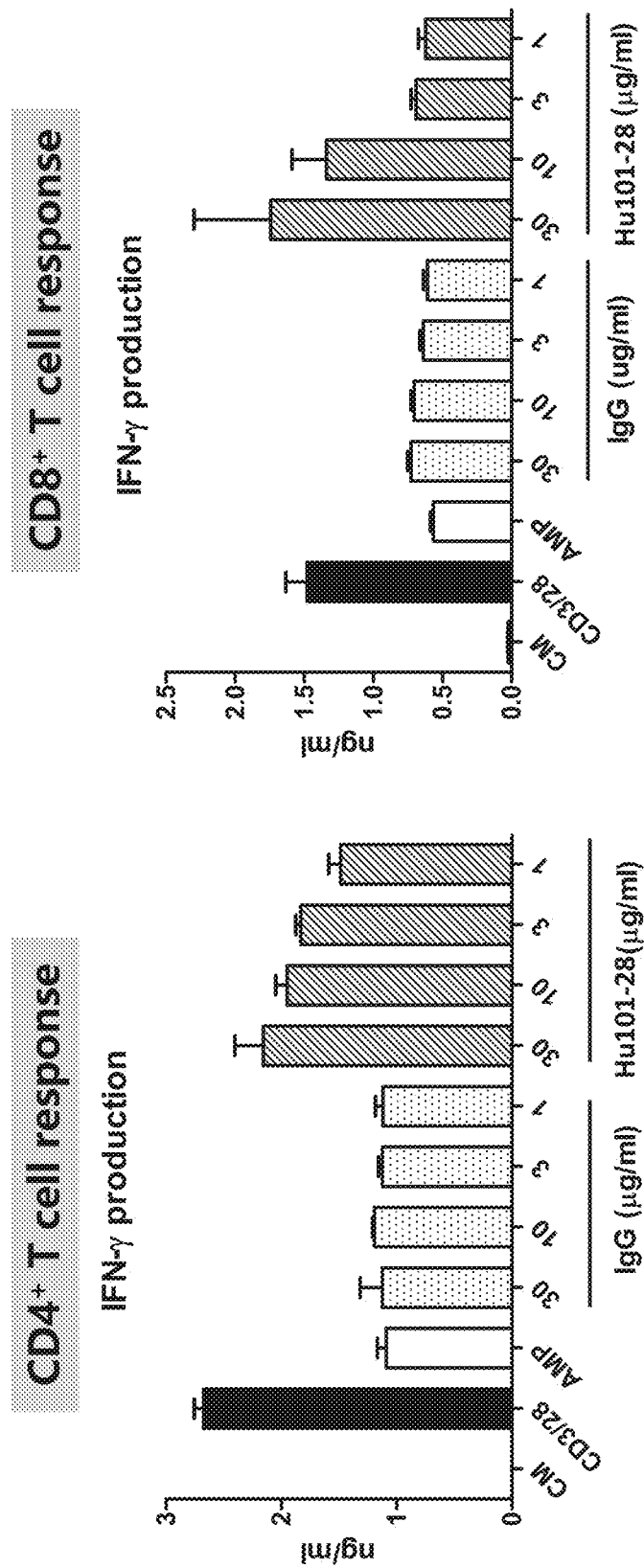
FIG. 16 shows that Hu101-28 reverses AMP-mediated suppression of T cell responses.

Human $CD4^+$ or $CD8^+$ T cells were labeled with CFSE and stimulated with anti-CD3/CD28 antibodies in the presence or absence of AMP. Hu101-28 was added into the culture for 72 hrs. The culture supernatant was analyzed for the production of IFN-g by ELISA. In FIG. 16, left panel, Hu101-28 dose-dependently increased the production of IFN-gamma in $CD4^+$ cells. Likewise, as shown in the right panel, Hu101-28 dose-dependently increased the production of IFN-gamma in $CD8^+$ cells.

Figure 17:
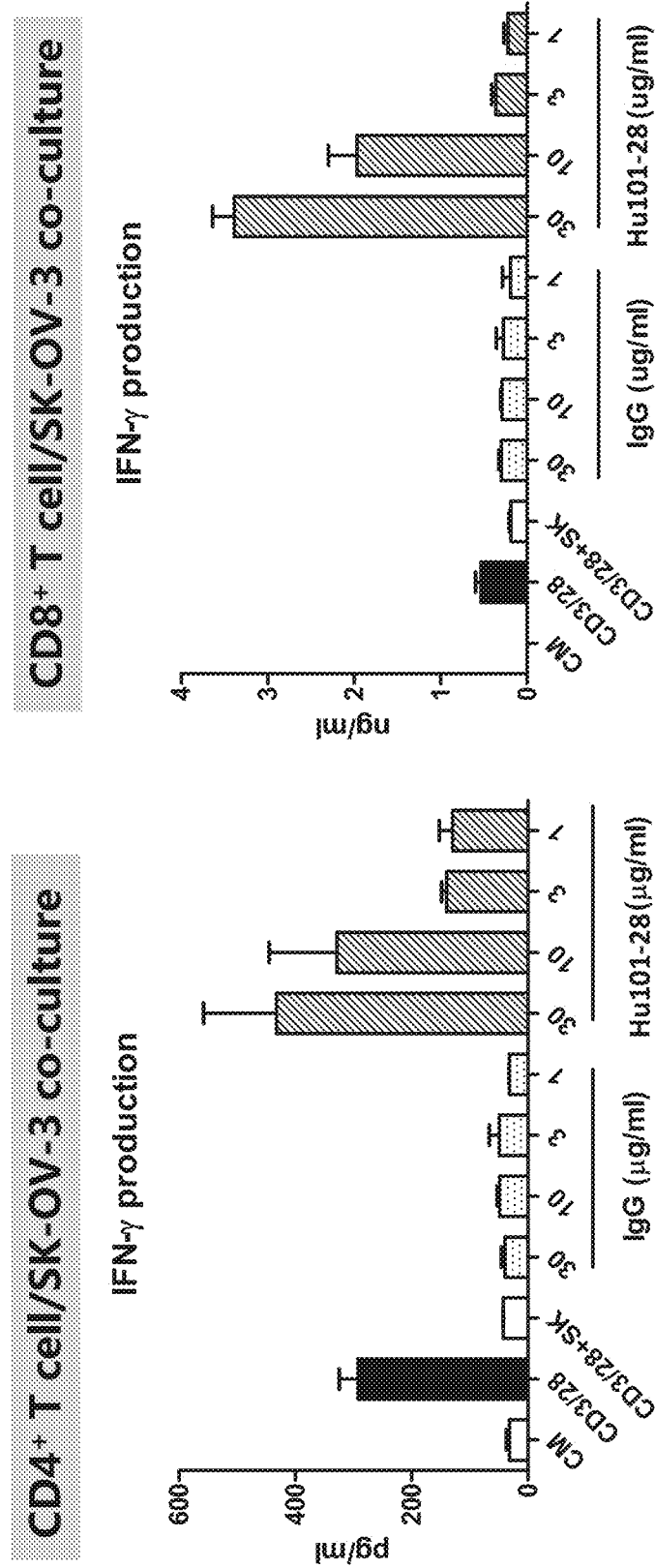
FIG. 17 shows that Hu101-28 reverses $CD73^+$ tumor cell-mediacted suppression of T cell responses.

To test the impact of Hu101-28 on tumor cell-mediated suppression of T cell response, CD73 expressing SK-OV-3 cells were treated with Mitomycin C and co-cultured with purified $CD4^+$ or $CD8^+$ T cells in the presence of anti-CD3/CD28 antibodies. Hu101-28 was added into the culture for 72 hrs and the supernatant was analyzed for the production of IFN-gamma by ELISA. As shown in FIG. 17, left panel, Hu101-28 dose-dependently increased the production of IFN-gamma in $CD4^+$ cells. Likewise, as shown in the right panel, Hu101-28 dose-dependently increased the production of IFN-gamma in $CD8^+$ cells.

Example 10. Hu101-28 Suppresses Tumor Growth

This example demonstrates that Hu101-28 is efficacious in the suppression of tumor-derived CD73 activity, leading to inhibition of tumor growth by mono- or combo-treatment.

Figure 18:
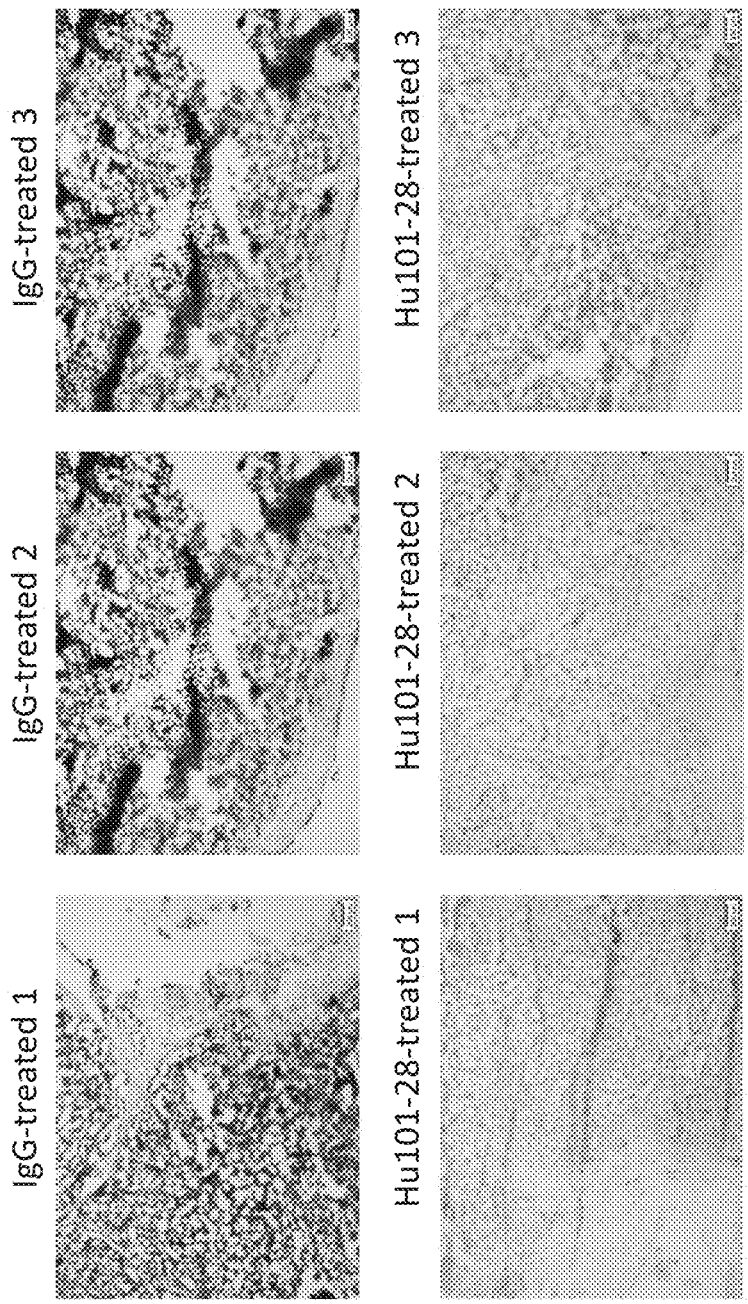
FIG. 18 presents staining image showing in vivo CD73 enzymatic inhibition by Hu101-28 in tumors of A375 xenograph model.

In vivo CD73 enzymatic activity was measured by enzyme histochemistry in tumors of A375 xenograph model and the staining results are shown in FIG. 18. A brown color indicates the presence of active CD73, whereas the lack of brown color indicates that CD73 enzymatic activity was inhibited by the antibody. The tumors from Hu101-28 or IgG control-treated A375 xenograft model were harvested and the results showed that CD73 activity in tumor sections was significantly reduced by Hu101-28 treatment compared with IgG control group.

Figure 19:
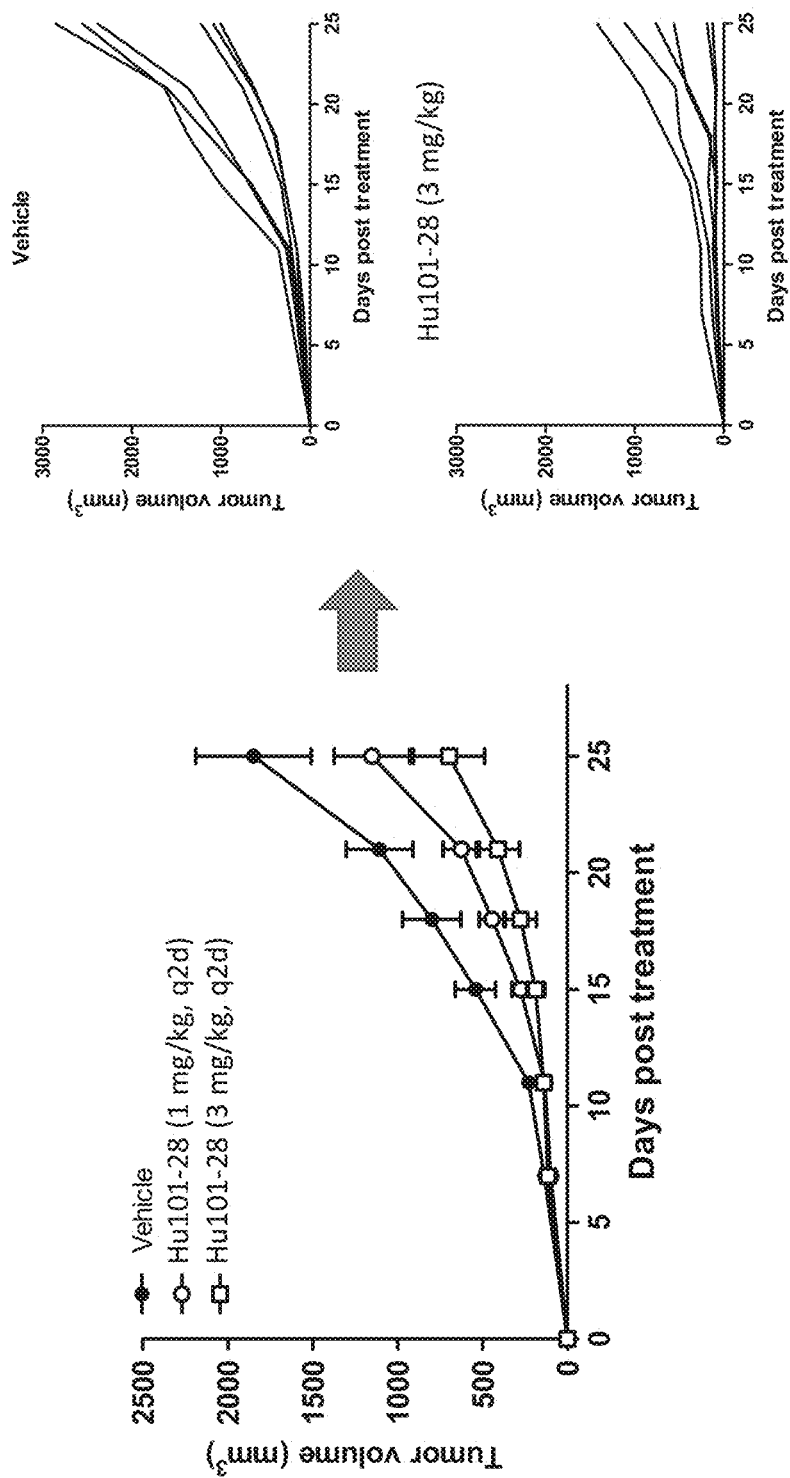
FIG. 19 shows that Hu101-28 exhibited monotherapy efficacy in tumor xenograph model.

Monotherapy efficacy of Hu101-28 was also evaluated in a tumor xenograft model. A375 melanoma cells and human PBMCs were engrafted into NSG immunodeficient mice. On the same day of engraftment, different doses of Hu101-28 or IgG control were administered to the tumor-bearing mice by intraperitoneal injection once every other day. As show in FIG. 19, Hu101-28 dose-dependently and sustainably suppressed tumor growth.

Figure 20:
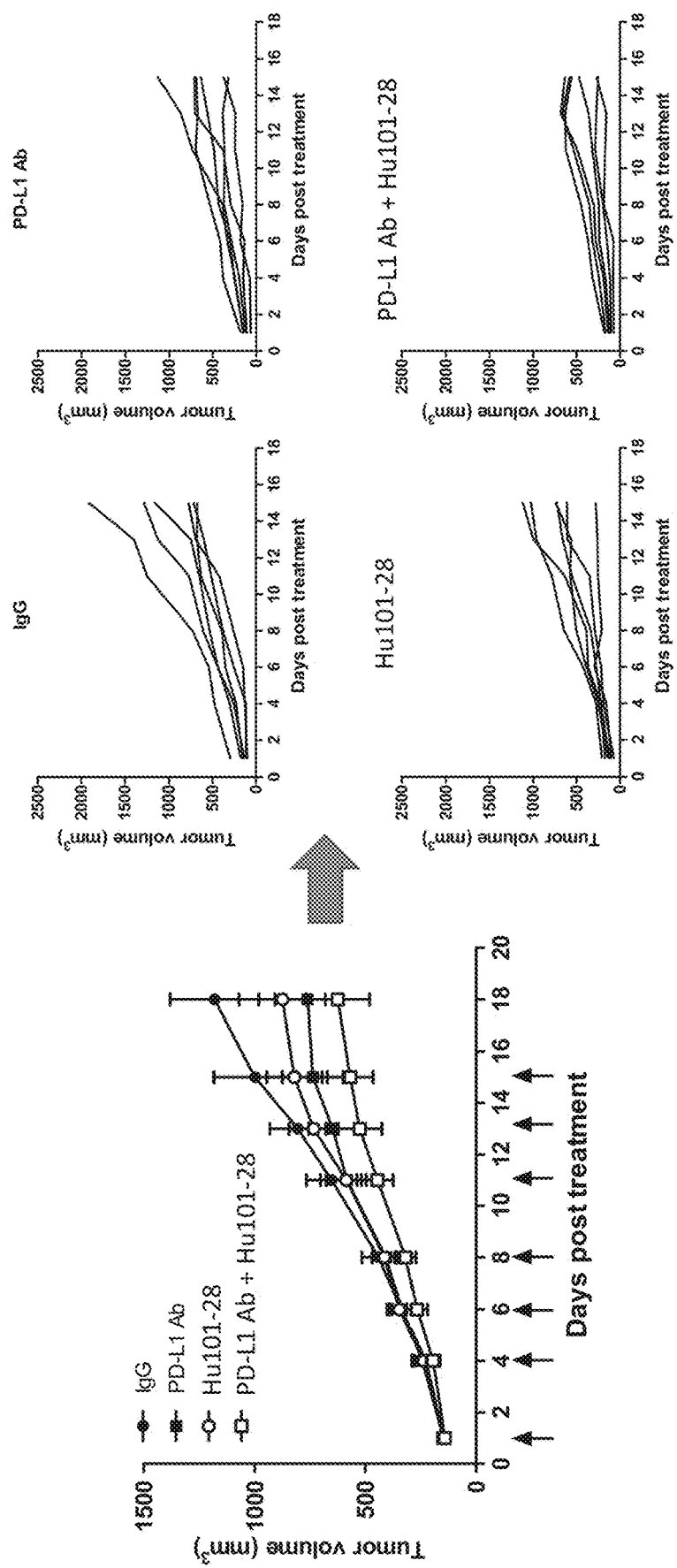
FIG. 20 shows that Hu101-28 synergizes with anti-PD-L1 antibody in inhibitin tumor growth.

The combinatory effect of Hu101-28 and an anti-PD-L1 antibody was evaluated. HCC827 cells were engrafted into NSG mice. When the tumor volume reached 100-150 $mm^3$, freshly isolated human PBMCs were administered to the tumor-bearing mice by tail vain injection and subsequently treated with IgG control, PD-L1 antibody alone, Hu101-28 alone and PD-L1 antibody plus Hu101-28 at the indicated doses every other day starting from the day of PBMCs transplantation. FIG. 20 shows synergistic effect between Hu101-28 and the anti-PD-L1 antibody.

Example 11. Hu101-28 Cross-Reacts with Cyno CD73

This example shows that humanized antibody Hu101-28 cross-reacts with cyno CD73 and exerts an acceptable PK and safety profile in the exploratory pre-clinical study.

Figure 21:
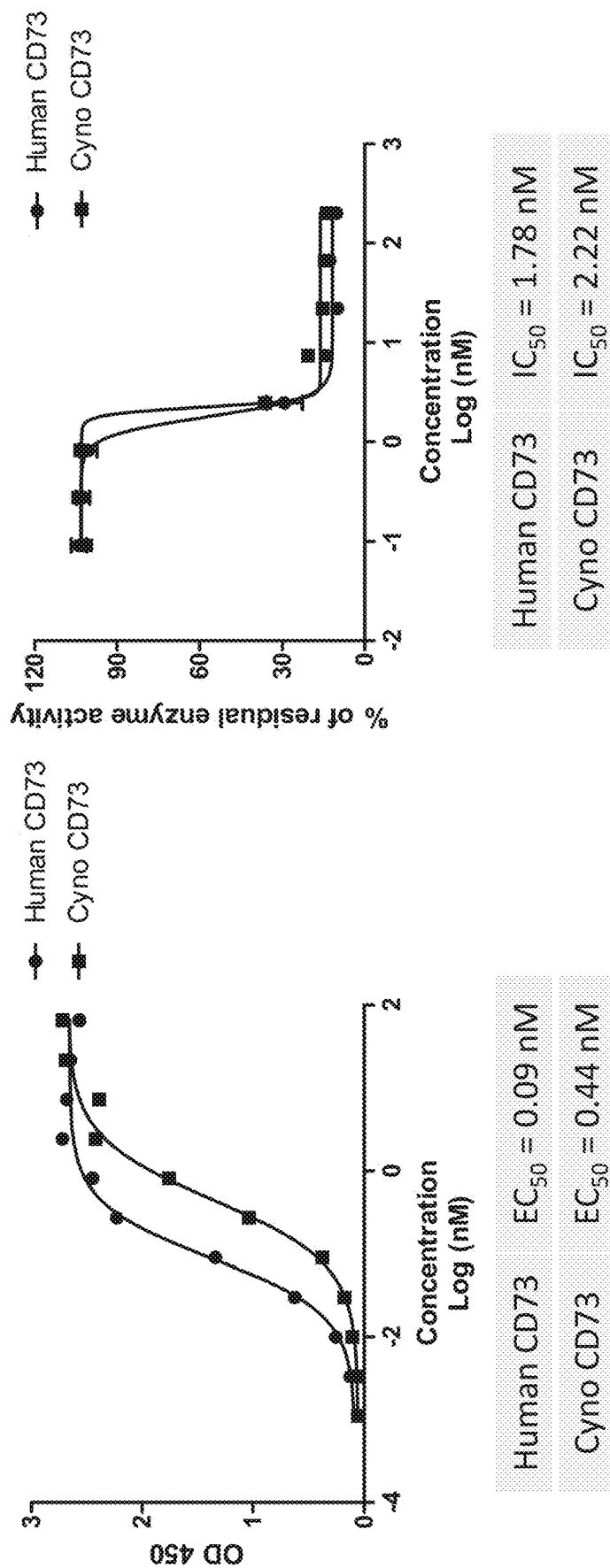
FIG. 21 shows that binding and inhibition of cyno CD73 activity by Hu101-28.

FIG. 21 shows the binding and inhibition of cyno CD73 activity by Hu101-28. Hu101-28 exerted comparable potency in the binding and inhibition of cyno CD73 activity as compared with that of human CD73 through the in vitro biochemical assay while there is no binding of Hu101-28 to rodent CD73. This results support the use of cyno monkey for the non-clinical study model to evaluate the toxicity, PK and TK of Hu101-28.

Example 12. Hu101-28 Binds to C-Terminal Domains to CD73

This example shows that one of the humanized antibodies, Hu101-28, binds to the C-terminal domains of the CD73 protein which differs from known anti-CD-73 antibodies that bind to the N-terminal domains.

Figure 22:
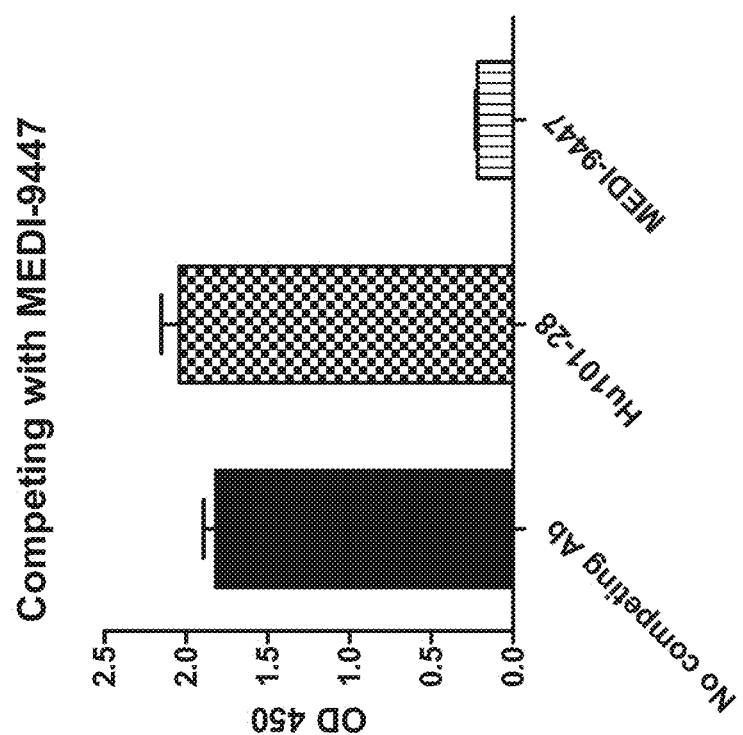
FIG. 22 shows that Hu101-28 does not compete with MEDI-9447 for binding to CD73.

The epitope binning of CD73 antibodies was assessed by competition ELISA. CD73 ECD protein and Hu101-28 were pre-incubated and then added with biotinylated MEDI-9447 (Medimmune) detected by a streptavidin-HRP antibody. The results showed that addition of biotinylated R9447 did not compete with the binding of Hu101-28 indicating both antibodies were placed in non-overlapping epitope bin (FIG. 22). As a control, the addition of biotinylated MEDI-9447 could compete out self-binding.

Figure 24:
FIG. 24 illustrates the epitopes of Hu101-28 and MEDI-9447.
Figure 24:
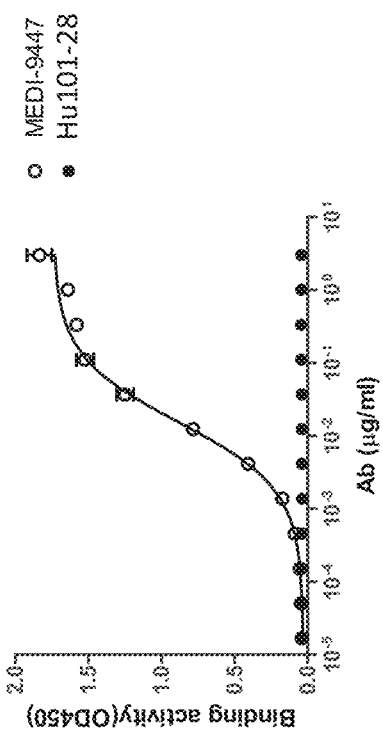
Figure 24:
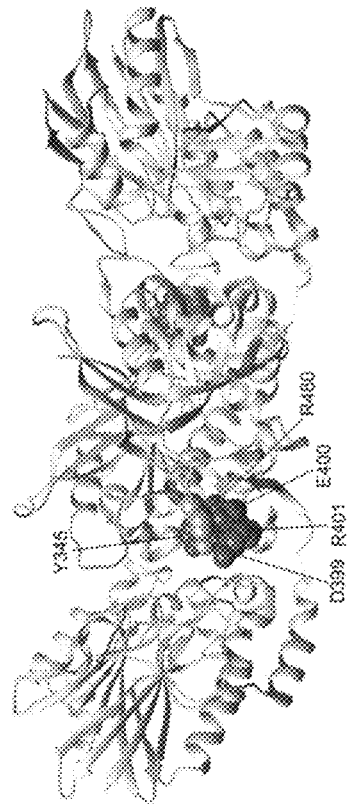
Figure 24:
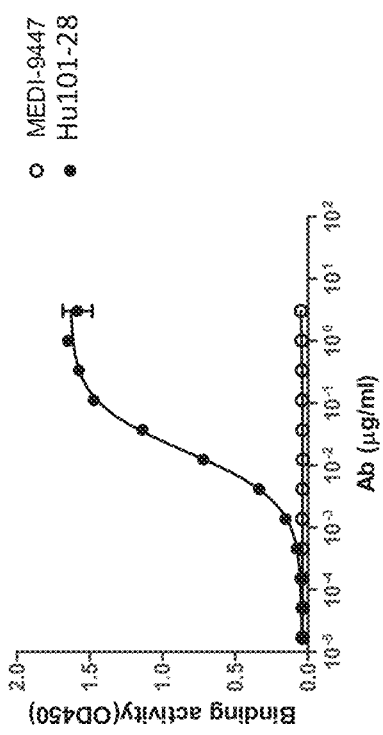

To identify the epitope of Hu101-28, a library of clones of single amino acid-mutated CD73 variants was made. Binding of Hu101-28 Fab to each variant in the library was determined, in duplicate, by high-throughput flow cytometry. For each CD73 variant, the mean binding value was plotted as a function of CD73 expression (represented by control reactivity) on chart and critical residues were identified from the chart. Critical residues for CD73 Fab binding (outlined in red) were identified as those whose mutations were negative for test Fab binding, but positive for the control MAbs. The mean binding reactivities (and ranges) are listed for the critical residues identified in the screens, and are shown in FIG. 23. Hu309 binds to the C-terminal of CD73 at the epitope of Y345, D399, E400, R401 and R480 (visualized in FIG. 24, upper left panel) while MEDI-9447 binds to the N-terminal (see comparison in FIG. 24).

Figure 25:
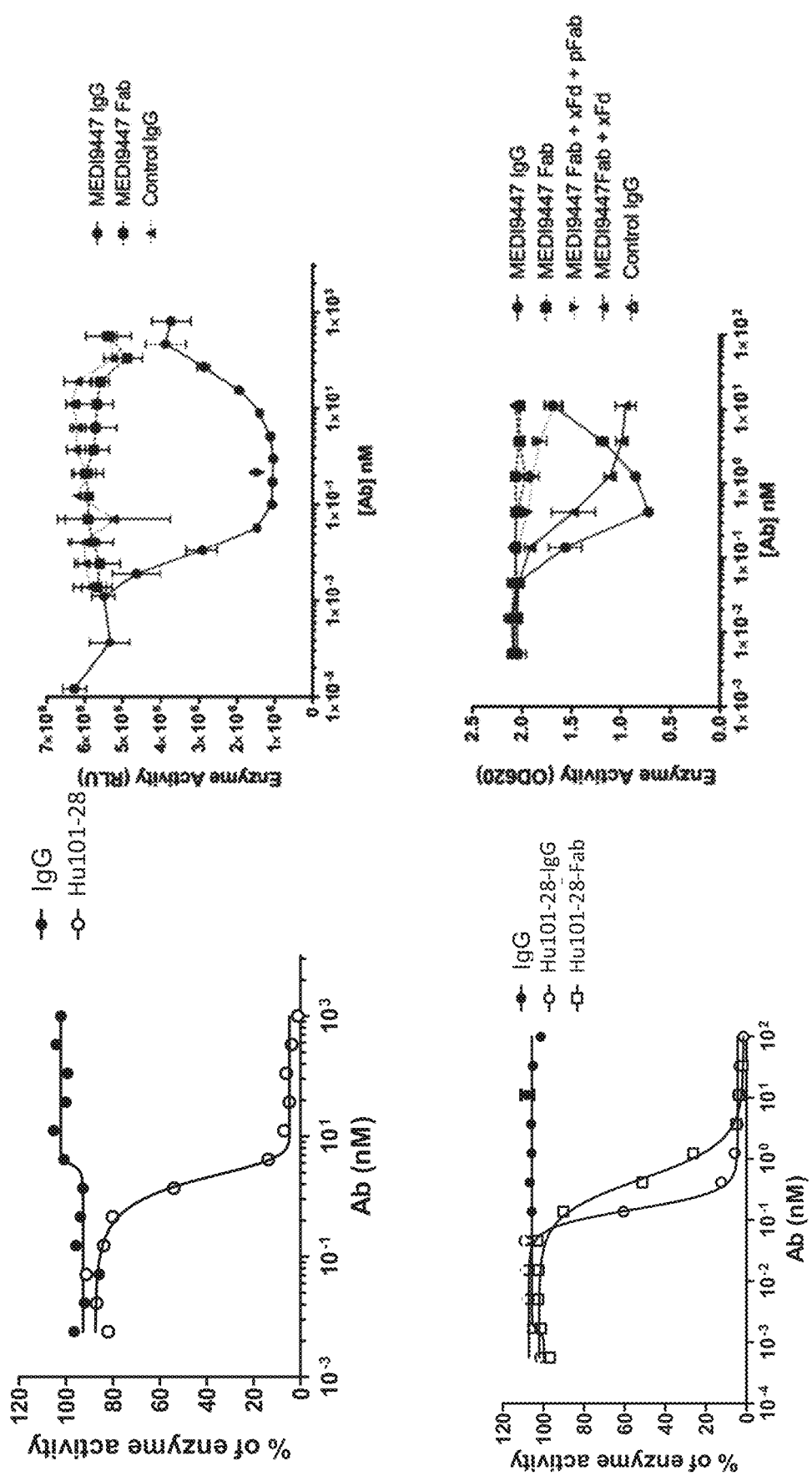
FIG. 25 shows the superior activities of Hu101-28 as compared to MEDI-9447.

It was contemplated that the unique binding property of Hu101-28 gave rise to its superior CD73 inhibition profile as compared to known antibodies. This was demonstrated in FIG. 25. The upper comparison shows that Hu101-28 exhibited a complete inhibition of CD73 activity with no "hook effect" while MEDI-9447 demonstrated a significant "hook effect" at the high doses. In the lower comparison panel, Hu101-28 Fab exhibited a comparable potency in the CD73 activity inhibition with full IgG while MEDI-9447 Fab did not inhibit soluble CD73.

Figure 26:
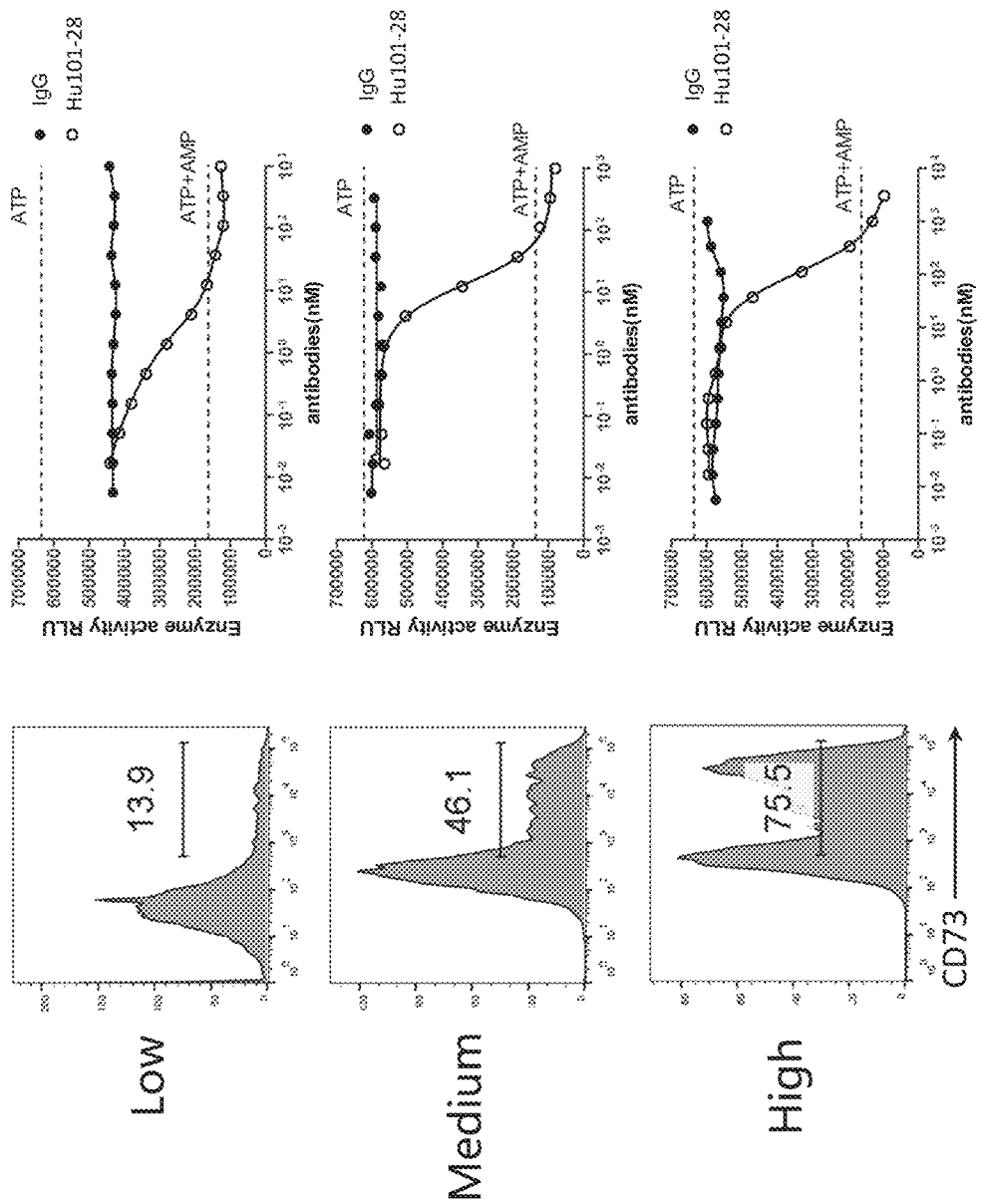
FIG. 26 shows that Hu101-28 was effective in inhibiting CD73 on cells with different expression levels of CD73.

This suggests that CD73 inhibition requires binding of both binding sites on a full. MEDI-9447 antibody while a monovalent binding by Hu101-28 is sufficient. It was hypothesized that MEDI-9447 binds to two different CD73 dimers to exert its inhibitory activity and Hu101-28 does not have such a requirement. To test this hypothesis, the inhibitory effect of Hu101-28 was tested with cells having different levels of CD73 expression. As shown in FIG. 26, Hu101-28 was able to reach complete inhibition of CD73 activity on cells which express different levels of CD73 on the surface, including those having low expression where CD73 molecules were likely distant from one another.

The present disclosure is not to be limited in scope by the specific embodiments described which are intended as single illustrations of individual aspects of the disclosure, and any compositions or methods which are functionally equivalent are within the scope of this disclosure. It will be apparent to those skilled in the art that various modifications and variations can be made in the methods and compositions of the present disclosure without departing from the spirit or scope of the disclosure. Thus, it is intended that the present disclosure cover the modifications and variations of this disclosure provided they come within the scope of the appended claims and their equivalents.

All publications and patent applications mentioned in this specification are herein incorporated by reference to the same extent as if each individual publication or patent application was specifically and individually indicated to be incorporated by reference.

What is claimed is:

1. A method of treating cancer in a patient in need thereof, comprising administering to the patient an antibody or fragment thereof of, wherein the antibody or fragment thereof has specificity to a human CD73 protein and comprises a VH CDR1 comprising the amino acid sequence of SEQ ID NO: 1, a VH CDR2 comprising the amino acid sequence of SEQ ID NO: 2, a VH CDR3 comprising the amino acid sequence of SEQ ID NO: 3, a VL CDR1 comprising the amino acid sequence of SEQ ID NO: 4, a VL CDR2 comprising the amino acid sequence of SEQ ID NO: 5, and a VL CDR3 comprising the amino acid sequence of SEQ ID NO: 6.

2. The method of claim 1, wherein the cancer is selected from the group consisting of bladder cancer, breast cancer, colorectal cancer, endometrial cancer, esophageal cancer, head and neck cancer, kidney cancer, leukemia, liver cancer, lung cancer, lymphoma, melanoma, pancreatic cancer, prostate cancer, and thyroid cancer.

3. The method of claim 1, wherein the cancer is a solid tumor.

4. The method of claim 1, further comprising administering to the patient a second cancer therapeutic agent.

5. The method of claim 4, wherein the second cancer therapeutic agent is an immune checkpoint inhibitor.

6. The method of claim 5, wherein the inhibitor inhibits the expression or activity of programmed cell death protein 1 (PD-1), programmed death-ligand 1 (PD-L1), cytotoxic T-lymphocyte-associated protein 4 (CTLA-4), lymphocyte-activation protein 3 (LAG-3), or combinations thereof.

7. The method of claim 6, wherein the inhibitor is an anti-PD-1 or anti-PD-L1 antibody.

8. The method of claim 7, wherein the inhibitor is selected from the group consisting of pembrolizumab, nivolumab, J43, RMP1-14, atezolizumab, ipilimumab, and combinations thereof.

9. The method of claim 1, wherein the antibody or fragment thereof is a humanized antibody.

10. The method of claim 1, wherein the antibody or fragment thereof comprises a heavy chain variable region comprising an amino acid sequence selected from the group consisting of SEQ ID NO: 7 and 9-13, or a peptide having at least 90% sequence identity to an amino acid sequence selected from the group consisting of SEQ ID NO: 7 and 9-13.

11. The method of claim 10, wherein the heavy chain variable region comprises the amino acid sequence of SEQ ID NO: 7 or 9.

12. The method of claim 1, wherein the antibody or fragment thereof comprises a light chain variable region comprising an amino acid sequence selected from the group consisting of SEQ ID NO: 8, 15-20 and 22-24, or a peptide having at least 90% sequence identity to an amino acid sequence selected from the group consisting of SEQ ID NO: 8, 15-20 and 22-24.

13. The method of claim 12, wherein the light chain variable region comprises the amino acid sequence of SEQ ID NO: 8.

14. A method of treating cancer in a patient in need thereof, comprising administering to the patient an antibody or fragment thereof that has specificity to a human CD73 protein and comprises a heavy chain variable region comprising the amino acid sequence of SEQ ID NO: 7 or 9 and a light chain variable region comprising the amino acid sequence of SEQ ID NO: 8.

* * * * *

SEQUENCE LISTING

<160> NUMBER OF SEQ ID NOS: 61

<210> SEQ ID NO 1
<211> LENGTH: 6
<212> TYPE: PRT
<213> ORGANISM: Artificial Sequence
<220> FEATURE:
<223> OTHER INFORMATION: Synthetic

```
<400> SEQUENCE: 1

Ser Gly Tyr Tyr Trp Asn
1               5

<210> SEQ ID NO 2
<211> LENGTH: 16
<212> TYPE: PRT
<213> ORGANISM: Artificial Sequence
<220> FEATURE:
<223> OTHER INFORMATION: Synthetic

<400> SEQUENCE: 2

Tyr Ile Asn Tyr Gly Gly Ser Asn Gly Tyr Asn Pro Ser Leu Lys Ser
1               5                   10                  15

<210> SEQ ID NO 3
<211> LENGTH: 11
<212> TYPE: PRT
<213> ORGANISM: Artificial Sequence
<220> FEATURE:
<223> OTHER INFORMATION: Synthetic

<400> SEQUENCE: 3

Asp Tyr Asp Ala Tyr Tyr Glu Ala Leu Asp Asp
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic

<400> SEQUENCE: 4

Arg Ala Ser Ser Arg Val Asn Tyr Met His
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic

<400> SEQUENCE: 5

Ala Thr Ser Asn Leu Ala Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic

<400> SEQUENCE: 6

Gln Gln Trp Ser Ser Asn Pro Pro Thr
1               5

<210> SEQ ID NO 7
<211> LENGTH: 120
<212> TYPE: PRT
<213> ORGANISM: Artificial Sequence
<220> FEATURE:
<223> OTHER INFORMATION: Synthetic

<400> SEQUENCE: 7
```

Glu Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Thr Ser Gly
            20                  25                  30

Tyr Tyr Trp Asn Trp Ile Arg Gln Pro Pro Gly Lys Lys Leu Glu Trp
                35                  40                  45

Met Gly Tyr Ile Asn Tyr Gly Gly Ser Asn Gly Tyr Asn Pro Ser Leu
    50                  55                  60

Lys Ser Arg Ile Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Tyr Asp Ala Tyr Tyr Glu Ala Leu Asp Asp Trp Gly Gln
            100                 105                 110

Gly Thr Thr Val Thr Val Ser Ser
            115                 120

<210> SEQ ID NO 8
<211> LENGTH: 106
<212> TYPE: PRT
<213> ORGANISM: Artificial Sequence
<220> FEATURE:
<223> OTHER INFORMATION: Synthetic

<400> SEQUENCE: 8

Glu Ile Val Leu Ser Gln Ser Pro Ala Thr Leu Ser Leu Ser Pro Gly
1               5                   10                  15

Glu Arg Ala Thr Leu Ser Cys Arg Ala Ser Ser Arg Val Asn Tyr Met
            20                  25                  30

His Trp Tyr Gln Gln Lys Pro Gly Gln Ser Pro Arg Pro Trp Ile Ser
                35                  40                  45

Ala Thr Ser Asn Leu Ala Ser Gly Val Pro Ala Arg Phe Ser Gly Ser
    50                  55                  60

Gly Ser Gly Thr Ser Tyr Thr Leu Thr Ile Ser Ser Leu Glu Pro Glu
65                  70                  75                  80

Asp Phe Ala Val Tyr Tyr Cys Gln Gln Trp Ser Ser Asn Pro Pro Thr
                85                  90                  95

Phe Gly Gly Gly Thr Lys Val Glu Ile Lys
            100                 105

<210> SEQ ID NO 9
<211> LENGTH: 120
<212> TYPE: PRT
<213> ORGANISM: Artificial Sequence
<220> FEATURE:
<223> OTHER INFORMATION: Synthetic

<400> SEQUENCE: 9

Glu Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Asn Trp Ile Arg Gln Pro Pro Gly Lys Gly Leu Glu Trp
                35                  40                  45

Ile Gly Tyr Ile Asn Tyr Gly Gly Ser Asn Gly Tyr Asn Pro Ser Leu
    50                  55                  60

Lys Ser Arg Val Thr Ile Ser Arg Asp Thr Ser Lys Asn Gln Phe Ser

```
                 65                  70                  75                  80
Leu Lys Leu Ser Ser Val Thr Ala Ala Asp Thr Ala Val Tyr Tyr Cys
                 85                  90                  95

Ala Arg Asp Tyr Asp Ala Tyr Tyr Glu Ala Leu Asp Asp Trp Gly Gln
                100                 105                 110

Gly Thr Thr Val Thr Val Ser Ser
            115                 120

<210> SEQ ID NO 10
<211> LENGTH: 120
<212> TYPE: PRT
<213> ORGANISM: Artificial Sequence
<220> FEATURE:
<223> OTHER INFORMATION: Synthetic

<400> SEQUENCE: 10

Asp Val Gln Leu Gln Glu Ser Gly Pro Gly Leu Val Lys Pro Ser Gln
1               5                  10                  15

Ser Leu Ser Leu Thr Cys Ser Val Thr Gly Tyr Ser Ile Thr Ser Gly
                 20                  25                  30

Tyr Tyr Trp Asn Trp Ile Arg Gln Phe Pro Gly Asn Lys Leu Glu Trp
                 35                  40                  45

Met Gly Tyr Ile Asn Tyr Gly Gly Ser Asn Gly Tyr Asn Pro Ser Leu
         50                  55                  60

Lys Ser Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                 85                  90                  95

Ala Arg Asp Tyr Asp Ala Tyr Tyr Glu Ala Leu Asp Asp Trp Gly Gln
                100                 105                 110

Gly Thr Ser Val Thr Val Ser Ser
            115                 120

<210> SEQ ID NO 11
<211> LENGTH: 120
<212> TYPE: PRT
<213> ORGANISM: Artificial Sequence
<220> FEATURE:
<223> OTHER INFORMATION: Synthetic

<400> SEQUENCE: 11

Glu Val Gln Leu Gln Glu Ser Gly Pro Gly Leu Val Lys Pro Ser Glu
1               5                  10                  15

Thr Leu Ser Leu Thr Cys Ala Val Ser Gly Tyr Ser Ile Ser Ser Gly
                 20                  25                  30

Tyr Tyr Trp Asn Trp Ile Arg Gln Pro Pro Gly Lys Gly Leu Glu Trp
                 35                  40                  45

Ile Gly Tyr Ile Asn Tyr Gly Gly Ser Asn Gly Tyr Asn Pro Ser Leu
         50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                 85                  90                  95

Ala Arg Asp Tyr Asp Ala Tyr Tyr Glu Ala Leu Asp Asp Trp Gly Gln
                100                 105                 110

Gly Thr Thr Val Thr Val Ser Ser
            115                 120
```

```
<210> SEQ ID NO 12
<211> LENGTH: 120
<212> TYPE: PRT
<213> ORGANISM: Artificial Sequence
<220> FEATURE:
<223> OTHER INFORMATION: Synthetic

<400> SEQUENCE: 12

Glu Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Asn Trp Ile Arg Gln Pro Pro Gly Lys Gly Leu Glu Trp
        35                  40                  45

Ile Gly Tyr Ile Asn Tyr Gly Gly Ser Asn Gly Tyr Asn Pro Ser Leu
    50                  55                  60

Lys Ser Arg Ile Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Tyr Asp Ala Tyr Tyr Glu Ala Leu Asp Asp Trp Gly Gln
            100                 105                 110

Gly Thr Thr Val Thr Val Ser Ser
        115                 120

<210> SEQ ID NO 13
<211> LENGTH: 120
<212> TYPE: PRT
<213> ORGANISM: Artificial Sequence
<220> FEATURE:
<223> OTHER INFORMATION: Synthetic

<400> SEQUENCE: 13

Glu Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Asn Trp Ile Arg Gln Pro Pro Gly Lys Gly Leu Glu Trp
        35                  40                  45

Met Gly Tyr Ile Asn Tyr Gly Gly Ser Asn Gly Tyr Asn Pro Ser Leu
    50                  55                  60

Lys Ser Arg Ile Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Tyr Asp Ala Tyr Tyr Glu Ala Leu Asp Asp Trp Gly Gln
            100                 105                 110

Gly Thr Thr Val Thr Val Ser Ser
        115                 120

<210> SEQ ID NO 14
<211> LENGTH: 109
<212> TYPE: PRT
<213> ORGANISM: Artificial Sequence
<220> FEATURE:
<223> OTHER INFORMATION: Synthetic

<400> SEQUENCE: 14

Gln Val Gln Leu Gln Glu Ser Gly Pro Gly Leu Val Lys Pro Ser Glu
```

```
                1               5                  10                 15
            Thr Leu Ser Leu Thr Cys Ala Val Ser Gly Tyr Ser Ile Ser Ser Gly
                        20                  25                 30

Tyr Tyr Trp Gly Trp Ile Arg Gln Pro Pro Gly Lys Gly Leu Glu Trp
                        35                  40                 45

Ile Gly Ser Ile Tyr His Ser Gly Ser Thr Tyr Tyr Asn Pro Ser Leu
                50                  55                 60

Lys Ser Arg Val Thr Ile Ser Val Asp Thr Ser Lys Asn Gln Phe Ser
             65                 70                  75                 80

Leu Lys Leu Ser Ser Val Thr Ala Ala Asp Thr Ala Val Tyr Tyr Cys
                            85                  90                 95

Ala Arg Trp Gly Gln Gly Thr Thr Val Thr Val Ser Ser
                            100                 105

<210> SEQ ID NO 15
<211> LENGTH: 106
<212> TYPE: PRT
<213> ORGANISM: Artificial Sequence
<220> FEATURE:
<223> OTHER INFORMATION: Synthetic

<400> SEQUENCE: 15

Gln Ile Val Leu Ser Gln Ser Pro Ala Ile Leu Ser Ala Ser Pro Gly
            1               5                  10                 15

Glu Lys Val Thr Met Thr Cys Arg Ala Ser Ser Arg Val Asn Tyr Met
                        20                  25                 30

His Trp Tyr Gln Gln Lys Pro Gly Ser Ser Pro Lys Pro Trp Ile Ser
                        35                  40                 45

Ala Thr Ser Asn Leu Ala Ser Gly Val Pro Ala Arg Phe Ser Gly Ser
                50                  55                 60

Gly Ser Gly Thr Ser Tyr Ser Leu Thr Ile Ser Arg Val Glu Thr Glu
             65                 70                  75                 80

Asp Ala Ala Thr Tyr Tyr Cys Gln Gln Trp Ser Asn Pro Pro Thr
                            85                  90                 95

Phe Gly Gly Gly Thr Lys Leu Glu Ile Lys
                            100                 105

<210> SEQ ID NO 16
<211> LENGTH: 106
<212> TYPE: PRT
<213> ORGANISM: Artificial Sequence
<220> FEATURE:
<223> OTHER INFORMATION: Synthetic

<400> SEQUENCE: 16

Glu Ile Val Leu Thr Gln Ser Pro Asp Phe Gln Ser Val Thr Pro Lys
            1               5                  10                 15

Glu Lys Val Thr Ile Thr Cys Arg Ala Ser Ser Arg Val Asn Tyr Met
                        20                  25                 30

His Trp Tyr Gln Gln Lys Pro Asp Gln Ser Pro Lys Leu Leu Ile Lys
                        35                  40                 45

Ala Thr Ser Asn Leu Ala Ser Gly Val Pro Ser Arg Phe Ser Gly Ser
                50                  55                 60

Gly Ser Gly Thr Asp Phe Thr Leu Thr Ile Asn Ser Leu Glu Ala Glu
             65                 70                  75                 80

Asp Ala Ala Thr Tyr Tyr Cys Gln Gln Trp Ser Asn Pro Pro Thr
                            85                  90                 95
```

Phe Gly Gly Gly Thr Lys Val Glu Ile Lys
            100                 105

<210> SEQ ID NO 17
<211> LENGTH: 106
<212> TYPE: PRT
<213> ORGANISM: Artificial Sequence
<220> FEATURE:
<223> OTHER INFORMATION: Synthetic

<400> SEQUENCE: 17

Glu Ile Val Leu Thr Gln Ser Pro Asp Phe Gln Ser Val Thr Pro Lys
1               5                   10                  15

Glu Lys Val Thr Ile Thr Cys Arg Ala Ser Ser Arg Val Asn Tyr Met
            20                  25                  30

His Trp Tyr Gln Gln Lys Pro Asp Gln Ser Pro Lys Leu Leu Ile Lys
        35                  40                  45

Ala Thr Ser Asn Leu Ala Ser Gly Val Pro Ser Arg Phe Ser Gly Ser
    50                  55                  60

Gly Ser Gly Thr Ser Tyr Thr Leu Thr Ile Asn Ser Leu Glu Ala Glu
65                  70                  75                  80

Asp Ala Ala Thr Tyr Tyr Cys Gln Gln Trp Ser Ser Asn Pro Pro Thr
                85                  90                  95

Phe Gly Gly Gly Thr Lys Val Glu Ile Lys
            100                 105

<210> SEQ ID NO 18
<211> LENGTH: 106
<212> TYPE: PRT
<213> ORGANISM: Artificial Sequence
<220> FEATURE:
<223> OTHER INFORMATION: Synthetic

<400> SEQUENCE: 18

Glu Ile Val Leu Thr Gln Ser Pro Asp Phe Gln Ser Val Thr Pro Lys
1               5                   10                  15

Glu Lys Val Thr Ile Thr Cys Arg Ala Ser Ser Arg Val Asn Tyr Met
            20                  25                  30

His Trp Tyr Gln Gln Lys Pro Asp Gln Ser Pro Lys Leu Leu Ile Ser
        35                  40                  45

Ala Thr Ser Asn Leu Ala Ser Gly Val Pro Ser Arg Phe Ser Gly Ser
    50                  55                  60

Gly Ser Gly Thr Ser Tyr Thr Leu Thr Ile Asn Ser Leu Glu Ala Glu
65                  70                  75                  80

Asp Ala Ala Thr Tyr Tyr Cys Gln Gln Trp Ser Ser Asn Pro Pro Thr
                85                  90                  95

Phe Gly Gly Gly Thr Lys Val Glu Ile Lys
            100                 105

<210> SEQ ID NO 19
<211> LENGTH: 106
<212> TYPE: PRT
<213> ORGANISM: Artificial Sequence
<220> FEATURE:
<223> OTHER INFORMATION: Synthetic

<400> SEQUENCE: 19

Glu Ile Val Leu Thr Gln Ser Pro Asp Phe Gln Ser Val Thr Pro Lys
1               5                   10                  15

Glu Lys Val Thr Ile Thr Cys Arg Ala Ser Ser Arg Val Asn Tyr Met

```
                20                  25                  30

His Trp Tyr Gln Gln Lys Pro Asp Gln Ser Pro Lys Pro Trp Ile Ser
            35                  40                  45

Ala Thr Ser Asn Leu Ala Ser Gly Val Pro Ser Arg Phe Ser Gly Ser
    50                  55                  60

Gly Ser Gly Thr Ser Tyr Thr Leu Thr Ile Asn Ser Leu Glu Ala Glu
65                  70                  75                  80

Asp Ala Ala Thr Tyr Tyr Cys Gln Gln Trp Ser Ser Asn Pro Pro Thr
                85                  90                  95

Phe Gly Gly Gly Thr Lys Val Glu Ile Lys
            100                 105

<210> SEQ ID NO 20
<211> LENGTH: 106
<212> TYPE: PRT
<213> ORGANISM: Artificial Sequence
<220> FEATURE:
<223> OTHER INFORMATION: Synthetic

<400> SEQUENCE: 20

Glu Ile Val Leu Ser Gln Ser Pro Asp Phe Gln Ser Val Thr Pro Lys
1               5                   10                  15

Glu Lys Val Thr Ile Thr Cys Arg Ala Ser Ser Arg Val Asn Tyr Met
                20                  25                  30

His Trp Tyr Gln Gln Lys Pro Asp Gln Ser Pro Lys Pro Trp Ile Ser
            35                  40                  45

Ala Thr Ser Asn Leu Ala Ser Gly Val Pro Ser Arg Phe Ser Gly Ser
    50                  55                  60

Gly Ser Gly Thr Ser Tyr Thr Leu Thr Ile Asn Ser Leu Glu Ala Glu
65                  70                  75                  80

Asp Ala Ala Thr Tyr Tyr Cys Gln Gln Trp Ser Ser Asn Pro Pro Thr
                85                  90                  95

Phe Gly Gly Gly Thr Lys Val Glu Ile Lys
            100                 105

<210> SEQ ID NO 21
<211> LENGTH: 98
<212> TYPE: PRT
<213> ORGANISM: Artificial Sequence
<220> FEATURE:
<223> OTHER INFORMATION: Synthetic

<400> SEQUENCE: 21

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
                20                  25                  30

Leu His Trp Tyr Gln Gln Lys Pro Asp Gln Ser Pro Lys Leu Leu Ile
            35                  40                  45

Lys Tyr Ala Ser Gln Ser Phe Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Phe Gly Gly Gly Thr Lys Val Glu
                85                  90                  95

Ile Lys
```

```
<210> SEQ ID NO 22
<211> LENGTH: 106
<212> TYPE: PRT
<213> ORGANISM: Artificial Sequence
<220> FEATURE:
<223> OTHER INFORMATION: Synthetic

<400> SEQUENCE: 22

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Arg Val Asn Tyr Met
            20                  25                  30

His Trp Tyr Gln Gln Lys Pro Gly Gln Ala Pro Arg Leu Leu Ile Tyr
        35                  40                  45

Ala Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Trp Ser Ser Asn Pro Pro Thr
                85                  90                  95

Phe Gly Gly Gly Thr Lys Val Glu Ile Lys
            100                 105

<210> SEQ ID NO 23
<211> LENGTH: 106
<212> TYPE: PRT
<213> ORGANISM: Artificial Sequence
<220> FEATURE:
<223> OTHER INFORMATION: Synthetic

<400> SEQUENCE: 23

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Arg Val Asn Tyr Met
            20                  25                  30

His Trp Tyr Gln Gln Lys Pro Gly Gln Ala Pro Arg Leu Leu Ile Tyr
        35                  40                  45

Ala Thr Ser Asn Leu Ala Ser Gly Ile Pro Ala Arg Phe Ser Gly Ser
    50                  55                  60

Gly Ser Gly Thr Ser Tyr Thr Leu Thr Ile Ser Ser Leu Glu Pro Glu
65                  70                  75                  80

Asp Phe Ala Val Tyr Tyr Cys Gln Gln Trp Ser Ser Asn Pro Pro Thr
                85                  90                  95

Phe Gly Gly Gly Thr Lys Val Glu Ile Lys
            100                 105

<210> SEQ ID NO 24
<211> LENGTH: 106
<212> TYPE: PRT
<213> ORGANISM: Artificial Sequence
<220> FEATURE:
<223> OTHER INFORMATION: Synthetic

<400> SEQUENCE: 24

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Arg Val Asn Tyr Met
            20                  25                  30

His Trp Tyr Gln Gln Lys Pro Gly Gln Ala Pro Arg Leu Leu Ile Ser
        35                  40                  45
```

```
Ala Thr Ser Asn Leu Ala Ser Gly Val Pro Ala Arg Phe Ser Gly Ser
        50                  55                  60

Gly Ser Gly Thr Ser Tyr Thr Leu Thr Ile Ser Ser Leu Glu Pro Glu
 65                  70                  75                  80

Asp Phe Ala Val Tyr Tyr Cys Gln Gln Trp Ser Ser Asn Pro Pro Thr
                 85                  90                  95

Phe Gly Gly Gly Thr Lys Val Glu Ile Lys
            100                 105

<210> SEQ ID NO 25
<211> LENGTH: 98
<212> TYPE: PRT
<213> ORGANISM: Artificial Sequence
<220> FEATURE:
<223> OTHER INFORMATION: Synthetic

<400> SEQUENCE: 25

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
                 20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Phe Gly Gly Gly Thr Lys Val Glu
                 85                  90                  95

Ile Lys

<210> SEQ ID NO 26
<211> LENGTH: 6
<212> TYPE: PRT
<213> ORGANISM: Artificial Sequence
<220> FEATURE:
<223> OTHER INFORMATION: Synthetic

<400> SEQUENCE: 26

Thr Gly Tyr Tyr Trp Asn
 1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic

<400> SEQUENCE: 27

Cys Gly Tyr Tyr Trp Asn
 1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic

<400> SEQUENCE: 28
```

```
Ser Ala Tyr Tyr Trp Asn
1               5

<210> SEQ ID NO 29
<211> LENGTH: 6
<212> TYPE: PRT
<213> ORGANISM: Artificial Sequence
<220> FEATURE:
<223> OTHER INFORMATION: Synthetic

<400> SEQUENCE: 29

Ser Pro Tyr Tyr Trp Asn
1               5

<210> SEQ ID NO 30
<211> LENGTH: 16
<212> TYPE: PRT
<213> ORGANISM: Artificial Sequence
<220> FEATURE:
<223> OTHER INFORMATION: Synthetic

<400> SEQUENCE: 30

Tyr Ile Asn Tyr Gly Ala Ser Asn Gly Tyr Asn Pro Ser Leu Lys Ser
1               5                  10                  15

<210> SEQ ID NO 31
<211> LENGTH: 16
<212> TYPE: PRT
<213> ORGANISM: Artificial Sequence
<220> FEATURE:
<223> OTHER INFORMATION: Synthetic

<400> SEQUENCE: 31

Tyr Ile Asn Tyr Gly Pro Ser Asn Gly Tyr Asn Pro Ser Leu Lys Ser
1               5                  10                  15

<210> SEQ ID NO 32
<211> LENGTH: 16
<212> TYPE: PRT
<213> ORGANISM: Artificial Sequence
<220> FEATURE:
<223> OTHER INFORMATION: Synthetic

<400> SEQUENCE: 32

Tyr Ile Asn Tyr Gly Gly Thr Asn Gly Tyr Asn Pro Ser Leu Lys Ser
1               5                  10                  15

<210> SEQ ID NO 33
<211> LENGTH: 16
<212> TYPE: PRT
<213> ORGANISM: Artificial Sequence
<220> FEATURE:
<223> OTHER INFORMATION: Synthetic

<400> SEQUENCE: 33

Tyr Ile Asn Tyr Gly Gly Cys Asn Gly Tyr Asn Pro Ser Leu Lys Ser
1               5                  10                  15

<210> SEQ ID NO 34
<211> LENGTH: 16
<212> TYPE: PRT
<213> ORGANISM: Artificial Sequence
<220> FEATURE:
<223> OTHER INFORMATION: Synthetic

<400> SEQUENCE: 34

Tyr Ile Asn Tyr Gly Gly Ser Asp Gly Tyr Asn Pro Ser Leu Lys Ser
```

-continued

<210> SEQ ID NO 35
<211> LENGTH: 16
<212> TYPE: PRT
<213> ORGANISM: Artificial Sequence
<220> FEATURE:
<223> OTHER INFORMATION: Synthetic

<400> SEQUENCE: 35

Tyr Ile Asn Tyr Gly Gly Ser Glu Gly Tyr Asn Pro Ser Leu Lys Ser
1               5                   10                  15

<210> SEQ ID NO 36
<211> LENGTH: 16
<212> TYPE: PRT
<213> ORGANISM: Artificial Sequence
<220> FEATURE:
<223> OTHER INFORMATION: Synthetic

<400> SEQUENCE: 36

Tyr Ile Asn Tyr Gly Gly Ser Gln Gly Tyr Asn Pro Ser Leu Lys Ser
1               5                   10                  15

<210> SEQ ID NO 37
<211> LENGTH: 11
<212> TYPE: PRT
<213> ORGANISM: Artificial Sequence
<220> FEATURE:
<223> OTHER INFORMATION: Synthetic

<400> SEQUENCE: 37

Asp Tyr Asp Ala Tyr Tyr Asp Ala Leu Asp Asp
1               5                   10

<210> SEQ ID NO 38
<211> LENGTH: 11
<212> TYPE: PRT
<213> ORGANISM: Artificial Sequence
<220> FEATURE:
<223> OTHER INFORMATION: Synthetic

<400> SEQUENCE: 38

Asp Tyr Asp Ala Tyr Tyr Gln Ala Leu Asp Asp
1               5                   10

<210> SEQ ID NO 39
<211> LENGTH: 11
<212> TYPE: PRT
<213> ORGANISM: Artificial Sequence
<220> FEATURE:
<223> OTHER INFORMATION: Synthetic

<400> SEQUENCE: 39

Asp Tyr Asp Ala Tyr Tyr Asn Ala Leu Asp Asp
1               5                   10

<210> SEQ ID NO 40
<211> LENGTH: 11
<212> TYPE: PRT
<213> ORGANISM: Artificial Sequence
<220> FEATURE:
<223> OTHER INFORMATION: Synthetic

<400> SEQUENCE: 40

Asp Tyr Asp Ala Tyr Tyr Glu Gly Leu Asp Asp
1               5                   10

<210> SEQ ID NO 41
<211> LENGTH: 11
<212> TYPE: PRT
<213> ORGANISM: Artificial Sequence
<220> FEATURE:
<223> OTHER INFORMATION: Synthetic

<400> SEQUENCE: 41

Asp Tyr Asp Ala Tyr Tyr Glu Cys Leu Asp Asp
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Synthetic

<400> SEQUENCE: 42

Arg Ala Thr Ser Arg Val Asn Tyr Met His
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Synthetic

<400> SEQUENCE: 43

Arg Ala Cys Ser Arg Val Asn Tyr Met His
1               5                   10

<210> SEQ ID NO 44
<211> LENGTH: 10
<212> TYPE: PRT
<213> ORGANISM: Artificial Sequence
<220> FEATURE:
<223> OTHER INFORMATION: Synthetic

<400> SEQUENCE: 44

Arg Ala Ser Thr Arg Val Asn Tyr Met His
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Synthetic

<400> SEQUENCE: 45

Arg Ala Ser Cys Arg Val Asn Tyr Met His
1               5                   10

<210> SEQ ID NO 46
<211> LENGTH: 9
<212> TYPE: PRT
<213> ORGANISM: Artificial Sequence
<220> FEATURE:
<223> OTHER INFORMATION: Synthetic

<400> SEQUENCE: 46

Asn Gln Trp Ser Ser Asn Pro Pro Thr
1               5

<210> SEQ ID NO 47
<211> LENGTH: 9
<212> TYPE: PRT
<213> ORGANISM: Artificial Sequence
<220> FEATURE:
<223> OTHER INFORMATION: Synthetic

<400> SEQUENCE: 47

Asp Gln Trp Ser Ser Asn Pro Pro Thr
1               5

<210> SEQ ID NO 48
<211> LENGTH: 9
<212> TYPE: PRT
<213> ORGANISM: Artificial Sequence
<220> FEATURE:
<223> OTHER INFORMATION: Synthetic

<400> SEQUENCE: 48

Glu Gln Trp Ser Ser Asn Pro Pro Thr
1               5

<210> SEQ ID NO 49
<211> LENGTH: 9
<212> TYPE: PRT
<213> ORGANISM: Artificial Sequence
<220> FEATURE:
<223> OTHER INFORMATION: Synthetic

<400> SEQUENCE: 49

Gln Asn Trp Ser Ser Asn Pro Pro Thr
1               5

<210> SEQ ID NO 50
<211> LENGTH: 9
<212> TYPE: PRT
<213> ORGANISM: Artificial Sequence
<220> FEATURE:
<223> OTHER INFORMATION: Synthetic

<400> SEQUENCE: 50

Gln Asp Trp Ser Ser Asn Pro Pro Thr
1               5

<210> SEQ ID NO 51
<211> LENGTH: 9
<212> TYPE: PRT
<213> ORGANISM: Artificial Sequence
<220> FEATURE:
<223> OTHER INFORMATION: Synthetic

<400> SEQUENCE: 51

Gln Glu Trp Ser Ser Asn Pro Pro Thr
1               5

<210> SEQ ID NO 52
<211> LENGTH: 9
<212> TYPE: PRT
<213> ORGANISM: Artificial Sequence
<220> FEATURE:
<223> OTHER INFORMATION: Synthetic

<400> SEQUENCE: 52

Gln Gln Tyr Ser Ser Asn Pro Pro Thr
1               5

```
<210> SEQ ID NO 53
<211> LENGTH: 9
<212> TYPE: PRT
<213> ORGANISM: Artificial Sequence
<220> FEATURE:
<223> OTHER INFORMATION: Synthetic

<400> SEQUENCE: 53

Gln Gln Trp Thr Ser Asn Pro Pro Thr
1               5

<210> SEQ ID NO 54
<211> LENGTH: 9
<212> TYPE: PRT
<213> ORGANISM: Artificial Sequence
<220> FEATURE:
<223> OTHER INFORMATION: Synthetic

<400> SEQUENCE: 54

Gln Gln Trp Cys Ser Asn Pro Pro Thr
1               5

<210> SEQ ID NO 55
<211> LENGTH: 9
<212> TYPE: PRT
<213> ORGANISM: Artificial Sequence
<220> FEATURE:
<223> OTHER INFORMATION: Synthetic

<400> SEQUENCE: 55

Gln Gln Trp Ser Thr Asn Pro Pro Thr
1               5

<210> SEQ ID NO 56
<211> LENGTH: 9
<212> TYPE: PRT
<213> ORGANISM: Artificial Sequence
<220> FEATURE:
<223> OTHER INFORMATION: Synthetic

<400> SEQUENCE: 56

Gln Gln Trp Ser Cys Asn Pro Pro Thr
1               5

<210> SEQ ID NO 57
<211> LENGTH: 360
<212> TYPE: DNA
<213> ORGANISM: Artificial Sequence
<220> FEATURE:
<223> OTHER INFORMATION: Synthetic

<400> SEQUENCE: 57
gatgtacagc ttcaggagtc aggacctggc ctcgtgaaac cttctcagtc tctgtctctc      60
acctgctctg tcactggcta ctccatcacc agtggttatt actggaactg gatccggcag     120
tttccaggaa acaaactgga atggatgggc tacataaact acggcggtag caatggctac     180
aacccatctc tcaaaagtcg gatctccatc actcgggaca catctaagaa ccagttttc      240 ctgaagctga attctgtgac tactgaggac acagctacat attactgtgc aagagactat     300
gatggttact acgaagctct ggacgactgg ggtcaaggaa cctcagtcac cgtctcctca     360

<210> SEQ ID NO 58
<211> LENGTH: 318
<212> TYPE: DNA
<213> ORGANISM: Artificial Sequence
<220> FEATURE:
```

-continued

<223> OTHER INFORMATION: Synthetic

<400> SEQUENCE: 58

```
caaattgttc tctcccagtc tccagcaatc ctgtctgcat ctccagggga gaaggtcaca    60
atgacttgca gggccagctc acgtgtaaat tacatgcact ggtaccagca gaagccagga   120
tcctccccca aaccctggat ttctgccaca tccaacctgg cttctggagt ccctgctcgc   180
ttcagtggca gtgggtctgg gacctcttac tctctcacaa ttagcagagt agagactgaa   240
gatgctgcca cttattactg ccagcagtgg agtagtaacc acccacgtt cggagggggg    300
accaagctgg aaataaaa                                                 318
```

<210> SEQ ID NO 59
<211> LENGTH: 360
<212> TYPE: DNA
<213> ORGANISM: Artificial Sequence
<220> FEATURE:
<223> OTHER INFORMATION: Synthetic

<400> SEQUENCE: 59

```
gaggtacagc ttcaggagtc aggacctggc ctcgtgaaac cttctgagac tctgtctctc    60
acctgcgctg tctctggcta ctccatcacc agtggttatt actggaactg gatccggcag   120
cctccaggaa agaagctgga atggatgggc tacatcaact acggcggtag caatggctac   180
aacccatctc tcaaaagtcg gatcaccatc tctaggaca catctaagaa ccagttttcc    240
ctgaagctga gttctgtgac tgctgccgac acagctgtgt attactgtgc aagagactat   300
gatgcttact acgaagctct ggacgactgg ggtcaaggaa ccacagtcac cgtctcctca   360
```

<210> SEQ ID NO 60
<211> LENGTH: 318
<212> TYPE: DNA
<213> ORGANISM: Artificial Sequence
<220> FEATURE:
<223> OTHER INFORMATION: Synthetic

<400> SEQUENCE: 60

```
gaaattgttc tctcccagtc tccagcaacc ctgtctctgt ctccagggga gagggccaca    60
ctgtcttgca gggccagctc acgtgtaaat tacatgcact ggtaccagca gaagccagga   120
cagtccccca gaccctggat ttctgccaca tccaacctgg cttctggagt ccctgctcgc   180
ttcagtggca gtgggtctgg gacctcttac actctcacaa ttagcagcct ggagccagaa   240
gatttcgccg tgtattactg ccagcagtgg agtagtaacc acccacgtt cggagggggg    300
accaaggtgg aaatcaaa                                                 318
```

<210> SEQ ID NO 61
<211> LENGTH: 574
<212> TYPE: PRT
<213> ORGANISM: Artificial Sequence
<220> FEATURE:
<223> OTHER INFORMATION: Synthetic

<400> SEQUENCE: 61

```
Met Cys Pro Arg Ala Ala Arg Ala Pro Ala Thr Leu Leu Leu Ala Leu
 1               5                  10                  15

Gly Ala Val Leu Trp Pro Ala Ala Gly Ala Trp Glu Leu Thr Ile Leu
            20                  25                  30

His Thr Asn Asp Val His Ser Arg Leu Glu Gln Thr Ser Glu Asp Ser
        35                  40                  45
```

-continued

```
Ser Lys Cys Val Asn Ala Ser Arg Cys Met Gly Gly Val Ala Arg Leu
 50                  55                  60
Phe Thr Lys Val Gln Gln Ile Arg Arg Ala Glu Pro Asn Val Leu Leu
 65                  70                  75                  80
Leu Asp Ala Gly Asp Gln Tyr Gln Gly Thr Ile Trp Phe Thr Val Tyr
                 85                  90                  95
Lys Gly Ala Glu Val Ala His Phe Met Asn Ala Leu Arg Tyr Asp Ala
                100                 105                 110
Met Ala Leu Gly Asn His Glu Phe Asp Asn Gly Val Glu Gly Leu Ile
                115                 120                 125
Glu Pro Leu Leu Lys Glu Ala Lys Phe Pro Ile Leu Ser Ala Asn Ile
130                 135                 140
Lys Ala Lys Gly Pro Leu Ala Ser Gln Ile Ser Gly Leu Tyr Leu Pro
145                 150                 155                 160
Tyr Lys Val Leu Pro Val Gly Asp Glu Val Val Gly Ile Val Gly Tyr
                165                 170                 175
Thr Ser Lys Glu Thr Pro Phe Leu Ser Asn Pro Gly Thr Asn Leu Val
                180                 185                 190
Phe Glu Asp Glu Ile Thr Ala Leu Gln Pro Glu Val Asp Lys Leu Lys
                195                 200                 205
Thr Leu Asn Val Asn Lys Ile Ala Leu Gly His Ser Gly Phe Glu
210                 215                 220
Met Asp Lys Leu Ile Ala Gln Lys Val Arg Gly Val Asp Val Val Val
225                 230                 235                 240
Gly Gly His Ser Asn Thr Phe Leu Tyr Thr Gly Asn Pro Pro Ser Lys
                245                 250                 255
Glu Val Pro Ala Gly Lys Tyr Pro Phe Ile Val Thr Ser Asp Asp Gly
                260                 265                 270
Arg Lys Val Pro Val Val Gln Ala Tyr Ala Phe Gly Lys Tyr Leu Gly
                275                 280                 285
Tyr Leu Lys Ile Glu Phe Asp Glu Arg Gly Asn Val Ile Ser Ser His
                290                 295                 300
Gly Asn Pro Ile Leu Leu Asn Ser Ser Ile Pro Glu Asp Pro Ser Ile
305                 310                 315                 320
Lys Ala Asp Ile Asn Lys Trp Arg Ile Lys Leu Asp Asn Tyr Ser Thr
                325                 330                 335
Gln Glu Leu Gly Lys Thr Ile Val Tyr Leu Asp Gly Ser Ser Gln Ser
                340                 345                 350
Cys Arg Phe Arg Glu Cys Asn Met Gly Asn Leu Ile Cys Asp Ala Met
                355                 360                 365
Ile Asn Asn Asn Leu Arg His Thr Asp Glu Met Phe Trp Asn His Val
370                 375                 380
Ser Met Cys Ile Leu Asn Gly Gly Ile Arg Ser Pro Ile Asp Glu
385                 390                 395                 400
Arg Asn Asn Gly Thr Ile Thr Trp Glu Asn Leu Ala Ala Val Leu Pro
                405                 410                 415
Phe Gly Gly Thr Phe Asp Leu Val Gln Leu Lys Gly Ser Thr Leu Lys
                420                 425                 430
Lys Ala Phe Glu His Ser Val His Arg Tyr Gly Gln Ser Thr Gly Glu
                435                 440                 445
Phe Leu Gln Val Gly Gly Ile His Val Val Tyr Asp Leu Ser Arg Lys
450                 455                 460
Pro Gly Asp Arg Val Val Lys Leu Asp Val Leu Cys Thr Lys Cys Arg
```

-continued

```
                465                 470                 475                 480

Val Pro Ser Tyr Asp Pro Leu Lys Met Asp Glu Val Tyr Lys Val Ile
                485                 490                 495

Leu Pro Asn Phe Leu Ala Asn Gly Gly Asp Gly Phe Gln Met Ile Lys
                500                 505                 510

Asp Glu Leu Leu Arg His Asp Ser Gly Asp Gln Asp Ile Asn Val Val
                515                 520                 525

Ser Thr Tyr Ile Ser Lys Met Lys Val Ile Tyr Pro Ala Val Glu Gly
                530                 535                 540

Arg Ile Lys Phe Ser Thr Gly Ser His Cys His Gly Ser Phe Ser Leu
545                 550                 555                 560

Ile Phe Leu Ser Leu Trp Ala Val Ile Phe Val Leu Tyr Gln
                565                 570
```